US006312683B1

(12) United States Patent
Kingsman et al.

(10) Patent No.: US 6,312,683 B1
(45) Date of Patent: Nov. 6, 2001

(54) EQUINE INFECTIOUS ANEMIA VIRUS VECTORS

(75) Inventors: Alan John Kingsman; Miles William Carroll, both of Oxon; Jonathan Rohll, Berkshire; Kyriacos Mitrophanous, Oxford, all of (GB); Narry Kim, Seoul (KR)

(73) Assignee: Oxford Biomedica (UK) Limited, Oxford (GB)

(*) Notice: Subject to any disclaimer, the term of this patent is extended or adjusted under 35 U.S.C. 154(b) by 0 days.

(21) Appl. No.: 09/238,356

(22) Filed: Jan. 27, 1999

Related U.S. Application Data

(63) Continuation of application No. PCT/GB98/03876, filed on Dec. 22, 1998.

(30) Foreign Application Priority Data

Dec. 22, 1997 (GB) .................................... 9727135
May 22, 1998 (GB) .................................... 9811037

(51) Int. Cl.⁷ .......................... A61K 48/00; C12N 15/00; C12N 15/88

(52) U.S. Cl. .................... 424/93.2; 424/93.1; 424/93.21; 424/93.6; 435/69.1; 435/320.1; 435/325; 435/455; 514/44; 536/23.1

(58) Field of Search ........................... 514/44; 424/93.21, 424/93.1, 93.2, 93.6; 435/320.1, 69.1, 325, 455; 536/230.1

(56) References Cited

U.S. PATENT DOCUMENTS

| 5,981,276 | * | 11/1999 | Sodroski et al. | ................. | 435/320.1 |
| 5,994,136 | * | 11/1999 | Naldini et al. | ................. | 435/455 |
| 6,013,516 | * | 1/2000 | Verma et al. | ................. | 435/325 |
| 6,051,410 | * | 4/2000 | Mazzara et al. | ................. | 435/455 |

FOREIGN PATENT DOCUMENTS

| 0 611 822 A2 | 8/1994 | (EP) . |
| 0 759 471 A1 | 2/1997 | (EP) . |
| WO 91/19798 | 12/1991 | (WO) . |
| WO 92/21750 | 12/1992 | (WO) . |
| WO 95/30755 | 11/1995 | (WO) . |
| WO 97/12622 | * 4/1997 | (WO) . |
| WO 98/39463 | * 9/1998 | (WO) . |

OTHER PUBLICATIONS

Ngo et al., in The Protein Folding Problem and Tertiary Structure Prediction, 1994, Merz et al., (ed.), Birkhauser, Boston, MA, pp. 492–495.*
(Garvey et al., Virology, 175, 2, 391–409), 1990.*
Gazit et al., Virology 189, 344–349), 1992.*
Poblozki et al. (Virology, vol. 193, 2, 981–5(, 1995.*
Anderson, Nature, vol. 392, p. 25–30, 1998.*
Verma et al., Nature, vol. 389, pp. 239–242, 1997.*

Blomer, U., Naldini, I., Kafri, T., Trono, D., Verma, I.M., Gage, F.H.; "Highly efficient and sustained gene transfer in adult neurons with a lentivirus vector", J Virol Sep. 1997;71(9):6641–9.
Blomer, U., Naldini, L., Verma I.M., Trono D., Gage F.H.; "Applications of gene therapy to the CNS."; Hum Mol Genet 1996;5 Spec No:1397–404.
Clever, J., Sassetti, C., Parslow, T.G.; "RNA secondary structure and binding sites for gag gene products in the 5' packaging signal of human immunodeficiency virus type 1." J Virol Apr. 1995;69(4):2101–9.
Clever, J.L., Parslow, T.G.; "Mutant human immunodeficiency virus type 1 genomes with defects in RNA dimerization or encapsidation." J Virol May 1997;71(5):3407–14.
Fuller,S., von Bonsdorff, C.H., Simons, K.; "Vesicular stomatitis virus infects and matures only through the basolateral surface of the polarized epithelial cell line, MDCK.", Cell Aug. 1984;38(1):65–77.
Harrison, G.S., Long, C.J., Maxwell, F., Glode, L.M., Maxwell, I.H.; "Inhibition of HIV production in cells containing an integrated, HIV–regulated diphtheria toxin A chain gene.", AIDS Res Hum Retroviruses Jan. 1992;8(1):39–45.
Hayashi, T., Shioda, T., Iwakura, Y., Shibuta, H.; "RNA packaging signal of human immunodeficiency virus type 1.", Virology Jun. 1992;188(2):590–9.
Kim, V.N., Mitrophanous, K., Kingsman, S.M., Kingsman, A.J.; "Minimal requirement for a lentivirus vector based on human immunodeficiency virus type 1.", J Virol Jan. 1998;72(1):811–6.
Mann, R., Mulligan, R.C., Baltimore, D.; "Construction of a retrovirus packaging mutant and its use to produce helper–free defective retrovirus.", Cell May 1983;33(1):153–9.
Martarano, L., Stephens, R., Rice, N., Derse, D.; "Equine infectious anemia virus trans–regulatory protein Rev controls viral mRNA stability, accumulation, and alternative splicing.", J Virol May 1994;68(5):3102–11.
Payne, S.L., Rausch, J., Rushlow, K., Montelaro, R.C., Issel, C., Flaherty, M., Perry, S., Sellon, D., Fuller, F.; "Characterization of infectious molecular clones of equine infectious anaemia virus.", J Gen Virol Feb. 1994;75 ( Pt 2):425–9, Protein, Nucleotide.
Yee, J.K., Miyanohara, A., LaPorte, P., Bouic, K., Burns, J.C., Friedmann, T.; "A general method for the generation of high–titer, pantropic retroviral vectors: highly efficient infection of primary hepatocytes", Proc Natl Acad Sci U S A Sep. 27, 1994;91(20):9564–8.
Carroll, M.W., Moss, B.E.; "coli beta–glucuronidase (GUS) as a marker for recombinant vaccinia viruses.", Biotechniques Sep. 1995;19(3):352–4, 356.

(List continued on next page.)

Primary Examiner—Dave Trong Nguyen
(74) Attorney, Agent, or Firm—Thomas J. Kowalski; Frommer Lawrence & Haug, LLP

(57) ABSTRACT

A retroviral vector derived from a non-primate lentivirus genome comprising a deleted gag gene wherein the deletion in gag removes one or more nucleotides downstream of nucleotide 350 of the gag coding sequence.

64 Claims, 43 Drawing Sheets

OTHER PUBLICATIONS

Carroll, M.W., Moss, B.; "Host range and cytopathogenicity of the highly attenuated MVA strain of vaccinia virus: propagation and generation of recombinant viruses in a nonhuman mammalian cell line.", Virology Nov. 24, 1997;238(2):198–211.

Chakrabarti, S., Brechling, K., Moss, B.; "Vaccinia virus expression vector: coexpression of beta–galactosidase provides visual screening of recombinant virus plaques.", Mol Cell Biol Dec. 1985;5(12):3403–9.

Chakrabarti, S., Sisler, J.R., Moss, B.; "Compact, synthetic, vaccinia virus early/late promoter for protein expression.", Biotechniques Dec. 1997;23(6):1094–7.

Flexner, C., Hugin, A., Moss, B.; "Prevention of vaccinia virus infection in immunodeficient mice by vector–directed IL–2 expression.", Nature Nov. 19–25, 1987;330(6145):259–62.

Holzer, G.W., Falkner, F.G.; "Construction of a vaccinia virus deficient in the essential DNA repair enzyme uracil DNA glycosylase by a complementing cell line.", J Virol Jul. 1997;71(7):4997–5002.

Mackett, M., Smith, G.L., Moss, B.; "Vaccinia virus: a selectable eukaryotic cloning and expression vector", Proc Natl Acad Sci U S A Dec. 1982;79(23):7415–9.

Mahnel, H., Mayr, A.; "Experiences with immunization against orthopox viruses of humans and animals using vaccine strain MVA." (Article in German), Berl Munch Tierarztl Wochenschr Aug. 1994;107(8):253–6.

Mayr, A., Stickl, H., Muller, H.K., Danner, K., Singer, H.; "The smallpox vaccination strain MVA: marker, genetic structure, experience gained with the parenteral vaccination and behavior in organisms with a debilitated defence mechanism." (Article in German), Zentralbl Bakteriol [B] Dec. 1978;167(5–6):375–90.

Meyer, H., Sutter, G., Mayer, A.; "Mapping of deletions in the genome of the highly attenuated vaccinia virus MVA and their influence on virulence.", J Gen Virol May 1991;72 ( Pt 5):1031–8.

Moss, B., Carroll, M,W., Wyatt, L.S., Bennink, J.R., Hirsch, V.M., Goldstein, S., Elkins, W.R., Fuerst, T.R., Lifson, J.D., Piatak, M., Restifo, N.P., Overwijk, W., Chamberlain, R., Rosenberg, S.A., Sutter, G.; "Host range restricted, non–replicating vaccinia virus vectors as vaccine candidates.", Adv Exp Med Biol 1996;397:7–13.

Panicali, D., Paoletti, E.; "Construction of poxviruses as cloning vectors: insertion of the thymidine kinase gene from herpes simplex virus into the DNA of infectious vaccinia virus.", Proc Natl Acad Sci U S A Aug. 1982;79(16):4927–31.

Soneoka, Y., Cannon, P.M., Ramsdale, E.E., Griffiths, J.C., Romano, G., Kingsman, S.M., Kingsman, A.J.; "A transient three–plasmid expression system for the production of high titer retroviral vectors.", Nucleic Acids Res Feb. 25, 1995;23(4):628–33.

Sutter, G., Moss, B.; "Nonreplicating vaccinia vector efficiently expresses recombinant genes.", Proc Natl Acad Sci U S A Nov. 15, 1992;89(22):10847–51.

Taylor, J., Weinberg, R., Tartaglia, J., Richardson, C., Alkhatib, G., Briedis, D., Appel, M., Norton, E., Paoletti, E.; "Nonreplicating viral vectors as potential vaccines: recombinant canarypox virus expressing measles virus fusion (F) and hemagglutinin (HA) glycoproteins.", Virology Mar. 1992;187(1):321–8.

Paoletti, E., Tartaglia, J., Taylor, J.; "Safe and effective poxvirus vectors—NYVAC and ALVAC.", Dev Biol Stand 1994;82:65–9.

Wyatt, L.S., Moss, B., Rozenblatt, S.; "Replication–deficient vaccinia virus encoding bacteriophage T7 RNA polymerase for transient gene expression in mammalian cells.", Virology Jun. 20, 1995;210(1):202–5.

Wyatt, L.S., Carroll, M.W., Czerny, C.P., Merchlinksy, M., Sisler, J.R., Moss, B.; "Marker rescue of the host range restriction defects of modified vaccinia virus Ankara.", Virology Nov. 25, 1998;251(2):334–42.

Wyatt, L.S., Shors, S.T., Murphy, B.R., Moss, B.; "Development of a replication–deficient recombinant vaccinia virus vaccine effective against parainfluenza virus 3 infection in an animal model.", Vaccine Oct. 1996;14(15):1451–8.

Chanock, R. M., Melnick, J. L., Monath, T. P., Roizman, B. and Straus, S. E., eds. (Philadelphia. New York: Lippincott—Raven Publishers). "Fields Virology", Fields, B. N., Knipe, D. M., and Howley, P. M. (1996).

Journal of Virology 97, 1997, p.6641–6649, Blömer et al., "Highly Efficient and Sustained Gene Transfer in Adult Neurons with a Lentivirus Vector".

Human Molecular Genetics 5, 1996, p. 1397–1404, Blömer et al., "Applications of gene therapy to the CNS".

Journal of Virology 69, 1995, p. 2102–2109, Clever et al., RNA Secondary Structure and Binding Sites for gag Gene Products in the 5' Packaging Signal of Human Immunodeficiency Virus Type 1.

Journal of Virology 71, 1997, p.3407–3414, Clever et al., "Mutant Human Immunodeficiency Virus Type 1 Genomes with Defects in RNA Dimerization or Encapsidation".

Fields of Virology 3, 1996, p. 1767–1996, John M. Coffin, "Retroviridae: The Virsuses and Their Replication".

Cell 38, 1984, p. 65–77, p. 65–77, Fuller et al., "Vesicular Stomatitis Virus Infects and Matures Only through the Basolateral Surface of the Polarized Epithelial Cell Line, MDCK".

Aids Research and Human Retroviruses 8, 1992, p. 39–45, Harrison et al., "Inhibition of HIV Production in Cells Containing an Integrated, HIV–Regulated Diphtheria Toxin A Chain Gene".

Virology 188, 1992, p. 590–599, Hayashi et al., "RNA Packaging Signal of Human Immunodeficiency Virus Type 1".

Journal of Virology 72, 1998, p. 811–816, Kim et al., "Minimal Requirement for a Lentivirus Vector Based on Human Immunodeficiency Virus Type 1".

Journal of Virology 63, 1989, p. 3708–3713, Kim et al., "Temporal Aspects of DNA and RNA Synthesis during Human Immunodeficiency Virus Infection: Evidence for Differential Gene Expression".

Cell, vol. 33, 1983, p. 153–159, Mann et al., "Construction of a Retrovirus Packaging Mutant and Its Use to Produce Helper Free Defective Retroviruses".

Journal of Virology 68, 1994, p. 3102–3111 Martarano et al., "Equine Infectious Anemia Virus trans–Regulatory Protein Rev Controls Viral mRNA Stability, Accumulation, and Alternative Splicing".

Journal of General Virology 75, 1994, p. 425–429, Payne et al., "Characterization of infectious molecular clones of equine infectious anaemia virus".

Proc. Natl. Acad. Sci USA 91, 1994, p. 9564–9568, Yee et al., "A general method for the generation of high–titer, pantropic retroviral vectors: Highly efficient infection of primary hepatocytes".

BioTechniques 19, 1995, p. 352–354, Carroll et al., "*E. coli* beta–Glucuronidase (GUS) as a Marker for Recombinant Vaccinia Viruses".

Virology 238, 1997, p. 198–211, Carroll et al., Host Range and Cytopathogenicity of the Highly Attenuated MVA Strain of Vaccinia.

Virus: Propagation and Generation of Recombinant Viruses in a Nonhuman Mammalian Cell Line.

Molecular and Cellular Biology, 5, 1985, p. 3403–3409, Chakrabarti et al., "Vaccinia Viruse expression Vector: Coexpression of beta–Galactosidase Provides Visual Screening or Recombinant Virus Plaques".

BioTechniques 23, 1997, p. 1094–1097, Chakrabarti et al., "Compact, Synthetic, Vaccinia Virus Early/Late Promoter for Protein Expression".

J. Mol. Biol. 210, 1989, p. 749–769, Davison et al., "Structure of Vaccinia Virus Early Promoters".

J. Mol. Biol. 210, 1980, p. 771–784, Davison et al. "Structure of Vaccinia Virus Late Promoters".

Current Protocols in Molecular Biology 1998, Suppl. 43 Unit 16.16, Earl et al., "Preparation of Cell Cultures and Vaccinia Virus Stocks".

Current Protocols in Molecular Biology 1998, Suppl. 43 Unit 16.17, Earl et al., "Generation of Recombinant Vaccinia Viruses".

Nature 330, 1987, p 259–262, Flexner et al. "Prevention of vaccinia virus infection in immunodeficient mice by vector-–directed IL–2 expression".

Journal of Virology 71, 1997, p. 4997–5002, Holzer et al., "Construction of a Vaccinia Virus Deficient in the Essential DNA Repair Enzyme Uracil DNA Glycosylase by a Complementing Cell Line".

Proc. Natl. Acad. Sci. USA 79, 1982, p. 7415–7419, Mackett et al., "Vaccinia virus: A selectable eukaryotic cloning and expression vector".

Berl. und Münchener Tierärtzliche Wochenschrift 107, 1994, p. 253–256, Mahnel et al., "Erfahrungen bei der Schutzimpfung gegen Orthopocken von Mensch und Tier mit dem Impstamm MVA", English translation.

Zentralbl. Bakteriol, 1978, p. 375–390, Mayr et al., "The Smallpox Vaccination Strain MVA: Marker, Genetic Structure, Experience Gained with the Parenteral Vaccination and Behavior in Organisms with a Debilitated Defence Mechanisms" (English Abstract).

Journal of General Virology 72, 1991, p. 1031–1038, Meyer et al., "Mapping of deletions in the genome of the highly attenuated vaccinia virus MVA and their influence on virulence".

Fields Virology 3, 1996, p. 2637–2672, Bernard Moss, "Poxviridae: The Viruses and Their Replication".

Adv Exp Med Biol 367, 1996, p. 7–13, Moss et al., "Host Range Restricted Non–Replicating Vaccinia Virus Vectors as Vaccine Candidates".

Proc. Natl. Acad. Sci. USA, 79, 1982, p. 4927–4931, Panicali et al., "Construction of poxviruses as cloning vectors: Insertion of the thymidine kinase gene from herpes simplex virus into the DNA of infectious vaccinia virus".

Nucleic Acids Research, vol. 23, 1995, p. 628–633, Soneoka et al., "A transient three–plasmid expression system for the production of high titer retroviral vectors".

Proc. Natl. Acad. Sci. USA, 1992, p. 10847–10851, Sutter et al., "Nonreplicating vaccinia vector efficiently expresses recombinant genes".

Virology 187, 1992, p. 321–328, Taylor et al., "Nonreplicating Viral Vectors as Potential Vaccines: Recombinant Canarypox Virus Expressing Measles Virus Fusion (F) and Hemagglutinin (HA) Glycoproteins".

Dev Biol Stand 82, 1994, p 65–69, Paoletti et al., "Safe and Effective Poxvirus Vectors–NYVAC and ALVAC".

Virology 210, 1995, p 202–205, Wyatt et al., "Replication-–Deficient Vaccinia Virus Encoding Bacteriophage T7 RNA Polymerase for Transient Gene Expression in Mammalian Cells".

Virology 251, 1998, p 334–342, Wyatt et al., "Marker Rescue of the Host Range Restriction Defects of Modified Vaccinia Virus Ankara".

Vaccine 14, 1996, p. 1451–1458, Wyatt et al., "Development of a replication–deficient recombinant vaccinia virus vaccine effective against parainfluenza virus 3 infection in an animal model".

Science, vol. 272 Apr. 12, 1996, pp. 263–267, L. Naldini et al., "In vivo Gene Delivery and Stable Transduction of Nondividing cells by a Lentiviral Vector", XP000583652.

Nature Biotechnology, vol. 15, Sep. 1997, pp. 871–875, Zufferey et al., "Multiply attenuated lentiviral vector achieves efficient gene delivery in vivo", XP–002056816.

Journal of Virology, Apr. 1996, pp. 2581–2585, Akkina et al. "High–Efficiency Gene Transfer into $CD34^+$ Cells with a Human Immunodeficiency Virus Type 1–Based Retroviral Vector Pseudotyped with Vesicular Stomatitis Virus Envelope Glycoprotein G".

Proc. Natl. Acad. Sci. USA, vol. 90, Sep. 1993, pp. 7941–7945, Barillari et al., "The Tat protein of human immunodeficiency virus type 1, a growth factor for AIDS Kaposi sarcoma and cytokine–activated vascular cells, induces adhesion of the same cell types by using integrin receptors recognizing the RGD amino sequence".

Journal of Virology, May 1992, pp. 2731–2739, Buchschacher, Jr. et al., "Human Immunodeficiency Virus Vectors for Inducible Expression of Foreign Genes".

Nature, vol. 365, Oct. 14, 1993, pp. 666–669, Bukrinsky et al., "A nuclear localization signal within HIV–1 matrix protein that governs infection of non–dividing cells".

Journal of Virology, Nov. 1996, pp. 8234–8240, Cannon et al., "Murine Leukemia Virus–Based Tat–Inducible Long Terminal Repeat Replacement Vectors: a New System for Anti–Human Immunodeficiency Virus Gene Therapy".

Molecular and Cellular Biology, Aug. 1987, pp. 2745–2752, Chen et al., "High–Efficiency Transformation of Mammalian Cells by Plasmid DNA".

Journal of Acquired Immune Deficiency Syndromes, 1994 Raven Press, Ltd., New York, pp. 655–664, Echetebu et al., "Construction and Characterization of a Potent HIV–2 Tat Transdominant Mutant Protein".

Nature, vol. 345, May 3, 1990, pp. 84–87, Ensoli et al., "Tat protein of HIV–1 stimulates growth of cells derived from Kaposi's sarcoma lesions of AIDS patients".

Journal of Virology, Feb. 1996, pp. 1027–1032, Gallay et al., "Role of the Karyopherin Pathway in Human Immunodeficiency Virus Type 1 Nuclear Import".

Proc. Natl. Acad. Sci. USA, vol. 91, Jul. 1994, pp. 7311–7315, Heinzinger et al., "The Vpr protein of human immunodeficiency virus type 1 influences neclear localization of viral nucleic acids in nondividing host cells".

Fields Virology, Third Edition, 1996, chapter 62, pp. 1977–1996, Joag et al., "Lentiviruses".

Journal of Virology, Oct. 1995, pp. 6304–6313, Jowett et al., "The Human Immunodeficiency Virus Type 1 vpr Gene Arrestes Infected T Cells in the $G_2$ + M Phase of the Cell Cycle".

Journal of Virology, Sep. 1989, pp. 3708–3713, Sunyoung Kim et al., "Temporal Aspects of DNA and RNA Synthesis during Human Immunodeficiency Virus Infection: Evidence for Differential Gene Expression".

Journal of Virology, Sep. 1989, pp. 4085–4087, Lever et al., "Identification of a Sequence Required for Efficient Packaging of Human Immunodeficiency Virus Type 1 RNA into Virions".

Cell, vol. 72, Feb. 26, 1993 pp. 541–550, Levy et al., "Induction of Cell Differentiation by Human Immunodeficiency Virus 1 vpr".

Cell, vol. 72, Feb. 26, 1993 pp. 1245–1252.

Journal of Virology, vol. 69, Feb. 1995, pp. 1243–1252, Levy et al., "Extracellular Vpr Protein Increases Cellular Permissiveness to Human Immunodeficiency Virus Replication and Reactivates Virus from Latency".

Proc. Natl. Acad. Sci. USA, vol. 90, Sep. 1993, pp. 8000–8004, Lisziewicz et al., "Inhibition of human immunodeficiency virus type 1 replication by regulated expression of a polymeric Tat activation response RNA decoy as a strategy for gene therapy in AIDS".

Virology 212, 1995, pp. 331–339, Mahalingham et al., "Functional Analysis of HIV–1 Vpr: Identification of Determinants Essential for Subcellular Localization".

Science, vol. 272, Apr. 12, 1996, pp. 263–267, Naldini et al., "In Vivo Gene Delivery and Stable Transduction of Nondividing Cells by a Lentiviral Vector".

Proc. Natl. Acad. Sci. USA, vol. 93, Oct. 1996, pp. 11382–11388, Naldini et al., Efficient transfer, integration, and sustained long–term expression of the transgene in adult rat brains injected with a lentiviral vector.

Journal of Virology, vol. 64, No. 1, Nov. 1990, pp. 5270–5276, Page et al., "Construction and Use of a Human Immunodeficiency Virus Vectro for Analysis of Virus Infectivity".

Journal of Virology, vol. 65, No. 1, Jan. 1991, pp. 531–536, Poznansky et al., "Gene Transfer into Human Lymphocytes by a Defective Human Immunodeficiency Virus Type 1 Vector".

Journal of General Virology, vol. 76, 1995, pp. 691–696, Richardson et al., "Helper virus free transfer of human immunodeficiency virus type 1 vectors".

Human Gene Therapy 7, vol. 77, Sep. 10, 1996, pp. 1781–1790, Ross et al., "Gene Therapy in the United States: A Five–Year Status Report".

The Journal of Clinical Investigation, Inc., vol. 88, Sep. 1991, 1043–1047, Shimada et al., "Targeted and Highly Efficient Gene Transfer into CD4$^+$ Cells by a Recombinant Human Immunodeficiency Virus Retroviral Vector".

Journal of General Virology, 1996, pp. 1611–1621, Tomonaga et al., "Molecular biology of the feline immunodeficiency virus auxiliary genes".

Journal of Virology, vol. 68, No. 1, Jan. 1994, pp. 510–516, Fred Hutchinson Cancer Research, "Passage through Mitosis Is Required for Oncoretroviruses but Not for the Human Immunodeficiency Virus".

Journal of Virology, vol. 66, No. 5, May 1992, pp. 2731–2739, Buchschacher et al., "Human Immunodeficiency Virus Vectors for Inducible Expression of Foreign Genes".

Science, vol. 272, Apr. 12, 1996, Naldini et al., "In Vivo Gene Delivery and Stable Transduchtion of Nondividing Cells by a Lentiviral Vector".

British Medical Bulletin, 1995, vol. 51, pp. 12–30, R G Vile et al., "Retroviruses as vectors".

Journal of Virology, Jul. 1988, pp. 2464–2473, Bowtell et al., "Comparison of Expression in Hemopoietic Cells by Retroviral Vectors Carrying Two Genes".

Blood, vol. 84, No. 6, Sep. 15, 1994, pp. 1812–1822, Correll et al., "Retroviral Vector Design for Long–Term Expression in Murine Hematopoietic Cells In Vivo".

Cell, vol. 39, Dec. 1984, pp. 458–467, Emerman et al., "Genes with Promoters in Retrovirus Vectors Can Be Independently Suppressed by an Epigenentic Mechanism".

Molecular and Cellular Biology, Dec. 1991, pp. 5848–5859, Ghattas et al., "The Encephalomyocarditis Virus Internal Ribosome Entry Site Allows Efficient Coexpression of Two Genes from a Recombinant Provirus in Cultered Cells and in Embryos".

Proc. Natl. Acad. Sci. USA, vol. 86, May 1989, pp. 3519–3523, Hantzopoulos et al., "Improved gene expression upon transfer of the adenosine deaminase minigene outside the transcriptional unit of a retroviral vector".

The Journal of Biological Chemistry, vol. 266, issue of May 5, 1991, pp. 6416–6425, Hatzoglou et al., "Hormonal Control of Interacting Promoters Introduced into Cells by Retroviruses".

The Journal of Biological Chemistry, vol. 268, No. 33, Nov. 26, 1988, pp. 17798–17808, Hatzoglou et al., "Hormonal Regulation of Chimeric Genes Containing the Phospphoenolpyruvate Carboxykinase Promoter Regulatory Region in Hepatoma Cells Infected by Murine Retroviruses".

Human Gene Therapy, 1992, pp. 381–390, Hantzopoulos et al., "Comparison of the Expression of a Mutant Dihydofolate Reductase under Control of Different Internal Promoters in Retroviral Vectors".

Virology 195, 1993, pp. 1–5, McLachlin et al., "Factors Affecting Retroviral Vector Function and Structural Integrity".

Molecular and Cellular Biology, Apr. 1988, pp. 1803–1808, Overall et al., "Stably Transmitted Triple–Promoter Retroviral Vectors and Their Use in Transformation of Primary Mammalian Cells".

Proc. Natl. Acad. Sci. USA, vol. 88, Jun. 1991, pp. 4626–4630, Scharfmann et al., "Long–term in vivo expression of retrovirus–mediated gene transfer in mouse fibroblast implants".

Gene Therapy, 1994, pp. 307–316, Vile et al., "A comparison of the properties of different retroviral vectors containing containing the murine tyrosinase promoter to achieve transcriptionally targeted expression of the HSVtk or IL–2 genes".

Virology vol. 171, 1989, pp. 331–341, Lixu et al., "Factors Affecting Long–Term Stability of Moloney Murine Leukemia Virus–Based Vectors".

Proc. Natl. Acad. Sci. USA, vol. 84, Aug. 1987, pp. 5197–5201, Jiing–Kuan Yee et al., "Gene expression from transcriptionally disabled retroviral vectors".

AIDS. vol. 6 1995, pp. S19–S32, Bryan R. Cullen, "Regulation of HIV gene expression".

* cited by examiner

EIAV genome
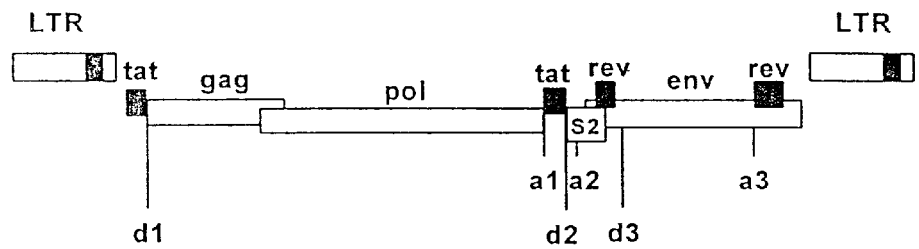
pESP
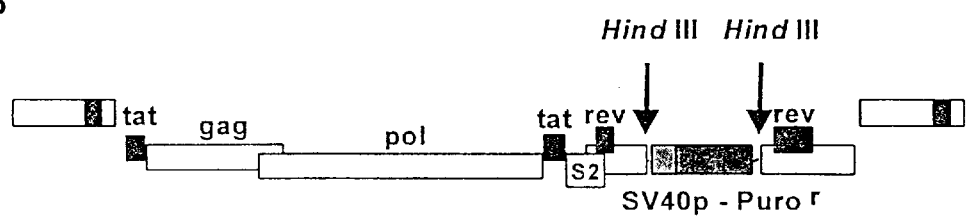
pONY3
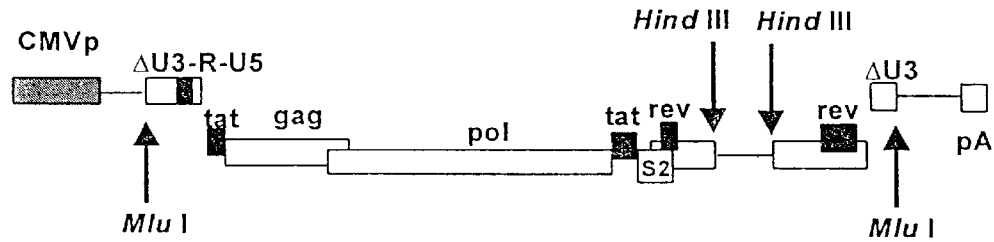
pONY2.1nlslacZ
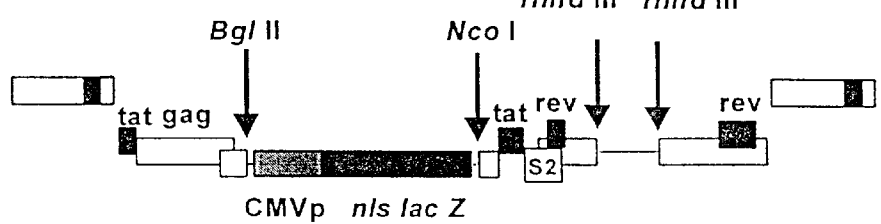
FIG. 1

A. LTR
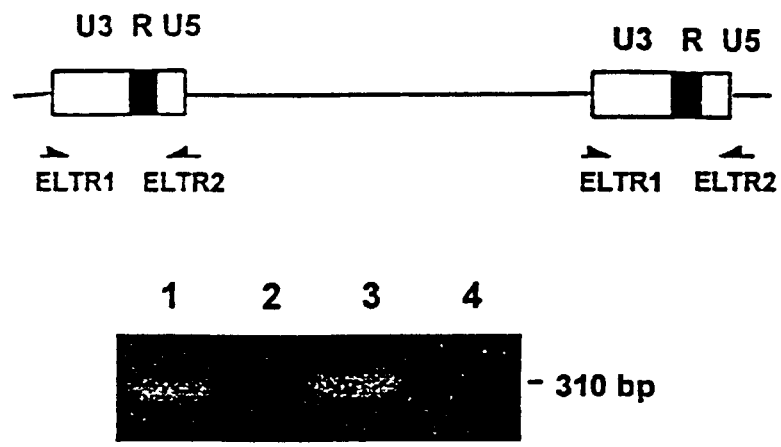
B. pol
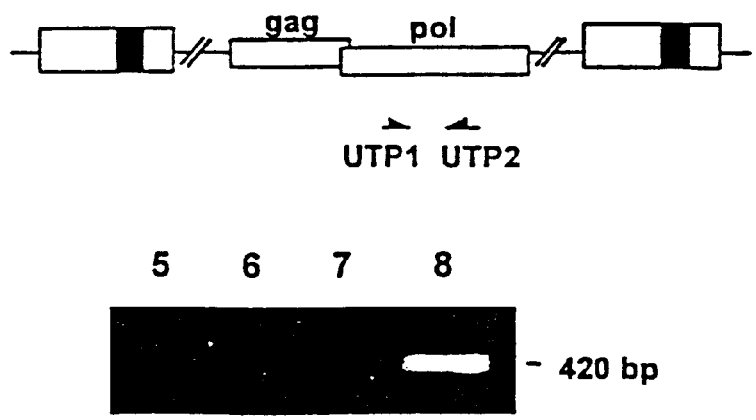
FIG. 2

FIG. 4

ENERGY = -120.9  EIAv plus C

|   | Titres (l.f.u./ml) |
|---|---|
| 1. pONY3.0 + pCI-Neo | $(1.0 \times 10^5)$ |
| 2. pONY3.0 + pCI-Rev | $(8.0 \times 10^4)$ |
| 3. pONY3.1 + pCI-Neo | $(2.0 \times 10^5)$ |
| 4. pONY3.1 + pCI-Rev | $(1.8 \times 10^5)$ |
| 5. pHORSE + pCI-Neo | $(1.0 \times 10^1)$ |
| 6. pHORSE + pCI-Rev | $(2.0 \times 10^3)$ |
| 7. pHORSE3.1 + pCI-Neo | $(2.0 \times 10^2)$ |
| 8. pHORSE3.1 + pCI-Rev | $(8.0 \times 10^4)$ |
| 9. pCI-Neo | $(<1.0)$ |

Me1 5'-tcgatagatctgagtccgttacataactacgg-3'
Me2 5'-gatctcgaacagacaaactagagacagggactgcaaacagcaagagggctttattggg-3'
Me3 5'-gtccctgtctctagtttgtctgttcgagat-3'
Me4 5'-ggggatccactagttctagagatattc-3'
Me5 5'-ccttagacctggagattcgaagcgaag-3'
Me6 5'-ccaaacctacagggtggggtctttcatttacaaggttatgagagcatcagcaac-3'
Me7 5'-aatgaaagaccccacctgtaggtttgg-3'
Me8 5'-gtagagtgcccaattgccagtatacactccgctatcgctac-3'

FIG. 18

```
CTAAATTGTAAGCGGTTAATATTTTGTTAAATTTTGTTAAATCAGCTCATTTTTTAACCAATAGGCCGAAATCCCTTATAAATCAAAAGAATAGACCGAGATAGGGTTGAGTGT
TGTTCCAGTTTGGAACAAGAGTCCACTATTAAAGAACGTGGACTCAAACGTCTATCAGGGCGATGGCCACTACGGTGAACCATCACCCTAATCAGTTTTTGGGTCGAGGTGCCG
TAAGCACTAAATCGGAACCCTAAAGGAGCCCCGATTTAGAGCTTGAAAAGCCAACCTGCTTATCCACTCACTATAGGGAGACCGCAGATCGAGTCGGTACATAACTTACGGT
AAATGGCCCGCTGACCGCCAACGACCCCCAACGCTATCATATGACGTCAATAATGACGGTATGTTCCCATTGACGTCAATAGGGACTTTCCTACTTGGCAGTACATCTACGTATTAGT
GCAGTACATCAAGTGTATCATATGCCAAGTACGCCCCCTATTGACGTCAATGACGGTAAATGGCCCGCCTGGCATTATGCCCAGTACATGACCTTATGGGACTTTCCTACTTGGCACCAAAATCAACGGGA
CTTTCCAAAATGTCGTAACAACTCCGCCCCATTGACGCAAAATGGGCGGTAGGCGTGTACGGTGGGAGGTCTATATAAGCAGAGCTCGTTTAGTGAACCGTCAGATCTCCTAGA
CGTATTCCCAATAAAGCCTCTTGCTGTTTGCATCGAATTCGCCCTTCCCTCGAGTAGTCGACGCTCGCAGATCCACTAGTTCTAGAGCGGCCGCCACCGCGGTGGAGCTCCAGCT
CAGTTGGGCGCCCGAACAGGGGACCCTTTGACATGGGACCCTTTGGGCCATTACAACACCCCTTTCACATATCACCAACAGTAACAGCTGTAATAGCACTACTAGAGTCATCATGA
GACAGGTAAGATGGAACCCTTTGACATGCAGCTCAGGACCCGGGACCCGTCAGAAGGCTTACAAGCTGAGGCCGGACCCTCAAGCCCACAGCCCTAAGCCCCCCCAGACACAGAG
TACCAACTTTGTAAAGAAAAGGACTGGAGCTGCAGTCATTCCAGCTCCAAGCGCTCAGGGGTTCAGAGAAGGTTAGAGATGTGAGCGGAATCAGGACCCTTTGAAAGAACATGTGGGCAATTTCTGCTGTAAAGAT
GGGCCTCCAGATTAATAATGTAGTAAGAGACTCCGGATCGGTCGAGGGCATCATTTGGTCAGGAGGCACGATGGCGCCGCTTTGGCATTACCGCATGGCCATTGCCATTGCATACGTTGTATCCATATCAT
GAATTCGCAGGATTCATTTATATTGGCTCATGCCCATTGACATTGACATTGATTATTAATAGTTCATTGATTATATTATAATATCAATATCGGTCATTCATAGCCCATATATGAGTTCCGGTTACATACTT
ACGGTAAATGGCCCGCCTGGCTGACCGCCCAACGACCCCCGCCCATTGACGTCAATAATGACGTATGTTCCCATAGTAACGCCAATAGGGACTTTCCATTGACGTCAATGGGTGGAGTATTTACGGTAAACTGCC
CACTTGGCAGTACATCAAGTGTATCATATGCCAAGTACGCCCCCTATTGACGTCAATGACGGTAAATGGCCCGCCCTGGCATTATGCCCAGTACATGACCTTATGGGACTTTCCTACTTGGCAGTACATCTACGTA
TTAGTCATCGCTATTACCATGGTGATGCGGTTTTGGCAGTACATCAATGGGCGTGGATAGCGGTTTGACTCACGGGGATTTCCAAGTCTCCACCCCATTGACGTCAATGGGAGTTTGTTTTGGCACCAAAATCAA
CGGGACTTTCCAAAATGTCGTAACAACTCCGCCCCATTGACGCAAATGGGCGGTAGGCATGTACGGTCTATATAAGCAGAGCTCGTTTAGTGAACCGTCAGATCGCCTGGAGACGCCATCCACGCTGT
TTTGACCTCCATAGAAGACACCGGGACCGATCAGCCTCGACTGTGCCTTCTACCAGTCTCCAGGATCCGCTGAATATGGGCCATCATACGGCCCTTCCCAGCAGAGCCCATCTACACCAACGTAA
GTGACTGGGAAAACCTGGCGTTACCCAACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGCGAATGGC
GCTTTGCCTGGTTTCCGGCACCAGAAGCGGTGCCGGAAAGCTGGCTGGAGTGCGATCTTCCTGAGGCCGATACTGTCGTCGTCCTCAAACTGGCACGATGCACGGTTACGATGCGCCCATCTACACCAACGTAA
CCTATCCCATTACGGTCAATCCGCCGTTTGTTCCCACGGAGAATCCGACGGGTTGTTACTCGCTCACATTTAATGTTGATGAAAGCTGGCTACAGGAAGGCCAGACGCGAATTATTTTTGATGGCGTTAACTCGG
CGTTTCATCTGTGGTGCAACGGGCGCTGGGTCGGTTACGGCCAGGACAGTCGTTTGCCGTCTGAATTTGACCTGAGCGCATTTTTACGCGCCGGAGAAACCGCCGTCTCGGTTGAGTGACG
GCAGTTATCTGGAAGATCAGGATATGTGCGGTGAGTTGCTGTACTACGGGGATGCAGTGTTCACCCGCTTCCACGCTTGCCAGCCTTTCGGTGGCACGGAATATTATCGATGAGCGTGGTG
TACTGGAGTGAAGTTGAGTCCGTCACACTACGTCTGAACGTCGAAAAACCGAAACTGTGGAGCCGAATGGTAACACCGCCGTCACCAGCGCTGTTGAAGCAGAAGCCTGCG
GTTATGCCGGATCGGTTTCCGCGAGGTGCGGATTGAAAATGGTCTGCTGCTGAACCGGCAAGCCGTTGCTGATTGAGGCGCGATCATCTCTGCATGGTGCACGATGAGAAACCACG
ATGTCGGTTTCCGCGAGGTGCGGATTGAAAATGGTCTGCTGCTGAACCGGCAAGCCGTTGCTGATTGAGGCGCGATCATCTCTGCATGGTGCACGATGAGAAACCACG
AGGATATCCTGATGAAGCAGAACAACTTTAACGCCGTGCGCTGTTCGCATTATCCGAACCATCCGCGTGGTACACGCCGGATCATCACCCGACCGTGGCGATCAATATGAAACCCACG
GCATGGTGCCAATGAATCGTCTGACCGATGAACTGCGTTCCGCCGAGCGTTATCCGGCGATCGTAATCGTGACCCCGTCACTACCAGCAGCAGGAATGGCCGATAACGCGCTGATGAAG
ACGGACGCTAATCACGACGCGTGAGCTCGTGGATCAAATTGTGTCAAACGTAGACCCACCGTGCAACCGCCCACCGATATATTATTCCCGATGTACGCGCGTGGATGATGAAG
ACCAGCCTTCCCCCAGCTGTGCGGAATGGTCAGTTCCCGCTATAAATGGTCGTTACATGGTTCAGGGCGCTTCGGACTTCGGACTGAACGCCTGAAATACTGGCTCTAAATATGGCC
AGGCTTCTGTGTTCGTGCCGACCGATGAACAACGCTATGCCCCACCGGATCTGCCCGATTATCAATATCGGAACGATCTCGCTATCACCTGTGGTTTGGCAATCGAAGTCGAA
GCCAGTTCTGTAGGCTTGTCTCTTCGACCGACTGGGCATCGGGCATCTGCAATCGCGGGAAGACACCACTACCCGCAGCAGGGCGTCCCACCGTATCAGGATCCTAAAAAACAACTGCTGACGC
AGGAAGATCCAACGCCACGCGTCGACTCCGCGCAATGGTCGCCAACGGCATCGTCAAGCCGCTGCCAAGTGTAACGCCGCCAAGGCCGCAAGAGGCAGCAGTACGCCGGTGGCGCATTACGCGCAGGGCGTGTTGC
CCGCGCGCACCCAGCTGCCCTTGATCACCGCTGGAGTGCCCGATGCCTAACGGATACCGCTCAACGGAATGCGATATCGTTGGGTTTGCGACCGCGGGTCGCCAAGAGGCTGTTCGGTGGCTAAAGCTAAGCCCGCG
GAGGCGAGAGATGGGAGATCTGTGCTCCATTGGCCTCGCTTCTGGGGAATATTAAGGTGGGCCATAGACGAGAATCGTTTAATGTACTTCACCGATATGATTGAGGCGCGGAGCGCCGACGCGCCGTTGTTGC
GCTGCGACAGCTTCAACGACAGCGCGAAATGCACATGGTGCTGCTGATACGTAACTGTGTGTGCTTCCCACGCGAATGGTCGATATCAATGGCTGCAGCAAAAAAAAAAAAAAAGCTGCATTGGGATGCAGATC
AGTGCAGGGCGAGCGCGCACGCGAGCGATTGGCCCGCTGGCCTGCATCTGGAAAATCAACGCGCATCATTGCGGAATCTTAAACGCCCAGAACCCCCAAACATCGAAAACGACTGCTGAAGAAAACAACTGCTGCTG
ATGTTGAAGTGGCGAGCGATACAGGGTAACGAAATAAGCATGTGTGGTCTGTCAGCCGGAAAACTTAATCAGCGGGAAGAGAGCGGGTAACTGGTATAAAGCTGGACGGGAAGAAACCATCGCGATTACCCGTTG
GTTTTGACCGGATCGATCTGGCCATTGTCAGACATGTATCAGGAAGCCAAAAACCGCGCTGGGGCGGAATTACCACCCTCGCGGCGTGCACGCGCGACGCTGTTGC
```

EMVA5

CCCTC|ATGGAAA|CCCCACAGTTCCCCCTTG

The boxed sequence is the mutated TTTTTAT sequence within U3.

EMVA6

Bgl II      Mun I
CTGA|AGATCT|GAATCTGAGTGC|CAATTG|CAG

EMVA7

Mun I
CTGA|CAATTG|GGCACTCAGATTC

EMVA8

Bgl II
CATC|AGATCT|T|AAAAAAAA|TGATGAGAGAATTATATTTATTAC

The AAAAAAAA sequence contains the termination signal (TTTTTNT) for the early promoter.

FIG. 21

EMVA9

Pac I        Psyn
AGC|TTAATTAA|AAAATTTGAAATTTTATTTTTTTTTGGAATATAAATAAGCTCGAAGT
CTGAGTGCCCCTGATGAGCCGGCCGAAAGGCCGAAACCTGCGTCGACACGCCAGGTC
GGGCACTCAGATTCTGCGGGTC
▲ start of R after cleavage by the hammerhead ribozyme.

The ribozyme sequence is underlined.

FIG. 25

```
AGCTTTTGCGATCAATAAATGGATCACAACCAGTATCTCTTAACGATGTTCTTCGCAGATGATGAT
TCATTTTTAAGTATTTGGCTAGTCAAGATGATGAAATCTTCATTATCTGATATATTGCAAATCAC
TCAATATCTAGACTTTCTGTTATTATTATTGATCCAATCAAAAAATAAATTAGAAGCCGTGGGTCA
TTGTTATGAATCTCTTTCAGAGGAATACAGACAATTGACAAAATTCACAGACTTTCAAGATTTTAA
AAAACTGTTTAACAAGGTCCCTATTGTTACAGATGGAAGGGTCAAACTTAATAAAGGATATTTGTT
CGACTTTGTGATTAGTTTGATGCGATTCAAAAAAGAATCCTCTCTAGCTACCACCGCAATAGATCC
TGTTAGATACATAGATCCTCGTCGCAATATCGCATTTTCTAACGTGATGGATATATTAAAGTCGAA
TAAAGTGAACAATAATTAATTCTTTATTGTCATCATGAACGGCGGACATATTCAGTTGATAATCGG
CCCCATGTTTTCAGGTAAAAGTACAGAATTAATTAGACGAGTTAGACGTTATCAAATAGCTCAATA
TAAATGCGTGACTATAAAATATTCTAACGATAATAGATACGGAACGGGACTATGGACGCATGATAA
GAATAATTTTGAAGCATTGGAAGCAACTAAACTATGTGATCTCTTGGAATCAATTACAGATTTCTC
CGTGATAGGTATCGATGAAGGACAGTTCTTTCCAGACATTGTTGAATTAGATCGATAAAAATTAAT
TAATTACCCGGGTACCAGGCCTAGATCTGTCGACTTCGAGCTTATTTATATTCCAAAAAAAAAAAA
TAAAATTTCAATTTTTAAGCTTTCACTAATTCCAAACCCACCCGCTTTTTATAGTAAGTTTTTCAC
CCATAAATAATAAATACAATAATTAATTTCTCGTAAAAGTAGAAAATATATTCTAATTTATTGCAC
GGTAAGGAAGTAGATCATAACTCGAGCATGGGAGATCCCGTCGTTTTACAACGTCGTGACTGGGAA
AACCCTGGCGTTACCCAACTTAATCGCCTTGCAGCACATCCCCCTTTCGCCAGCTGGCGTAATAGC
GAAGAGGCCCGCACCGATCGCCCTTCCCAACAGTTGCGCAGCCTGAATGGCGAATGGCGCTTTGCC
TGGTTTCCGGCACCAGAAGCGGTGCCGGAAAGCTGGCTGGAGTGCGATCTTCCTGAGGCCGATACT
GTCGTCGTCCCCTCAAACTGGCAGATGCACGGTTACGATGCGCCCATCTACACCAACGTAACCTAT
CCCATTACGGTCAATCCGCCGTTTGTTCCCACGGAGAATCCGACGGGTTGTTACTCGCTCACATTT
AATGTTGATGAAAGCTGGCTACAGGAAGGCCAGACGCGAATTATTTTTGATGGCGTTAACTCGGCG
TTTCATCTGTGGTGCAACGGGCGCTGGGTCGGTTACGGCCAGGACAGTCGTTTGCCGTCTGAATTT
GACCTGAGCGCATTTTTACGCGCCGGAGAAAACCGCCTCGCGGTGATGGTGCTGCGTTGGAGTGAC
GGCAGTTATCTGGAAGATCAGGATATGTGGCGGATGAGCGGCATTTTCCGTGACGTCTCGTTGCTG
CATAAACCGACTACACAAATCAGCGATTTCCATGTTGCCACTCGCTTTAATGATGATTTCAGCCGC
GCTGTACTGGAGGCTGAAGTTCAGATGTGCGGCGAGTTGCGTGACTACCTACGGGTAACAGTTTCT
TTATGGCAGGGTGAAACGCAGGTCGCCAGCGGCACCGCGCCTTTCGGCGGTGAAATTATCGATGAG
CGTGGTGGTTATGCCGATCGCGTCACACTACGTCTCAACGTCGAAAACCCGAAACTGTGGAGCGCC
GAAATCCCGAATCTCTATCGTGCGGTGGTTGAACTGCACACCGCCGACGGCACGCTGATTGAAGCA
GAAGCCTGCGATGTCGGTTTCCGCGAGGTGCGGATTGAAAATGGTCTGCTGCTGCTGAACGGCAAG
CCGTTGCTGATTCGAGGCGTTAACCGTCACGAGCATCATCCTCTGCATGGTCAGGTCATGGATGAG
CAGACGATGGTGCAGGATATCCTGCTGATGAAGCAGAACAACTTTAACGCCGTGCGCTGTTCGCAT
TATCCGAACCATCCGCTGTGGTACACGCTGTGCGACCGCTACGGCCTGTATGTGGTGGATGAAGCC
AATATTGAAACCCACGGCATGGTGCCAATGAATCGTCTGACCGATGATCCGCGCTGGCTACCGGCG
ATGAGCGAACGCGTAACGCGAATGGTGCAGCGCGATCGTAATCACCCGAGTGTGATCATCTGGTCG
CTGGGGAATGAATCAGGCCACGGCGCTAATCACGACGCGCTGTATCGCTGGATCAAATCTGTCGAT
CCTTCCCGCCCGGTGCAGTATGAAGGCGGCGGAGCCGACACCACGGCCACCGATATTATTTGCCCG
ATGTACGCGCGCGTGGATGAAGACCAGCCCTTCCCGGCTGTGCCGAAATGGTCCATCAAAAAATGG
CTTTCGCTACCTGGAGAGACGCGCCCGCTGATCCTTTGCGAATACGCCCACGCGATGGGTAACAGT
CTTGGCGGTTTCGCTAAATACTGGCAGGCGTTTCGTCAGTATCCCCGTTTACAGGGCGGCTTCGTC
TGGGACTGGGTGGATCAGTCGCTGATTAAATATGATGAAAACGGCAACCCGTGGTCGGCTTACGGC
GGTGATTTTGGCGATACGCCGAACGATCGCCAGTTCTGTATGAACGGTCTGGTCTTTGCCGACCGC
ACGCCGCATCCAGCGCTGACGGAAGCAAAACACCAGCAGCAGTTTTTCCAGTTCCGTTTATCCGGG
```

FIG. 37

```
CAAACCATCGAAGTGACCAGCGAATACCTGTTCCGTCATAGCGATAACGAGCTCCTGCACTGGATG
GTGGCGCTGGATGGTAAGCCGCTGGCAAGCGGTGAAGTGCCTCTGGATGTCGCTCCACAAGGTAAA
CAGTTGATTGAACTGCCTGAACTACCGCAGCCGGAGAGCGCCGGGCAACTCTGGCTCACAGTACGC
GTAGTGCAACCGAACGCGACCGCATGGTCAGAAGCCGGGCACATCAGCGCCTGGCAGCAGTGGCGT
CTGGCGGAAAACCTCAGTGTGACGCTCCCCGCCGCGTCCCACGCCATCCCGCATCTGACCACCAGC
GAAATGGATTTTTGCATCGAGCTGGGTAATAAGCGTTGGCAATTTAACCGCCAGTCAGGCTTTCTT
TCACAGATGTGGATTGGCGATAAAAAACAACTGCTGACGCCGCTGCGCGATCAGTTCACCCGTGCA
CCGCTGGATAACGACATTGGCGTAAGTGAAGCGACCCGCATTGACCCTAACGCCTGGGTCGAACGC
TGGAAGGCGGCGGGCCATTACCAGGCCGAAGCAGCGTTGTTGCAGTGCACGGCAGATACACTTGCT
GATGCGGTGCTGATTACGACCGCTCACGCGTGGCAGCATCAGGGGAAAACCTTATTTATCAGCCGG
AAAACCTACCGGATTGATGGTAGTGGTCAAATGGCGATTACCGTTGATGTTGAAGTGGCGAGCGAT
ACACCGCATCCGGCGCGGATTGGCCTGAACTGCCAGCTGGCGCAGGTAGCAGAGCGGGTAAACTGG
CTCGGATTAGGGCCGCAAGAAAACTATCCCGACCGCCTACTGCCGCCTGTTTTGACCGCTGGGAT
CTGCCATTGTCAGACATGTATACCCCGTACGTCTTCCCGAGCGAAAACGGTCTGCGCTGCGGGACG
CGCGAATTGAATTATGGCCCACACCAGTGGCGCGGCGACTTCCAGTTCAACATCAGCCGCTACAGT
CAACAGCAACTGATGGAAACCAGCCATCGCCATCTGCTGCACGCGGAAGAAGGCACATGGCTGAAT
ATCGACGGTTTCCATATGGGGATTGGTGGCGACGACTCCTGGAGCCCGTCAGTATCGGCGGAATTC
AGCTGAGCGCCGGTCGCTACCATTACCAGTTGGTCTGGTGTCAAAAATAATAATAACCGGGCAGGG
GGGATCCTTCTGTGAGCGTATGGCAAACGAAGGAAAAATAGTTATAGTAGCCGCACTCGATGGGAC
ATTTCAACGTAAACCGTTTAATAATATTTTGAATCTTATTCCATTATCTGAAATGGTGGTAAAACT
AACTGCTGTGTGTATGAAATGCTTTAAGGAGGCTTCCTTTTCTAAACGATTGGGTGAGGAAACCGA
GATAGAAATAATAGGAGGTAATGATATGTATCAATCGGTGTGTAGAAAGTGTTACATCGACTCATA
ATATTATATTTTTTATCTAAAAAACTAAAAATAAACATTGATTAAATTTTAATATAATACTTAAAA
ATGGATGTTGTGTCGTTAGATAAACCGTTTATGTATTTTGAGGAAATTGATAATGAGTTAGATTAC
GAACCAGAAAGTGCAAATGAGGTCGCAAAAAAACTGCCGTATCAAGGACAGTTAAAACTATTACTA
GGAGAATTATTTTTTCTTAGTAAGTTACAGCGACACGGTATATTAGATGGTGCCACCGTAGTGTAT
ATAGGATCTGCTCCCGGTACACATATACGTTATTTGAGAGATCATTTCTATAATTTAGGAGTGATC
ATCAAATGGATGCTAATTGACGGCCGCCATCATGATCCTATTTTAAATGGATTGCGTGATGTGACT
CTAGTGACTCGGTTCGTTGATGAGGAATATCTACGATCCATCAAAAAACAACTGCATCCTTCTAAG
ATTATTTTAATTTCTGATGTGAGATCCAAACGAGGAGGAAATGAACCTAGTACGGCGGATTTACTA
AGTAATTACGCTCTACAAAATGTCATGATTAGTATTTTAAACCCCGTGGCGTCTAGTCTTAAATGG
AGATGCCCGTTTCCAGATCAATGGATCAAGGACTTTTATATCCCACACGGTAATAAAATGTTACAA
CCTTTTGCTCCTTCATATTCAGCTGAAATGAGATTATTAAGTATTTATACCGGTGAGAACATGAGA
CTGACTCGGGCCGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCGTTTCCCCCTGGA
AGCTCCCTCGTGCGCTCTCCTGTTCCGACCCTGCCGCTTACCGGATACCTGTCCGCCTTTCTCCCT
TCGGGAAGCGTGGCGCTTTCTCAATGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATT
AGCAGAGCGAGGTATGTAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGAAAAGAGTTGGTAGC
TCTTGATCCGGCAAACAAACCACCGCTGGTAGCGGTGGTTTTTTGTTTGCAAGCAGCAGATTACG
CGCAGAAAAAAGGATCTCAAGAAGATCCTTTGATCTTTTCTACGGGGTCTGACGCTCAGTGGAAC
GAAAACTCACGTTAAGGGATTTTGGTCATGAGATTATCAAAAGGATCTTCACCTAGATCCTTTTA
AATTAAAAATGAAGTTTTAAATCAATCTAAAGTATATATGAGTAAACTTGGTCTGACAGTTACCAA
TGCTTAATCAGTGAGGCACCTATCTCAGCGATCTGTCTATTTCGTTCATCCATAGTTGCCTGACTC
CCCGTCGTGTAGATAACTACGATACGGGAGGGCTTACCATCTGGCCCCAGTGCTGCAATGATACCG
CGAGACCCACGCTCACCGGCTCCAGATTTATCAGCAATAAACCAGCCAGCCGGAAGGGCCGAGCGC
```

FIG. 37 CONT'D

```
AGAAGTGGTCCTGCAACTTTATCCGCCTCCATCCAGTCTATTAATTGTTGCCGGGAAGCTAGAGTA
AGTAGTTCGCCAGTTAATAGTTTGCGCAACGTTGTTGCCATTGCTGCAGGCATCGTGGTGTCACGC
TCGTCGTTTGGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAGTTGGCCGCA
GTGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTGC
TCTTGCCCGGCGTCAACACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATACATATTTGAA
TGTATTTAGAAAAATAAACAAATAGGGGTTCCGCGCACATTTCCCCGAAAAGTGCCACCTGACGTC
TAAGAAACCATTATTATCATGACATTAACCTATAAAAATAGGCGTATCACGAGGCCCTTTCGTCTT
CGAATAAATACCTGTGACGGAAGATCACTTCGCAGAATAAATAAATCCTGGTGTCCCTGTTGATAC
CGGGAAGCCCTGGGCCAACTTTTGGCGAAAATGAGACGTTGATCGGCACGTAAGAGGTTCCAACTT
TCACCATAATGAAATAAGATCACTACCGGGCGTATTTTTTGAGTTATCGAGATTTTCAGGAGCTAA
GGAAGCTAAAATGGAGAAAAAAATCACTGGATATACCACCGTTGATATATCCCAATGGCATCGTAA
AGAACATTTTGAGGCATTTCAGTCAGTTGCTCAATGTACCTATAACCAGACCGTTCAG
```

FIG. 37 CONT'D

```
CCTCCTGAAAAACTGGAATTTAATACACCATTTGTGTTCATCATCAGACATGATATTACTGGATTT
ATATTGTTTATGGGTAAGGTAGAATCTCCTTAATATGGGTACGGTGTAAGGAATCATTATTTTATT
TATATTGATGGGTACGTGAAATCTGAATTTTCTTAATAAATATTATTTTTATTAAATGTGTATATG
TTGTTTTGCGATAGCCATGTATCTACTAATCAGATCTATTAGAGATATTATTAATTCTGGTGCAAT
ATGACAAAAATTATACACTAATTAGCGTCTCGTTTCAGACATGGATCTGTCACGAATTAATACTTG
GAAGTCTAAGCAGCTGAAAAGCTTTCTCTCTAGCAAAGATGCATTTAAGGCGGATGTCCATGGACA
TAGTGCCTTGTATTATGCAATAGCTGATAATAACGTGCGTCTAGTATGTACGTTGTTGAACGCTGG
AGCATTGAAAAATCTTCTAGAGAATGAATTTCCATTACATCAGGCAGCCACATTGGAAGATACCAA
AATAGTAAAGATTTTGGCTATTCAGTGGACTGGATGATTCGAGGTACCCGATCCCCCCTGCCCGGT
TATTATTATTTTTGACACCAGACCAACTGGTAATGGTAGCGACCGGCGCTCAGCTGAATTCCGCCG
ATACTGACGGGCTCCAGGAGTCGTCGCCACCAATCCCCATATGGAAACCGTCGATATTCAGCCATG
TGCCTTCTTCCGCGTGCAGCAGATGGCGATGGCTGGTTTCCATCAGTTGCTGTTGACTGTAGCGGC
TGATGTTGAACTGGAAGTCGCCGCGCCACTGGTGTGGGCCATAATTCAATTCGCGCGTCCCGCAGC
GCAGACCGTTTTCGCTCGGGAAGACGTACGGGTATACATGTCTGACAATGGCAGATCCCAGCGGT
CAAAACAGGCGGCAGTAAGGCGGTCGGGATAGTTTTCTTGCGGCCCTAATCCGAGCCAGTTTACCC
GCTCTGCTACCTGCGCCAGCTGGCAGTTCAGGCCAATCCGCGCCGGATGCGGTGTATCGCTCGCCA
CTTCAACATCAACGGTAATCGCCATTTGACCACTACCATCAATCCGGTAGGTTTTCCGGCTGATAA
ATAAGGTTTTCCCCTGATGCTGCCACGCGTGAGCGGTCGTAATCAGCACCGCATCAGCAAGTGTAT
CTGCCGTGCACTGCAACAACGCTGCTTCGGCCTGGTAATGGCCCGCCGCCTTCCAGCGTTCGACCC
AGGCGTTAGGGTCAATGCGGGTCGCTTCACTTACGCCAATGTCGTTATCCAGCGGTGCACGGGTGA
ACTGATCGCGCAGCGGCGTCAGCAGTTGTTTTTTATCGCCAATCCACATCTGTGAAAGAAAGCCTG
ACTGGCGGTTAAATTGCCAACGCTTATTACCCAGCTCGATGCAAAAATCCATTTCGCTGGTGGTCA
GATGCGGGATGGCGTGGGACGCGGCGGGGAGCGTCACACTGAGGTTTTCCGCCAGACGCCACTGCT
GCCAGGCGCTGATGTGCCCGGCTTCTGACCATGCGGTCGCGTTCGGTTGCACTACGCGTACTGTGA
GCCAGAGTTGCCCGGCGCTCTCCGGCTGCGGTAGTTCAGGCAGTTCAATCAACTGTTTACCTTGTG
GAGCGACATCCAGAGGCACTTCACCGCTTGCCAGCGGCTTACCATCCAGCGCCACCATCCAGTGCA
GGAGCTCGTTATCGCTATGACGGAACAGGTATTCGCTGGTCACTTCGATGGTTTGCCCGGATAAAC
GGAACTGGAAAAACTGCTGCTGGTGTTTTGCTTCCGTCAGCGCTGGATGCGGCGTGCGGTCGGCAA
AGACCAGACCGTTCATACAGAACTGGCGATCGTTCGGCGTATCGCCAAAATCACCGCCGTAAGCCG
ACCACGGGTTGCCGTTTTCATCATATTTAATCAGCGACTGATCCACCCAGTCCCAGACGAAGCCGC
CCTGTAAACGGGGATACTGACGAAACGCCTGCCAGTATTTAGCGAAACCGCCAAGACTGTTACCCA
TCGCGTGGGCGTATTCGCAAAGGATCAGCGGGCGCGTCTCTCCAGGTAGCGAAAGCCATTTTTTGA
TGGACCATTTCGGCACAGCCGGGAAGGGCTGGTCTTCATCCACGCGCGCGTACATCGGGCAAATAA
TATCGGTGGCCGTGGTGTCGGCTCCGCCGCCTTCATACTGCACCGGGCGGGAAGGATCGACAGATT
TGATCCAGCGATACAGCGCGTCGTGATTAGCGCCGTGGCCTGATTCATTCCCCAGCGACCAGATGA
TCACACTCGGGTGATTACGATCGCGCTGCACCATTCGCGTTACGCGTTCGCTCATCGCCGGTAGCC
AGCGCGGATCATCGGTCAGACGATTCATTGGCACCATGCCGTGGGTTTCAATATTGGCTTCATCCA
CCACATACAGGCCGTAGCGGTCGCACAGCGTGTACCACAGCGGATGGTTCGGATAATGCAACAGC
GCACGGCGTTAAAGTTGTTCTGCTTCATCAGCAGGATATCCTGCACCATCGTCTGCTCATCCATGA
CCTGACCATGCAGAGGATGATGCTCGTGACGGTTAACGCCTCGAATCAGCAACGGCTTGCCGTTCA
GCAGCAGCAGACCATTTTCAATCCGCACCTCGCGGAAACCGACATCGCAGGCTTCTGCTTCAATCA
GCGTGCCGTCGGCGGTGTGCAGTTCAACCACCGCACGATAGAGATTCGGGATTTCGGCGCTCCACA
GTTTCGGGTTTTCGACGTTGAGACGTAGTGTGACGCGATCGGCATAACCACCACGCTCATCGATAA
TTTCACCGCCGAAAGGCGCGGTGCCGCTGGCGACCTGCGTTTCACCCTGCCATAAAGAAACTGTTA
```

FIG. 38

```
GCAGCACCATCACCGCGAGGCGGTTTTCTCCGGCGCGTAAAAATGCGCTCAGGTCAAATTCAGACG
GCAAACGACTGTCCTGGCCGTAACCGACCCAGCGCCCGTTGCACCACAGATGAAACGCCGAGTTAA
CGCCATCAAAAATAATTCGCGTCTGGCCTTCCTGTAGCCAGCTTTCATCAACATTAAATGTGAGCG
AGTAACAACCCGTCGGATTCTCCGTGGGAACAAACGGCGGATTGACCGTAATGGGATAGGTTACGT
TGGTGTAGATGGGCGCATCGTAACCGTGCATCTGCCAGTTTGAGGGGACGACGACAGTATCGGCCT
CAGGAAGATCGCACTCCAGCCAGCTTTCCGGCACCGCTTCTGGTGCCGGAAACCAGGCAAAGCGCC
ATTCGCCATTCAGGCTGCGCAACTGTTGGGAAGGGCGATCGGTGCGGGCCTCTTCGCTATTACGCC
AGCTGGCGAAAGGGGGATGTGCTGCAAGGCGATTAAGTTGGGTAACGCCAGGGTTTTCCCAGTCAC
GACGTTGTAAAACGACGGGATCTCCCATGCTCGAGTTATGATCTACTTCCTTACCGTGCAATAAAT
TAGAATATATTTTCTACTTTTACGAGAAATTAATTATTGTATTTATTATTTATGGGTGAAAAACTT
ACTATAAAAAGCGGGTGGGTTTGGAATTAGTGAAAGCTGGGAGATCTGGCGCGCCTGCAGAGAATT
CGTTTAAACGGATCCCGAGCTTATTTATATTCCAAAAAAAAAAAATAAAATTTCAATTTTTAAGCT
GGGGATCCTCTAGAGTCGACCTGCAGGCATGCTCGAGCGGCCGCCAGTGTGATGGATATCTGCAGA
ATTCGGCTTGGGGGCTGCAGGTGGATGCGATCATGACGTCCTCTGCAATGGATAACAATGAACCT
AAAGTACTAGAAATGGTATATGATGCTACAATTTTACCCGAAGGTAGTAGCATGGATTGTATAAAC
AGACACATCAATATGTGTATACAACGCACCTATAGTTCTAGTATAATTGCCATATTGGATAGATTC
CTAATGATGAACAAGGATGAACTAAATAATACACAGTGTCATATAATTAAAGAATTTATGACATAC
GAACAAATGGCGATTGACCATTATGGAGAATATGTAAACGCTATTCTATATCAAATTCGTAAAAGA
CCTAATCAACATCACACCATTAATCTGTTTAAAAAAATAAAAAGAACCCGGTATGACACTTTTAAA
GTGGATCCCGTAGAATTCGTAAAAAAGTTATCGGATTTGTATCTATCTTGAACAAATATAAACCG
GTTTATAGTTACGTCCTGTACGAGAACGTCCTGTACGATGAGTTCAAATGTTTCATTGACTACGTG
GAAACTAAGTATTTCTAAAATTAATGATGCATTAATTTTGTATTGATTCTCAATCCTAAAAACTA
AAATATGAATAAGTATTAAACATAGCGGTGTACTAATTGATTTAACATAAAAAATAGTTGTTAACT
AATCATGAGGACTCTACTTATTAGATATATTCTTTGGAGAAATGACAACGATCAAACCGGGCATGC
AAGCTTGTCTCCCTATAGTGAGTCGTATTAGAGCTTGGCGTAATCATGGTCATAGCTGTTTCCTGT
GTGAAATTGTTATCCGCTCACAATTCCACACAACATACGAGCCGGAAGCATAAAGTGTAAAGCCTG
GGGTGCCTAATGAGTGAGCTAACTCACATTAATTGCGTTGCGCTCACTGCCCGCTTTCGAGTCGGG
AAACCTGTCGTGCCAGCTGCATTAATGAATCGGCCAACGCGCGGGGAGAGGCGGTTTGCGTATTGG
GCGCTCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCGATAGGCT
CCGCCCCCTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTAG
GTATCTCAGTTCGGTGTAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCTGCTGAAGCC
AGTTACCTTCGGAAAAAGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTAAAGTATATA
TGAGTAAACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGATTTATCAGCAAT
AAACCAGCCAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACGTTGTTGG
CATTGCTACAGGCATCGTGGTGTCACGCTCGTCGTTTGGTATGGCTTCATTCAGCTCCGGTTCCCA
```

FIG. 38 CONT'D

```
ACGATCAAGGCGAGTTACATGATCCCCCATGTTGTGCAAAAAAGCGGTTAGCTCCTTCGGTCCTCC
GATCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTCTG
AGAATAGTGTATGCGGCGACCGAGTTGCTCTTGCCCGGCGTCAATACGGGATAATACCGCGCCACA
TAGCAGAACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCATCTTTTAC
TTTCACCAGCGTTTCTGGGTGAGCAAAAACAGGAAGGCAAAATGCCGCAAAAAAGGGAATAAGGGC
GACACGGAAATGTTGAATACTCATACTCTTCCTTTTTCAATATTATTGAAGCATTTATCAGGGTTA
TTGTCTCATGAGCGGATACATATTTGAATGTATTTAGAAAAATAAACAAATAGGGGTTCCGCGCAC
ATTTCCCCGAAAAGTGCCACCTGACGTCTAAGAAACCATTATTATCATGACATTAACCTATAAAAA
TAGGCGTATCACGAGGCCCTTTCGTCTCGCGCGTTTCGGTGATGACGGTGAAAACCTCTGACACAT
GCAGCTCCCGGAGACGGTCACAGCTTGTCTGTAAGCGGATGCCGGGAGCAGACAAGCCCGTCAGGG
CGCGTCAGCGGGTGTTGGCGGGTGTCGGGGCTGGCTTAACTATGCGGCATCAGAGCAGATTGTACT
GAGAGTGCACCATATGCGGTGTGAAATACCGCACAGATGCGTAAGGAGAAAATACCGCATCAGGCG
CCATTCGCCATTCAGGCTGCGCAACTGTTGGGAAGGGCGATCGGTGCGGGCCTCTTCGCTATTACG
CCAGCTGGCGAAAGGGGGATGTGCTGCAAGGCGATTAAGTTGGGTAACGCCAGGGTTTTCCCAGTC
ACGACGTTGTAAAACGACGGCCAGTGAATTGGATTTAGGTGACACTATAGAATACGAATTC
```

FIG. 38 CONT'D

EQUINE INFECTIOUS ANEMIA VIRUS VECTORS

This application is a Continuing Application of PCT/GB98/03876, filed Dec. 22, 1998, claiming priority to United Kingdom Application No. 9727135.7, filed Dec. 22, 1997 and United Kingdom Application No. 9811037.2, filed May 22, 1998.

STATEMENT REGARDING FEDERALLY SPONSORED RESEARCH AND DEVELOPMENT

Not applicable.

FIELD OF INVENTION

This invention relates to a retroviral vector. In particular, but not exclusively, it relates to retroviral vectors capable of transferring genetic material to non-dividing or slowly-dividing cells derived from non-primate lentiviruses.

BACKGROUND OF THE INVENTION

There has been considerable interest, for some time, in the development of retroviral vector systems based on lentiviruses, a small subgroup of the retroviruses. This interest arises firstly from the notion of using HIV-based vectors to target anti-HIV therapeutic genes to HIV susceptible cells and secondly from the prediction that, because lentiviruses are able to infect non-dividing cells (Lewis & Emerman 1993 J.Virol. 68, 510), vector systems based on these viruses would be able to transduce non-dividing cells (e.g. Vile & Russel 1995 Brit. Med. Bull. 51, 12). Vector systems based on HIV have been produced (Buchschacher & Panganiban 1992 J.Virol. 66, 2731) and they have been used to transduce CD4+ cells and, as anticipated, non-dividing cells (Naldini et al, 1996 Science 272, 263). In addition lentiviral vectors enable very stable long-term expression of the gene of interest. This has been shown to be at least three months for transduced rat neuronal cells. The MLV based vectors were only able to express the gene of interest for six weeks.

HIV-based vectors produced to date result in an integrated provirus in the transduced cell that has HIV LTRs at its ends. This limits the use of these vectors as the LTRs have to be used as expression signals for any inserted gene unless an internal promoter is used. The use of internal promoters has significant disadvantages. The unpredictable outcome of placing additional promoters within the retroviral LTR transcription unit is well documented (Bowtell et al, 1988 J.Virol. 62, 2464; Correll et al, 1994 Blood 84, 1812; Emerman and Temin 1984 Cell 39, 459; Ghattas et al, 1991 Mol.Cell.Biol. 11, 5848; Hantzopoulos et al, 1989 PNAS 86, 3519; Hatzoglou et al, 1991 J.Biol.Chem 266, 8416; Hatzoglou et al, 1988 J.Biol.Chem 263, 17798; Li et al, 1992 Hum.Gen.Ther. 3, 381; McLachlin et al, 1993 Virol. 195, 1; Overell et al, 1988 Mol.Cell Biol. 8, 1803; Scharfman et al, 1991 PNAS 88, 4626; Vile et al, 1994 Gene Ther 1, 307; Xu et al, 1989 Virol. 171, 331; Yee et al, 1987 PNAS 84, 5197). The factors involved appear to include the relative position and orientation of the two promoters, the nature of the promoters and the expressed genes and any selection procedures that may be adopted. The presence of internal promoters can affect both the transduction titers attainable from a packaging cell line and the stability of the integrated vector.

HIV and other lentiviral LTRs have virus-specific requirements for gene expression. For example, the HIV LTR is not active in the: absence of the viral Tat protein (Cullen 1995 AIDS 9, S19). It is desirable, therefore, to modify the LTRs in such a way as to change the requirements for gene expression. In particular tissue specific gene expression signals may be required for some gene therapy applications.

HIV vectors have a number of significant disadvantages which may limit their therapeutic application to certain diseases. HIV-1 has the disadvantage of being a human pathogen carrying potentially oncogenic proteins and sequences. There is the risk that introduction of vector particles produced in packaging cells which express HIV gag-pol will introduce these proteins into the patient leading to seroconversion. For these reasons, there is a need to develop lentiviral-based vectors which do not introduce HIV proteins into patients.

SUMMARY OF THE INVENTION

We have now found it possible to provide an improved lentiviral vector which overcomes the limitations of HIV-based vectors. It is important in the development of any retroviral vector system to remove sequences from the retroviral genome which may inhibit the capacity of the vector to transfer heterologous genes or which may transfer disadavantageous protein coding sequences to the target cell. Retroviruses are limited in the length of RNA sequences which can be packaged efficiently and so the existence of long regions of the retroviral genome severely limits the coding capacity of the vector for heterologous coding RNA.

We have also found it possible to provide a lentiviral vector based on a non-primate lentivirus which has a high coding capacity for heterologous coding sequences and which has a reduced capacity to transfer retroviral components to the target cell.

It has surprisingly been found that the amount of vector genomic sequence required from a non-primate lentivirus to produce an efficient cloning vector is substantially less than has been described for an HIV-based vector.

The sequence requirements for packaging HIV vector genomes are complex. The HIV-1 packaging signal encompasses the splice donor site and contains a portion of the 5'-untranslated region of the gag gene which has a putative secondary structure containing 4 short stem-loops. Additional sequences elsewhere in the genome are also known to be important for efficient encapsidation of HIV. For example the first 350 bps of the gag protein coding sequence may contribute to efficient packaging and ill defined regions of env are also implicated. For the construction of HIV-vectors capable of expressing heterologous genes, a packaging signal extending to 350 bps of the gag protein-coding region has been used.

We have surprisingly found that the structure of the packaging signal in non-primate lentiviruses is entirely different from that of HIV. Instead of a short sequence of 4 stem loops followed by an ill defined region of gag and env sequences, we have discovered that a shorter region of the gag gene suffices for efficient packaging. Indeed deletion of larger regions of the gag gene in EIAV vectors is advantageous and leads to higher titre viral vector being produced. This information can be used to provide improved vectors constructed from non-primate lentivirus sequences which have high titre and advantageous features compared to HIV vectors.

In a first aspect of the invention, there is provided a retroviral vector genome containing a deleted gag gene from a non-primate lentivirus wherein the deletion in gag removes one or more nucleotides downstream of nucleotide 350 of the gag coding sequence. Preferably the deletion extends from nucleotide 350 to at least the C-terminus of the gagpol coding region. More preferably the deletion additionally removes nucleotide 300 of the gag coding region and most preferably the deletion retains only the first 150 nucleotides of the gag coding region. However even larger deletions of gag can also be used, for example the gag coding region contains the first 109 nucleotides of the gag coding region. It may also be possible for the gag coding region to contain only the first 2 nucleotides of the gag coding region.

Additional features of the lentiviral genome are included in the vector genome which are necessary for transduction of the target cell; replication; reverse transcription and integration. These are, at least, a portion of an LTR containing sequence from the R-region and U5 region, sequences from the 3' LTR which contain a polypurine tract (PPT) and a 3' LTR from the non-primate lentivirus or a hybrid LTR containing sequences from the non-primate lentivirus and other elements. Optionally, the retroviral genome may contain accessory genes derived from a retrovirus, such as, but not limited to, a rev gene, a tat gene, a vif gene, a nef gene, a vpr gene or an S2 gene. Additional components may be added such as introns, splice-donor sites, a rev responsive element (RRE), cloning sites and selectable marker genes.

Moreover, we have now surprisingly demonstrated that a non-primate lentivirus minimal vector system can be constructed which requires neither S2, Tat, env nor dUTPase for either vector production or for transduction of dividing and non-dividing cells.

Thus according to another aspect the non-primate lentivirus genome from which the vector is derived lacks one or more accessory genes.

The deletion of accessory genes is highly advantageous. Firstly, it permits vectors to be produced without the genes normally associated with disease in lentiviral (e.g. HIV) infections. In particular, tat and env are associated with disease. Secondly, the deletion of accessory genes permits the vector to package more heterologous DNA. Thirdly, genes whose function is unknown, such as dUTPase and S2, may be omitted, thus reducing the risk of causing undesired effects.

In addition, we have shown that the leader sequence of the non-primate lentivirus genome is essential for high protein expression of gag and gagpol.

Therefore in a further aspect the non-primate lentivirus genome from which the vector is derived lacks the tat gene but includes the leader sequence between the end of the 5' LTR and the ATG of gag.

These data further define a minimal essential set of functional components for an optimal lentiviral vector. A vector is provided with maximal genetic capacity and high titre, but without accessory genes that are either of unknown function (S2, UTPase), and therefore may present risk, or are analogues of HIV proteins that may be associated with AIDS (tat, env).

BRIEF DESCRIPTION OF THE DRAWING

FIG. 1 shows the structure of transcription units from plasmids pESP, pONY3 and pONY2.1nlsLacZ. The genomic organization of EIAV is indicated including splice donor (d1, d2 and d3) and splice acceptor sites (a1, a2 and a3). The positions of gag, pol, env, tat, rev, S2 and the viral LTRs are also shown. Plasmid pESP is an EIAV vector genome containing the SV40 promoter and the puromycin resistance gene. Plasmid pONY3 is an EIAV gagpol expression plasmid. pONY21nlslacZ is an EIAV vector genome containing a HCMV IE enhancer/promoter and a β-galactosidase gene (nlslacZ).

FIG. 2 shows a PCR analysis of integrated EIAV vector. PCR was performed with either genomic DNA from EIAV vector transduced cells (lanes 1 and 5) or mock transduced cells (lanes 2 and 6). pONY21nlsLacZ (lanes 3 and 7) and pONY3 (lanes 4 and 8) were used as controls. A) PCR detection of EIAV LTR. B) PCR detection of pol.

FIG. 4 shows a secondary structure prediction for the RNA derived from the gag-transcription unit (SEQ ID NO: 1) present in pONY2.13LacZ.

FIG. 18 shows primers for construction of MLV/EIAV vectors (SEQ ID NOs: 6–13).

FIGS. 19A and 19B show the complete sequence of pONYmouse (SEQ ID NO: 14).

FIGS. 20 and 21 give sequences of PCR primers EMVA 1–8 (SEQ ID NOs: 15–22).

FIGS. 25 and 26 show an example of hammer-head strategy for 5' end formation (SEQ ID NOs: 23 and 24).

FIGS. 37 show the complete sequence of pSC65 (SEQ ID NO: 27).

FIGS. 38 show the complete sequence of pLW22 (SEQ ID NO: 28).

DETAILED DESCRIPTION OF THE INVENTION

Figure 3:
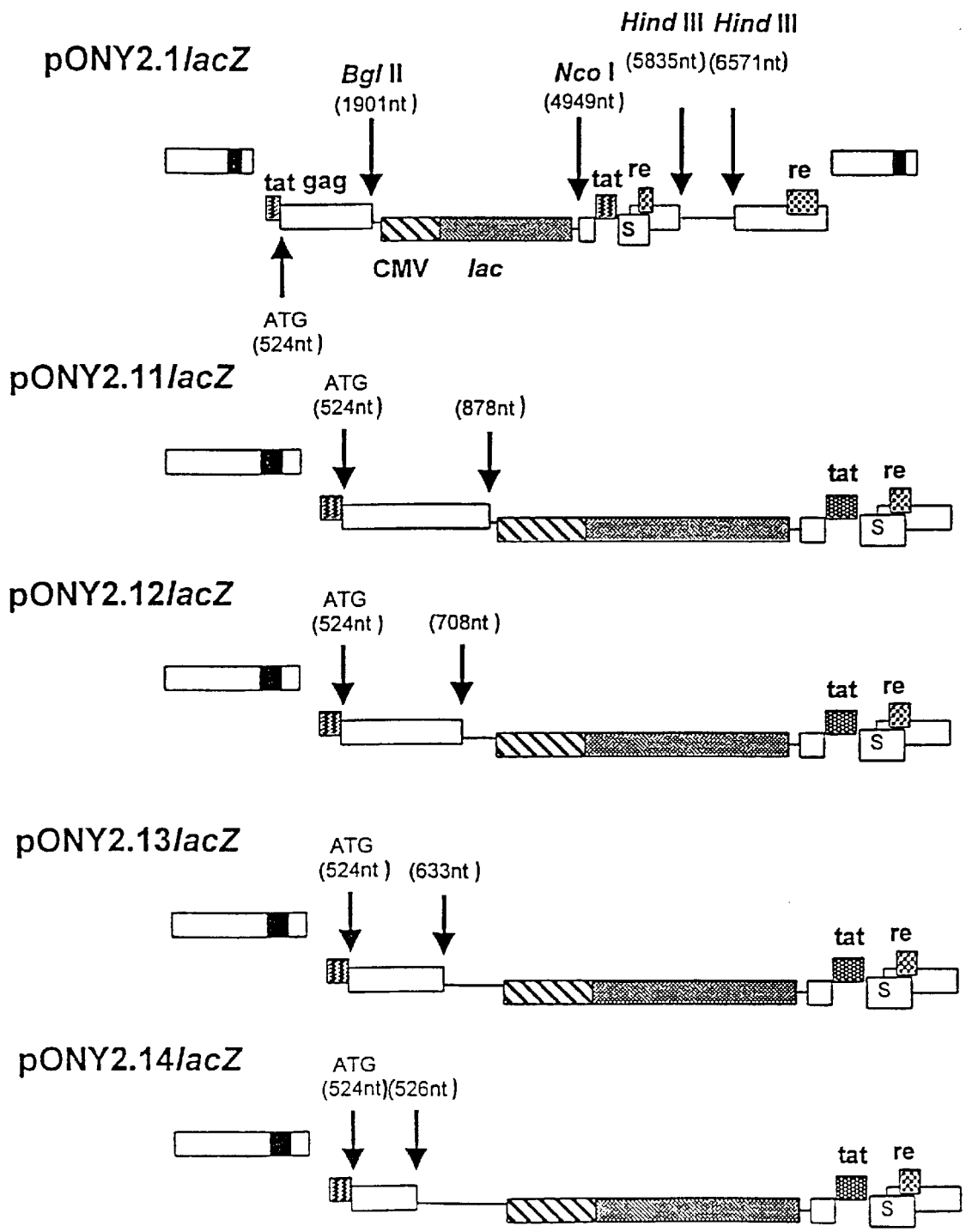
FIG. 3 shows the structure of vector transcription units in deletion plasmids used to identify the packaging requirements for an EIAV vector.
Figure 5:
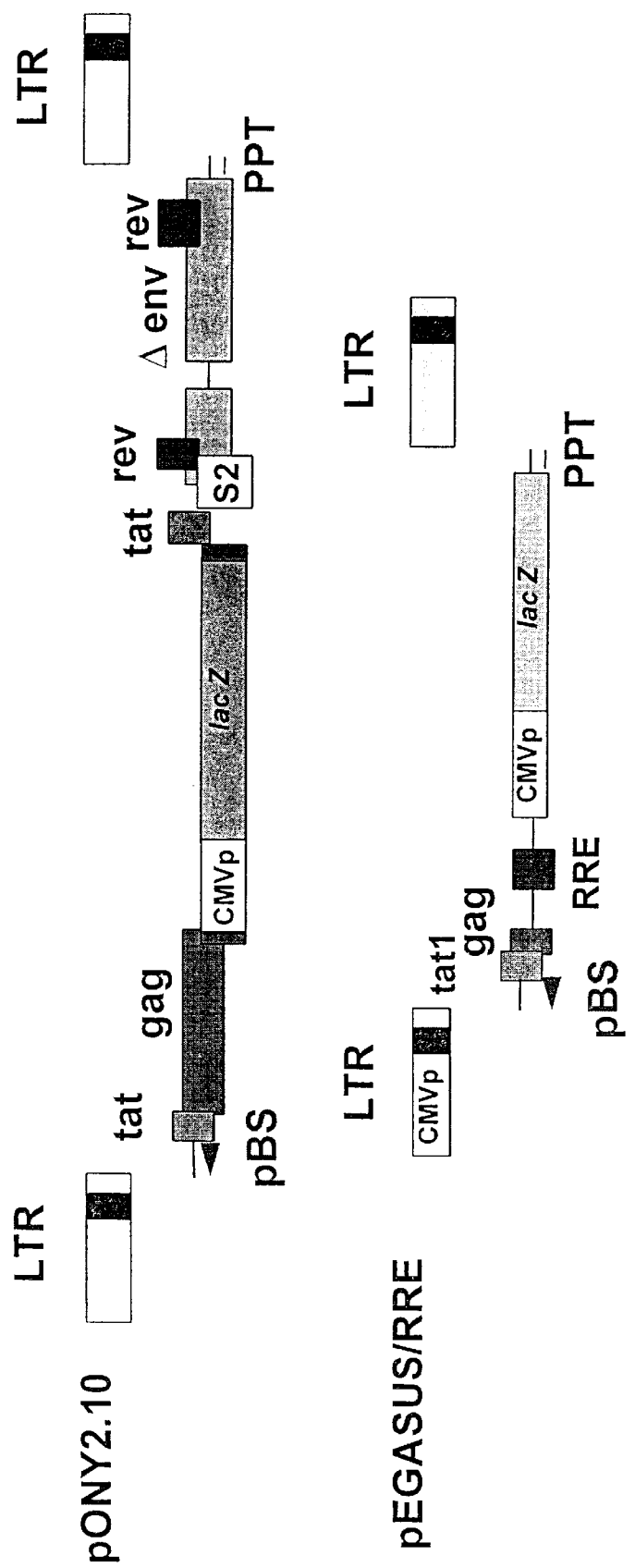
FIG. 5 is a representation of vectors derived from the EIAV genome.
Figure 6:
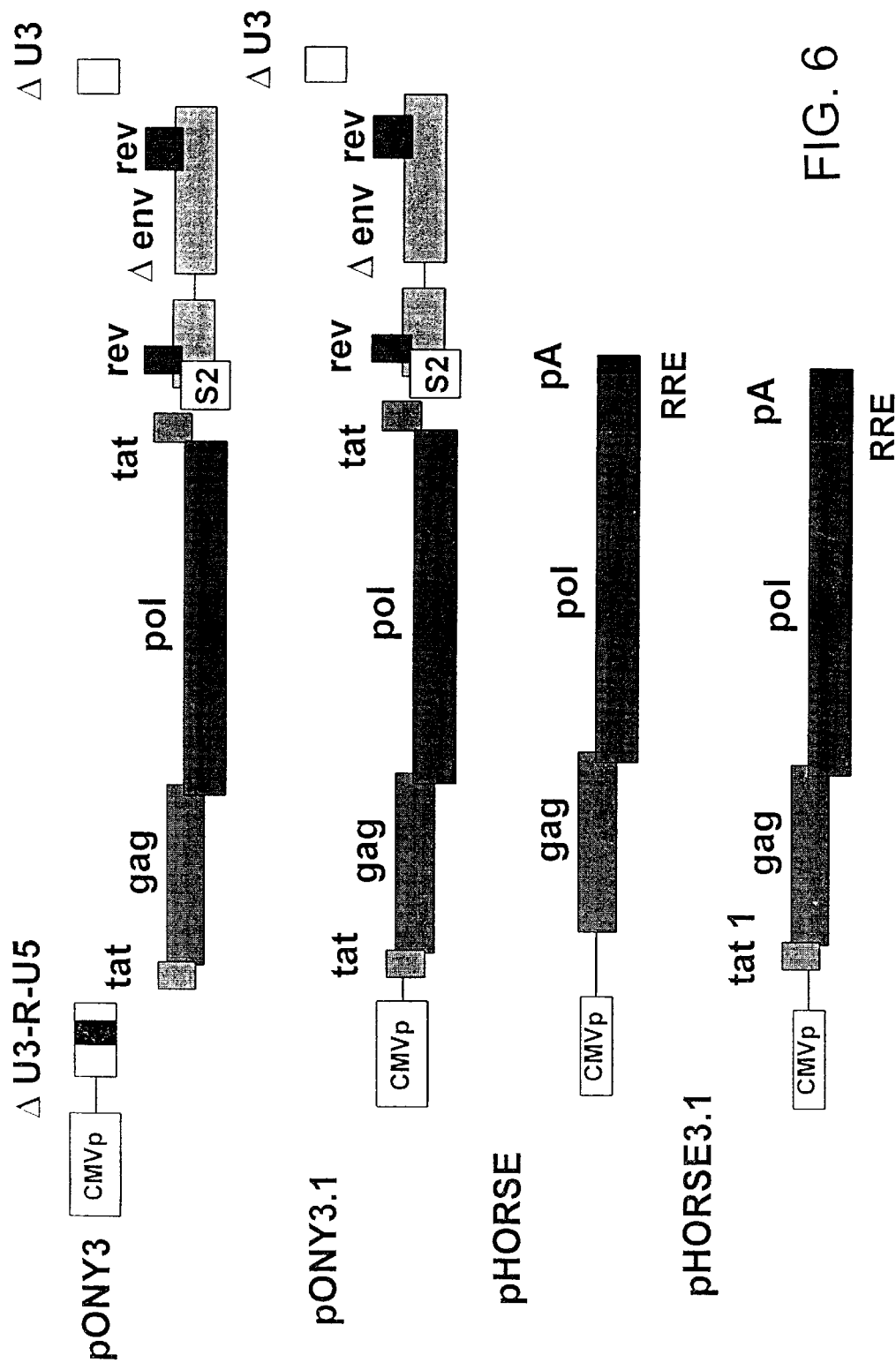
FIG. 6 is a representation of gagpol constructs derived from EIAV.
Figure 7:
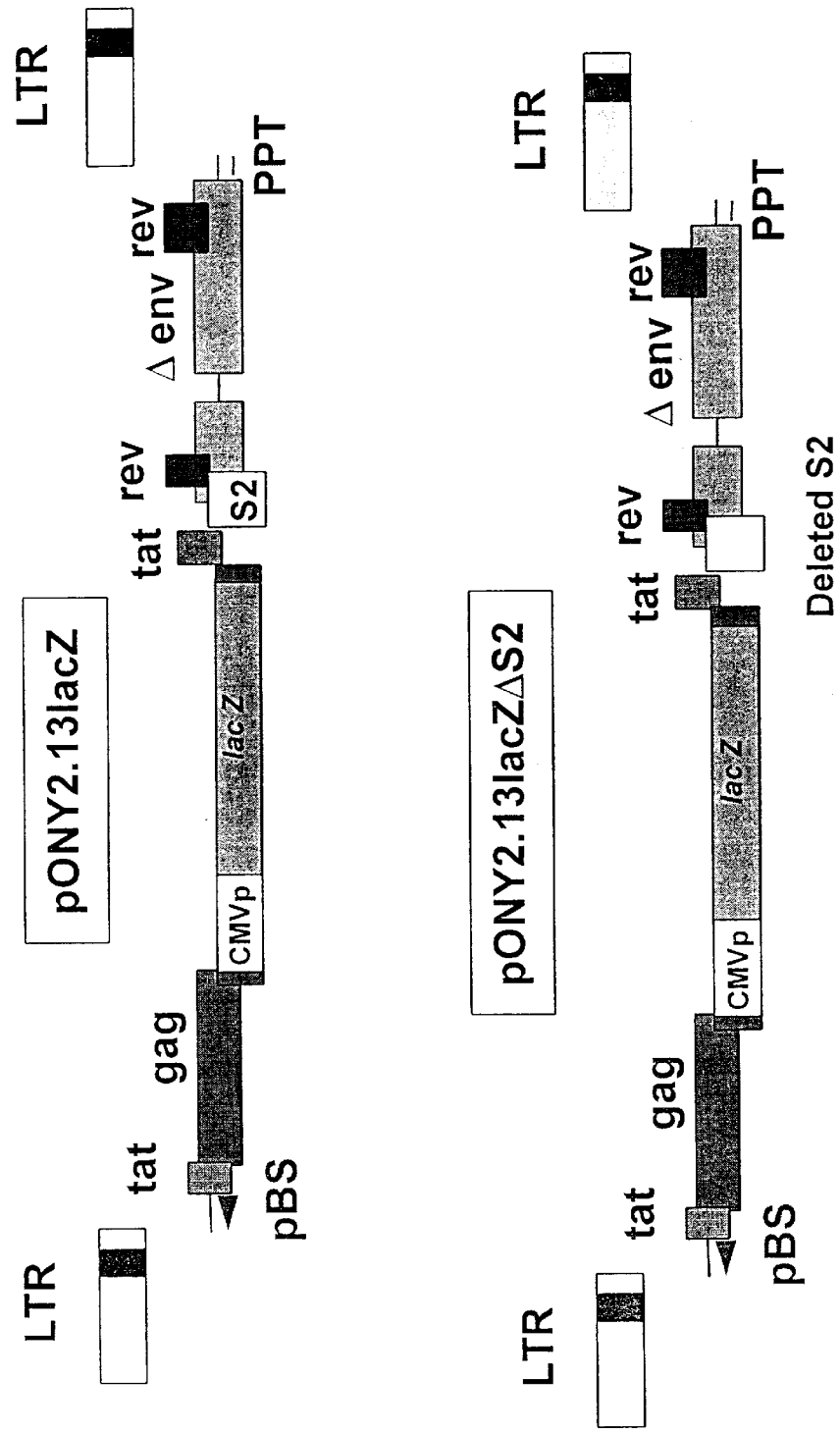
FIG. 7 is a representation of an EIAV vector comprising an S2 deletion.
Figure 8:
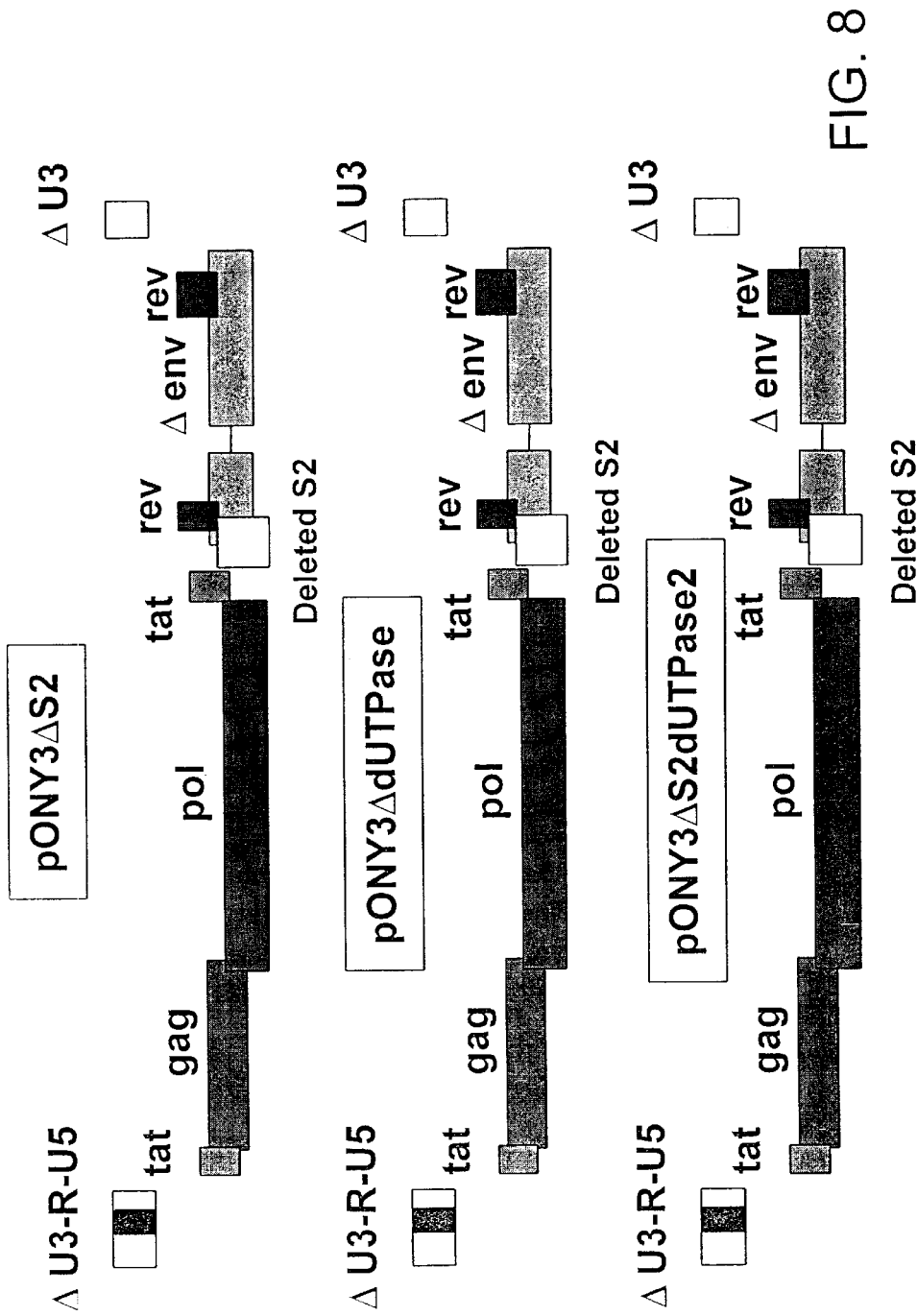
FIG. 8 is a representation of EIAV gagpol constructs having deleted S2 and dUTPase genes.
Figure 9:
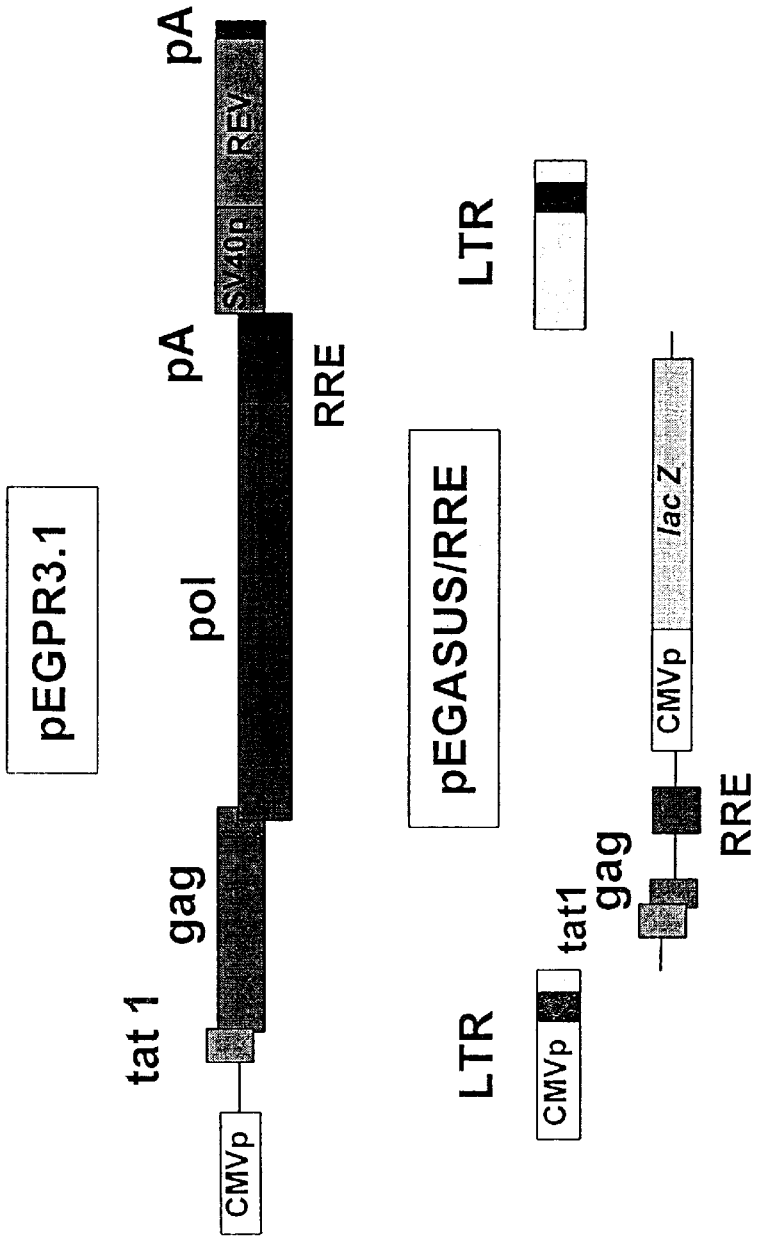
FIG. 9 is a representation of an EIAV minimal vector.

It will be appreciated that the present invention provides a retroviral vector derived from a non-primate lentivirus genome (1) comprising a deleted gag gene wherein the deletion in gag removes one or more nucleotides downstream of nucleotide 350 of the gag coding sequence; (2) wherein one or more accessory genes are absent from the non-primate lentivirus genome; (3) wherein the non-primate lentivirus genome lacks the tat gene but includes the leader sequence between the end of the 5' LTR and the ATG of gag; and combinations of (1), (2) and (3). In a preferred embodiment the retroviral vector comprises all of features (1) and (2) and (3).

A "non-primate" vector, as used herein, refers to a vector derived from a virus which does not primarily infect primates, especially humans. Thus, non-primate virus vectors include vectors which infect non-primate mammals, such as dogs, sheep and horses, reptiles, birds and insects.

A lentiviral or lentivirus vector, as used, herein, is a vector which comprises at least one component part derived from a lentivirus. Preferably, that component part is involved in the biological mechanisms by which the vector infects cells, expresses genes or is replicated.

The non-primate lentivirus may be any member of the family of lentiviridae which does not naturally infect a primate and may include a feline immunodeficiency virus (FIV), a bovine immunodeficiency virus (BIV), a caprine arthritis encephalitis virus (CAEV), a Maedi visna virus (MVV) or an equine infectious anaemia virus (EIAV). Preferably the lentivirus is an EIAV. Equine infectious anaemia virus infects all equidae resulting in plasma viremia and thrombocytopenia (Clabough, et al. 1991. J. Virol. 65:6242–51). Virus replication is thought to be controlled by the process of maturation of monocytes into macrophages.

EIAV has the simplest genomic structure of the lentiviruses. In addition to the gag, pol and env genes EIAV encodes three other genes: tat, rev, and S2. Tat acts as a transcriptional activator of the viral LTR (Derse and Newbold1993 Virology. 194:530–6; Maury, et al 1994 Virology. 200:632–42.) and Rev regulates and coordinates the expression of viral genes through rev-response elements (RRE) (Martarano et al 1994 J. Virol. 68:3102–11.). The mechanisms of action of these two proteins are thought to be broadly similar to the analogous mechanisms in the primate viruses (Martano et al ibid). The function of S2 is unknown. In addition, an EIAV protein, Ttm, has been identified that is encoded by the first exon of tat spliced to the env coding sequence at the start of the transmembrane protein.

In addition to protease, reverse transcriptase and integrase, non-primate lentiviruses contain a fourth pol gene product which codes for a dUTPase. This may play a role in the ability of these lentiviruses to infect certain non-dividing cell types.

The viral RNA in the first aspect of the invention is transcribed from a promoter, which may be of viral or non-viral origin, but which is capable of directing expression in a eukaryotic cell such as a mammalian cell. Optionally an enhancer is added, either upstream of the promoter or downstream. The RNA transcript is terminated at a polyadenylation site which may be the one provided in the lentiviral 3' LTR or a different polyadenylation signal.

Thus the present invention provides a DNA transcription unit comprising a promoter and optionally an enhancer capable of directing expression of a retroviral vector genome.

Transcription units as described herein comprise regions of nucleic acid containing sequences capable of being transcribed. Thus, sequences encoding mRNA, tRNA and rRNA are included within this definition. The sequences may be in the sense or antisense orientation with respect to the promoter. Antisense constructs can be used to inhibit the expression of a gene in a cell according to well-known techniques. Nucleic acids may be, for example, ribonucleic acid (RNA) or deoxyribonucleic acid (DNA) or analogues thereof. Sequences encoding mRNA will optionally include some or all of 5' and/or 3' transcribed but untranslated flanking sequences naturally, or otherwise, associated with the translated coding sequence. It may optionally further include the associated transcriptional control sequences normally associated with the transcribed sequences, for example transcriptional stop signals, polyadenylation sites and downstream enhancer elements. Nucleic acids may comprise: cDNA or genomic DNA (which may contain introns).

The term "promoter" is used in the normal sense of the art, e.g. an RNA polymerase binding site in the Jacob-Monod theory of gene expression.

The term "enhancer" includes a DNA sequence which binds to other protein components of the transcription initiation complex and thus facilitates the initiation of transcription directed by its associated promoter.

The promoter and enhancer of the transcription units encoding the first viral vector component are preferably strongly active, or capable of being strongly induced, in the producer cell under conditions for production of the retroviral vector of the present invention and/or in primary target cells under conditions for production of the secondary viral vector. The promoter and enhancer of the transcription units encoding the second viral vector component are preferably strongly active, or capable of being strongly induced, in the target cells. The promoter and/or enhancer may be constitutively efficient, or may be tissue or temporally restricted in their activity. Examples of suitable tissue restricted promoters/enhancers are those which are highly active in tumour cells such as a promoter/enhancer from a MUC1 gene, a CEA gene or a 5T4 antigen gene. Examples of temporally restricted promoters/enhancers are those which are responsive to ischaemia and/or hypoxia, such as hypoxia response elements or the promoter/enhancer of a grp78 or a grp94 gene. One preferred promoter-enhancer combination is a human cytomegalovirus (hCMV) major immediate early (MIE) promoter/enhancer combination.

The LTRs may be altered in, for example, U3 (such as to obtain strong constitutive expression, inducible expression or tissue specific expression); R (such as to remove TAR stem loops); or U5 (such as to use enhanced non-U5 based polyadenylation signals, for example from the bovine growth hormone gene).

In one configuration the internal promoter cassette is reversed and a polyadenylation signal is placed downstream of the cassette.

In another embodiment the polyadenylation signal which is used contains at least one intron.

The vector of the present invention may make use of self-inactivating strategies. Self-inactivating retroviral vectors have been constructed by deleting the transcriptional enhancers or the enhancers and promoters in the U3 region of the 3' LTR. After one round of vector replication, these changes are copied into both the 5' and the 3' LTRs producing an inactive provirus. However, any promoters internal to the LTRs in such vectors will still be active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it is of critical importance to prevent any activation of an endogenous oncogene.

Another type of self-inactivating vector has been constructed that has direct repeats flanking the packaging signal such that the packaging signal is frequently deleted during reverse transcription, producing virus defective for packaging. With sufficiently long direct repeats, a majority of resultant proviruses lose their packaging sequences. The rate of deletion could be increased to 100% by designing the vector so that packaging signal deletion reconstituted the neo marker and by selecting the vector-infected cells in G418. This strategy may be particularly useful for gene therapy applications where any spread of the vector following gene transfer is undesirable.

In a further preferred embodiment of the first aspect of the invention, one or more nucleotides of interest (NOI) is introduced into the vector at the cloning site. Such therapeutic genes may be expressed from a promoter placed in the retroviral LTR or may be expressed from an internal promoter introduced at the cloning site.

Suitable NOI coding sequences include those that are of therapeutic and/or diagnostic application such as, but are not limited to: sequences encoding cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppressor protein and growth factors, membrane proteins, vasoactive proteins and peptides, anti-viral proteins and ribozymes, and derivatives there of (such as with an associated reporter group). When included, such coding sequences may be typically operatively linked to a suitable promoter, which may be a promoter driving expression of a ribozyme(s), or a different promoter or promoters.

The NOI coding sequence may encode a fusion protein or a segment of a coding sequence.

The retroviral vector of the present invention may be used to deliver a NOI such as a pro-drug activating enzyme to a tumour site for the treatment of a cancer. In each case, a suitable pro-drug is used in the treatment of the individual (such as a patient) in combination with the appropriate pro-drug activating enzyme. An appropriate pro-drug is administered in conjunction with the vector. Examples of pro-drugs include: etoposide phosphate (with alkaline phosphatase, Senter et al 1988 Proc Natl Acad Sci 85: 4842–4846); 5-fluorocytosine (with cytosine deaminase, Mullen et al 1994 Cancer Res 54: 1503–1506); Doxorubicin-N-p-hydroxyphenoxyacetamide (with Penicillin-V-Amidase, Kerr et al 1990 Cancer Immunol Immunother 31: 202–206); Para-N-bis(2-chloroethyl) aminobenzoyl glutamate (with carboxypeptidase G2); Cephalosporin nitrogen mustard carbamates (with β-lactamase); SR4233 (with P450 Reducase); Ganciclovir (with HSV thymidine kinase, Borrelli et al 1988 Proc Natl Acad Sci 85: 7572–7576); mustard pro-drugs with nitroreductase (Friedlos et al 1997 J Med Chem 40: 1270–1275) and Cyclophosphamide (with P450 Chen et al 1996 Cancer Res 56: 1331–1340).

The vector of the present invention may be delivered to a target site by a viral or a non-viral vector.

As it is well known in the art, a vector is a tool that allows or faciliates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. Optionally, once within the target cell, the vector may then serve to maintain the heterologous DNA within the cell or may act as a unit of DNA replication. Examples of vectors used in recombinant DNA techniques include plasmids, chromosomes, artificial chromosomes or viruses.

Non-viral delivery systems include but are not limited to DNA transfection methods. Here, transfection includes a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof.

Viral delivery systems include but are not limited to adenovirus vector, an adeno-associated viral (AAV) vector, a herpes viral vector, retroviral vector, lentiviral vector, baculoviral vector. Other examples of vectors include ex vivo delivery systems, which include but are not limited to DNA transfection methods such as electroporation, DNA biolistics, lipid-mediated transfection, compacted DNA-mediated transfection.

The term "retroviral vector particle" refers to the packaged retroviral vector, that is preferably capable of binding to and entering target cells. The components of the particle, as already discussed for the vector, may be modified with respect to the wild type retrovirus. For example, the Env proteins in the proteinaceous coat of the particle may be genetically modified in order to alter their targeting specificity or achieve some other desired function.

Preferably, the viral vector preferentially transduces a certain cell type or cell types.

More preferably, the viral vector is a targeted vector, that is it has a tissue tropism which is altered compared to the native virus, so that the vector is targeted to particular cells.

For retroviral vectors, this may be achieved by modifying the Env protein. The Env protein of the retroviral secondary vector needs to be a non-toxic envelope or an envelope which may be produced in non-toxic amounts within the primary target cell, such as for example a MMLV amphotropic envelope or a modified amphotropic envelope. The safety feature in such a case is preferably the deletion of regions or sequence homology between retroviral components.

Preferably the envelope is one which allows transduction of human cells. Examples of suitable env genes include, but are not limited to, VSV-G, a MLV amphotropic env such as the 4070A env, the RD114 feline leukaemia virus env or haemagglutinin (HA) from an influenza virus. The Env protein may be one which is capable of binding to a receptor on a limited number of human cell types and may be an engineered envelope containing targeting moieties. The env and gag-sol coding sequences are transcribed from a promoter and optionally an enhancer active in the chosen packaging cell line and the transcription unit is terminated by a polyadenylation signal. For example, if the packaging cell is a human cell, a suitable promoter-enhancer combination is that from the human cytomegalovirus major immediate early (hCMV-MIE) gene and a polyadenylation signal from SV40 virus may be used. Other suitable promoters and polyadenylation signals are known in the art.

The packaging cell may be an in vivo packaging cell in the body of an individual to be treated or it may be a cell cultured in vitro such as a tissue culture cell line. Suitable cell lines include mammalian cells such as murine fibroblast derived cell lines or human cell lines. Preferably the packaging cell line is a human cell line, such as for example: 293 cell line, HEK293, 293-T, TE671, HT1080.

Alternatively, the packaging cell may be a cell derived from the individual to be treated such as a monocyte, macrophage, stem, cells, blood cell or fibroblast. The cell may be isolated from an individual and the packaging and vector components administered ex vivo followed by re-administration of the autologous packaging cells. Alternatively the packaging and vector components may be administered to the packaging cell in vivo. Methods for introducing retroviral packaging and vector components into cells of an individual are known in the art. For example, one approach is to introduce the different DNA sequences that are required to produce a retroviral vector particle e.g. the env coding sequence, the gag-pol coding sequence and the defective retroviral genome into the cell simultaneously by transient triple transfection (Landau & Littman 1992 J. Virol. 66, 5110; Soneoka et al 1995 Nucleic Acids Res 23:628–633).

In one embodiment the vector configurations of the present invention use as their production system, three transcription units expressing a genome, the gag-pol components and an envelope. The envelope expression cassette may include one of a number of envelopes such as VSV-G or various murine retrovirus envelopes such as 4070A.

Conventionally these three cassettes would be expressed from three plasmids transiently transfected into an appropriate cell line such as 293T or from integrated copies in a stable producer cell line. An alternative approach is to use another virus as an expression system for the three cassettes, for example baculovirus or adenovirus. These are both nuclear expression systems. To date the use of a poxvirus to express all of the components of a retroviral or lentiviral vector system has not been described. In particular, given the unusual codon usage of lentiviruses and their requirement for RNA handling systems such as the rev/RRE system it has not been clear whether incorporation of all three cassettes and their subsequent expression in a vector that expresses in the cytoplasm rather than the nucleus is feasible. Until now the possibility remained that key nuclear factors and nuclear RNA handling pathways would be required for expression of the vector components and their function in the gene delivery vehicle. Here we describe such a system and show that lentiviral components can be made in the cytoplasm and that they assemble into functional gene delivery systems. The advantage of this system is the ease with which poxviruses can be handled, the high expression levels and the ability to retain introns in the vector genomes.

According to another aspect therefore there is provided a hybrid viral vector system for in vivo gene delivery, which system comprises a primary viral vector which is obtainable from or is based on a poxvirus and a second viral vector which is obtainable from or is based on a retroviral vector, preferably at lentiviral vector, even more preferably a non-primate lentiviral vector.

The secondary vector may be produced from expression of essential genes for retroviral vector production encoded in the DNA of the primary vector. Such genes may include a gag-pol from a retrovirus, an env gene from an enveloped virus and a defective retroviral vector containing one or more therapeutic or diagnostic NOI(s). The defective retroviral vector contains in general terms sequences to enable reverse transcription, at least part of a 5' long terminal repeat (LTR), at least part of a 3' LTR and a packaging signal.

If it is desired to render the secondary vector replication defective, that secondary vector may be encoded by a plurality of transcription units, which may be located in a single or in two or more adenoviral or other primary vectors.

In some therapeutic or experimental situations it may be desirable to obviate the need to make EAIV derived from MVA in vitro. MVA-EIAV hybrids are delivered directly into the patient/animal e.g. MVA-EIAV is injected intravenously into the tail vein of a mouse and this recombinant virus infects a variety of murine tissues e.g. lung, spleen etc. Infected cells express transduction competent EIAV containing a therapeutic gene for gene therapy for example. EIAV vector particles bud from these cells and transduce neighbouring cells. The transduced cell then contains an integrated copy of the EIAV vector genome and expresses the therapeutic gene product or other gene product of interest. If expression of the therapeutic gene product is potentially toxic to the host it may be regulated by a specific promoter, e.g. the hypoxic response element (HRE), which will restrict expression to those cells in a hypoxic environment. For gene therapy of lung/trachea epithelium cells e.g to treat cystic fibrosis MVA-EIAV may be given as an aerosol delivered intranasally. Alternatively, macrophages can be transduced in vitro and then reintroduced to create macrophage factories for EIAV-based vectors. Furthermore, because MVA is replication incompetent MVA-EIAV hybrids could also be used to treat immuno-suppressed hosts.

Vaccinia virus, the prototypic member of the orthopox genus within the family poxviridae, was the first virus used for expression of recombinant exogenous proteins (Mackett et al 1982, Paoletti & Panicalli 1982). Vaccinia virus has a large DNA genome of greater than 180 kb and reports indicate that it can accommodate over 25 kb of foreign DNA (Merchlinsky & Moss 1992). Several other strains of poxviruses have been adapted as recombinant expression vectors (for review see Carroll and Moss 1997) e.g. fowlpox (Taylor & Paoletti 1988), canarypox (Taylor et al 1991), swinepox (van der Leek et al 1994) and entomopox (Li et al 1997). Additionally, due to safety concerns, several highly attenuated strains of vaccinia virus have been developed that are compromised in human and other mammalian cells e.g. modified vaccinia virus Ankara (MVA) (Mayr 1978, Sutter 1992), NYVAC (Paoletti et al 1994), vaccinia virus deficient in a DNA replication enzyme (Holzer et al 1997). These may all be used in the present invention.

MVA was derived from a replication competent vaccinia smallpox vaccine strain, Ankara. After >500 passages in chick embryo fibroblast cells the virus isolate was shown to be highly attenuated in a number of animal models including mice that were immune deficient (Mayr et al 1978). The attenuated isolate, MVA, was used to vaccinate over 120,000 people, many of which were inmmunocompromised (Mahnel 1994) without adverse effects. Studies illustrate that MA can infect a wide range of mammalian cells but productive infection has only been observed in Hamster kidney cell BHK-21 (Carroll 1997). In all other tested mammalian cell lines early expression, DNA replication and late expression are observed leading to the production of non-infectious immature virus particles (Carroll 1997, Meyer 1991). Virus replication studies show that a minority of mammalian cells can support very low level production of infectious virus i.e. BS-C-1 cells in which 1 infectious MVA particle is produced per cell (Carroll and Moss 1997). Late gene expression usually give rise to >10 fold more protein that those genes under early promoters (Chakrabarti et al 1997, Wyatt et al 1996). In all other attenuated poxvirus strains late gene expression is rarely observed in mammalian cells.

Production of retrovirus vector systems e.g. MLV-HIV and lentivirus vector systems requires the construction of producer lines that express the virus genome and essential structural proteins to make transduction competent virus. Generally, this is a relatively inefficient process which is further complicated when the virus is pseudotyped with toxic envelope proteins such as VSV-G. Expression of a functional genome and the required structural proteins from within a recombinant poxvirus may obviate many of the current inefficient retrovirus and lentivirus vector production technologies. Additionally, such recombinant poxviruses may be directly injected into patients to give rise to in vivo production of retrovirus or lentivirus.

MVA is a particularly suitable poxvirus for the construction of a pox-retrovirus or pox-lentivirus hybrid due to its non-replicating phenotype and its ability to perform both early and strong late expression for the production of high titre vector preparations.

In order to produce a functional retrovirus or lentivirus vector genome it is essential that the 5' of the RNA genome should be exact (Cannon et al. 1996). This is a challenge in a vaccinia-based production system as many of the vaccinia promoters comprise downstream determinants of transcription efficiency (Davison 1989b, Moss 1996). However, we show that there are several ways to solve this problem:

a. Use of a T7 promoter and T7 termination sequence.
b. Use of early promoters (in which sequences downstream of the RNA start site are not highly conserved), (Davison 1989a).
c. Use of intermediate and late promoters of vaccinia which require additional sequences downstream of the initiation site in conjunction with strategies to generate an authentic 5' end or which place the additional downstream sequences into both R regions. There is a requirement for specific sequences of 4 nucleotides downstream of the initiation of transcription in the late promoter (Davison 1989b, Moss 1996). In the first case a ribozyme is placed downstream of the promoter and upstream of the R region. The ribozyme is designed to cleave the RNA in cis to generate the correct 5' end. In the second the approach is to modify the R regions to incorporate the extra sequences. This must be done in both the 5' and the 3' LTR R regions.

The advantage of having a T7 dependent system is that it would require the infection of the cell by two recombinant vaccinia viruses to produce transducing EIAV viral particles. For example, one MVA could carry the vector genome, under the control of the T7 promoter and the gag/pol and the env sequences under the control of the vaccinia promoters. The other MVA would carry the T7 polymerase gene under the control of a vaccinia promoter (Wyatt et al 1995).

The retroviral vector particle according to the invention will also be capable of transducing cells which are slowly-dividing, and which non-lentiviruses such as MLV would not be able to efficiently transduce. Slowly-dividing cells divide once in about every three to four days including certain tumour cells. Although tumours contain rapidly dividing cells, some tumour cells especially those in the centre of the tumour, divide infrequently. Alternatively the target cell may be a growth-arrested cell capable of undergoing cell division such as a cell in a central portion of a tumour mass or a stem cell such as a haematopoietic stem cell or a CD34-positive cell. As a further alternative, the target cell may be a precursor of a differentiated cell such as a monocyte precursor, a CD33-positive cell, or a myeloid precursor. As a further alternative, the target cell may be a differentiated cell such as a neuron, astrocyte, glial cell, microglial cell, macrophage, monocyte, epithelial cell, endothelial cell or hepatocyte. Target cells may be transduced either in vitro after isolation from a human individual or may be transduced directly in vivo.

The delivery of one or more therapeutic genes by a vector system according to the present invention may be used alone or in combination with other treatments or components of the treatment.

For example, the retroviral vector of the present invention may be used to deliver one or more NOI(s) useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermnolysis bullosa; corneal ulceration, retinopathy and surgical wound healing; rhinitis, allergic conjunctivitis, eczema, anaphylaxis; restenosis, congestive heart failure, endornetriosis, atherosclerosis or endosclerosis.

In addition, or in the alternative, the retroviral vector of the present invention may be used to deliver one or more NOI(s) useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the retroviral vector of the present invention may be used to deliver one or more NOI(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex, HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyclitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

The present invention also provides a pharmaceutical composition for treating an individual by gene therapy, wherein the composition comprises a therapeutically effective amount of the retroviral vector of the present invention comprising one or more deliverable therapeutic and/or diagnostic NOI(s) or a viral particle produced by or obtained from same. The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant (s), suspending agent(s), coating agent(s), solubilising agent (s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The delivery of one or more therapeutic genes by a vector system according to the invention may be used alone or in combination with other treatments or components of the treatment. Diseases which may be treated include, but are not limited to: cancer, neurological diseases, inherited diseases, heart disease, stroke, arthritis, viral infections and diseases of the immune system. Suitable therapeutic genes include those coding for tumour suppressor proteins, enzymes, pro-drug activating enzymes, immunomodulatory molecules, antibodies, engineered immunoglobulin-like molecules, fusion proteins, hormones, membrane proteins, vasoactive proteins or peptides, cytokines, chemokines, antiviral proteins, antisense RNA and ribozymes.

In a preferred embodiment of a method of treatment according to the invention, a gene encoding a pro-drug activating enzyme is delivered to a tumour using the vector system of the invention and the individual is subsequently treated with an appropriate pro-drug. Examples of pro-drugs include etoposide phosphate (used with alkaline phosphatase Senter et al., 1988 Proc. Natl. Acad. Sci. 85: 4842–4846); 5-fluorocytosine (with Cytosine deaminase Mullen et al. 1994 Cancer Res. 54: 1503–1506); Doxorubicin-N-p-hydroxyphenoxyacetamide (with Penicillin-V-Amidase (Kerr et al. 1990 Cancer Immunol. Immunother. 31: 202–206); Para-N-bis(2-chloroethyl) aminobenzoyl glutamate (with Carboxypeptidase G2); Cephalosporin nitrogen mustard carbamates (with b-lactamase); SR4233 (with P450 Reducase); Ganciclovir (with HSV thymidine kinase, Borrelli et al. 1988 Proc. Natl. Acad. Sci. 85: 7572–7576) mustard pro-drugs with nitroreductase (Friedlos et al. 1997J Med Chem 40: 1270–1275) and Cyclophosphamide or Ifosfamide (with a cytochrome P450 Chen et al. 1996 Cancer Res 56: 1331–1340).

In accordance with the invention, standard molecular biology techniques may be used which are within the level of skill in the art. Such techniques are fully described in the literature. See for example; Sambrook et al (1989) Molecular Cloning; a laboratory manual; Hames and Glover (1985–1997) DNA Cloning: a practical approach, Volumes I–IV (second edition); Methods for the engineering of immunoglobulin genes are given in McCafferty et al (1996) "Antibody Engineering: A Practical Approach".

EXAMPLE 1

Construction of EIAV Vectors Containing Deleted gag Genes

In order to construct a replication incompetent EIAV vector system we have used, as a starting point, an infectious proviral clone pSPEIAV19 (accession number: U01866), described by Payne et al. (1994, J Gen Virol. 75:425–9). An initial EIAV based vector was constructed by simply deleting part of env by removing a Hind III/Hind III fragment corresponding to coordinates 5835/6571 according to the numbering system of Payne et al. (ibid.). This fragment was replaced with the puromycin resistance gene under the control of the SV40 early promoter from pTIN500 (Cannon et al 1996 J. Virol. 70:8234–8240) to create pESP (FIG. 1). Viral stocks were produced by calcium phosphate transfection of 293T cells (Soneoka et al 1995 Nucl. Acids Res. 23:628–633) with pESP and pRV67 (Kim et al 1998 J. Virol. 72(1):811–6) a plasmid in which the vesicular stomatitis virus glycoprotein (VSV-G) is expressed from the HCMV-IE enhancer/promoter. Alternatively other VSV-G expression plasmids can be used eg Yee, et al 1994 PNAS 91:9564–9568. The resulting supernatant was used to transduce human kidney (293T) and canine osteosarcoma cells (D17) as follows. 48 hours post-transfection tissue culture fluid was collected and filtered through 0.45 µm filters. Ten-fold dilutions were made in culture medium containing polybrene at 8 µg/ml and then 500 µl aliquots placed on D17 cells seeded at 1.6×105/well in 12 well plates on the previous day. Two hours later 1 ml of culture media was added. Two days later puromycin was added to a final concentration of 4 ug/ml and incubation was continued for a further 7 days. As a positive control, a Murine leukaemia virus (MLV) based vector (pTIN500) containing the puromycin resistance gene under the control of the SV40 early promoter was used in conjunction with pHIT60 (MLV gagpol) and pRV67 (Cannon et al 1996 J. Virol. 70:8234–8240). No resistance colonies were detected on either cell type after 7 days of puromycin selection with the EIAV vector. The MLV vector produced $5.0 \times 10^4$ c.f.u./ml on 293T cells and $1.0 \times 10^4$ c.f.u./ml on D17 cells.

The likely explanation for this result is that the EIAV LTR is not functional in human cells in the absence of tat and so insufficient amounts of the critical components such as gag-pol and tat are produced.

A further vector system was therefore constructed comprising three transcription units to produce the following: 1) vector genome RNA; 2) env and 3) gag-pol. In order to ensure that sufficient amounts of each component is produced, the env and gag-pol transcription units are transcribed from a promoter-enhancer active in the chosen human packaging cell line. In this way, sufficient gag-pol and, most likely tat, are produced to ensure efficient production of transduction-competent vector particles.

The vector genome was constructed which has the reporter gene within the pol region of the genome as follows. The plasmid designated pONY1 was constructed by inserting the EIAV LTR, amplified by PCR from pSPEIAV19, into pBluescript II KS+ (Stratagene). The 5' LTR of EIAV clone pSPEIAV19 was PCR amplified using pfu polymerase with the following primers: 5' GCATGGACCTGTGGGGTTTTTATGAGG (SEQ ID NO: 29) 3'GCATGAGCTCTGTAGGATCTCGAACAGAC (SEQ ID NO: 30)

The amplicon was blunt ended by 5' overhang fill-in and inserted into pBluescript II KS+ cut with Bss HII which had been blunt ended by 3' overhang removal using T4 DNA polymerase. This construct was called pONY1 and the orientation was 5' to 3' in relation to β-galactosidase of pBluescript II KS+. Sequencing of pONY1 revealed no mutations.

Vector genome pSPEIAV19DH was cut with Mlu I (216/8124) and inserted into pONY1 Mlu I cut (216) to make pONY2. A Bss HII digest (619/792) of pBluescript II KS+ was carried out to obtain the multiple cloning site. This was blunt ended by 5' overhang fill-in and ligated to pONY2 cut with Bgl II and Nco I (1901/4949) and blunt ended by 5' overhang fill-in. The orientation was 3' to 5' in relation to the EIAV sequence. This was called pONY2.1. pSPCMV was created by inserting pLNCX (Accession number: M28246) (Pst I/Hind III) into pSP72 (Promega). The β-galactosidase gene was inserted from pTIN414 (Cannon P M et al J. Virol. 70, 8234–8240) into pSP72 (Xho I/Sph I) to make pSPlacZ. The 5' end to the β-galactosidase gene was replaced by the SV40 T antigen nuclear localization signal from pAD.RSVbgal (J. Clin. Invet. 90:626–630, 1992). pAD.RSVbgal was cut with Xho I/ Cla I and inserted into Xho I/ Cla I pSPlacZ to make pSPnlslacZ. The CMV nuclear localizing and non nuclear localizing β-galactosidase from pSPlacZ and pSPnlslacZ was cut out with Pst I and inserted into the Pst I site of pONY2.1 in the 5' to 3' orientation of EIAV. These were called pONY2.1nlslacZ and pONY2.1lacZ.

An EIAV gagpol expression plasmid (pONY3) was then made by inserting Mlu I/Mlu I fragment from pONY2ΔH into the mammalian expression plasmid pCI-neo (Promega) such that the gag-pol gene is expressed from the hCMV-MIE promoter-enhancer. In particular, gagpol pSPEIAV19DH was cut with Mlu I (216/8124) and inserted into pCI-Neo (Promega) Mlu I cut (216) to make pONY3. Plasmid pONY3 should not produce a functional genome because it lacks the appropriate LTR sequences. Virus was produced by transient three plasmid cotransfection of 293T cells with pRV67, pONY3 and pONY2.10nlsLacZ as described for MLV-based vectors (Soneoka et al 1995 Nucl. Acids Res. 23:628–633) and then used to transduce 293T cells and D17 cells as follows. 48 hours post-transfection tissue culture fluid was collected and filtered through 0.45 μm filters. Ten-fold dilutions were made in culture medium containing polybrene at 8 μg/ml and then 500 ul aliquots placed on D17 cells seeded at 1.6×105/well in 12 well plates on the previous day. Two hours later 1 ml of culture media was added and incubation continued for 48 hours prior to assessment of LacZ gene expression using the X-gal staining procedure. for *E coli* β-galactosidase (macGregor et al 1991 Methods in Molecular Biology Vol 7 ed E J Murray p217–235). In both cases the virus transduced the cells at frequencies of about $10^5$ LacZ-transducing cell—forming—unit (i.f.u.)/ml which was about 10-fold less than with the MLV-based vector produced from pHIT111. These data showed that we had produced an EIAV-based vector system and also suggested that replacement of the Hind III/Hind III fragment in env with foreign DNA may disrupt the function of the genome.

We next characterized the ability of the EIAV vector particles to be pseudotyped with envelope proteins from other viruses. pONY2.10nlsLacZ and pONY3 were cotransfected with envelope expression plasmids producing MLV amphotropic (pHIT456) and MLV ecotropic (pHIT123) envelopes (Soneoka et al 1995 Nucl. Acids Res. 23:628–633) as well as VSV-G (pRV67) (Table 1). pHIT 111 (MLV vector genome) and pHIT60 (MLV gagpol expression plasmid) were cotransfected with the envelope plasmids as positive controls (Table 1). The viral supernatants were used to transduce a variety of cell lines including human kidney (293T), murine embryo (NIH3T3) and canine osteosarcoma (D17). As expected, the cell tropism of the virus was largely determined by the envelope. EIAV could be pseudotyped with amphotropic envelope, but transduction efficiencies varied. The amphotropic pseudotyped virus gave titres of about 102 on D17 cells, 103 on NIH3T3 cells and 104 on 293T cells. The reason for these differences was not pursued. EIAV could also be pseudotyped with the MLV ecotropic envelope and these viruses transduced NIH3T3 cells at titres of 104 1.f.u./ml. EIAV, pseudotyped with VSV-G envelope, transduced all the cell lines tested. The titer varied between the different envelopes and cell types but overall efficiencies were relatively high for the non-murine cells, but still lower than with a murine vector system. Taken together, these data show that the EIAV vector system is not dependent on the EIAV envelope and can be effectively pseudotyped with three envelopes conferring broad host range. This makes this system as generally useful as current MLV-based systems.

EIAV vectors can also be pseudotyped in the same manner using the RD114 envelope, for instance using pRDF (Cosset et al 1995 J. Virol. 69: 7430–7436).

In order to characterize the transduction events further we carried out a PCR analysis of 293T cells transduced by the EIAV vector pseudotyped with VSV-G. In particular we asked if the vector genome, as opposed to a recombinant with the gagpol expression plasmid, pONY3, had been the transduction vehicle for the β-galactosidase gene. PCR amplification using primers specific for the EIAV LTR gave the expected PCR product of 310 bp when genomic DNA isolated from transduced cells was used (FIG. 2A, lane 1). No PCR product was detected when mock transduced 293T cell DNA was used as template (FIG. 2A, lane 2). pONY2.10nlsLacZ was used as a positive control (FIG. 2A, lane 3). No PCR product was detected when pONY3 was used as a template (FIG. 2A, lane 4). The lack of a PCR product, when using pol specific primers, (FIG. 2B) confirmed that no gagpol sequences from pONY3 had integrated into the host chromosomes. Taken together these data show that the authentic vector genome had transduced the cells.

In order to determine if the EIAV vector retained the ability to transduce non-dividing cells, 293T cells were arrested in G1/S phase by treatment with aphidicolin according to published procedures (Lewis and Emerman 1994) and then transduced with EIAV-based and MLV-based vectors pseudotyped with VSV-G. The transduction efficiency of the MLV vector was lower by four orders of magnitude in aphidicolin treated cells as compared to untreated cells. The incomplete block to cell transduction by MLV was probably due to a small population of dividing cells. In contrast, no significant difference was observed in the case of the EIAV-based vector. This demonstrates that the EIAV vector, like HIV vectors, can efficiently transduce non-dividing cells.

The vector genome pONY2.10lacZ contains 1377nt of gag. RNA secondary structure prediction ("http://www.ibc.wustl.edu/~zuker/rna/") was used to identify possible stem-loop structures within the leader and the 5' end of gag. Based on these predictions four deletions were made within the gag region of pONY2.10 lacZ (FIG. 1). Deletions were made by PCR mutagenesis using standard techniques.

pONY2.1lacZ contains 1377nt of gag (deleted from position 1901nt)

pONY2.11lacZ contains 354nt of gag (deleted from position 878nt)

pONY2.12lacZ contains 184nt of gag (deleted from position 708nt)

pONY2.13lacZ contains 109nt of gag (deleted from position 633nt)

pONY2.14lacZ contains 2nt of gag (deleted from position 526nt)

These vectors were used in a three plasmid cotransfection as described for MLV-based vectors (Soneoka et al 1995 Nucl. Acids Res. 23:628–633) and the virus generated was titred on 293T and D17 cells.

It was found that the first 109nt of gag coding sequence were needed for maximal packaging in addition to the un-translated region; pONY2.13lacz (Table 2). Similar titres were found on D17 cells. The predicted secondary structure of the gag sequence derived RNA in pONY2.13lacZ is shown in FIG. 4.

Figure 4:
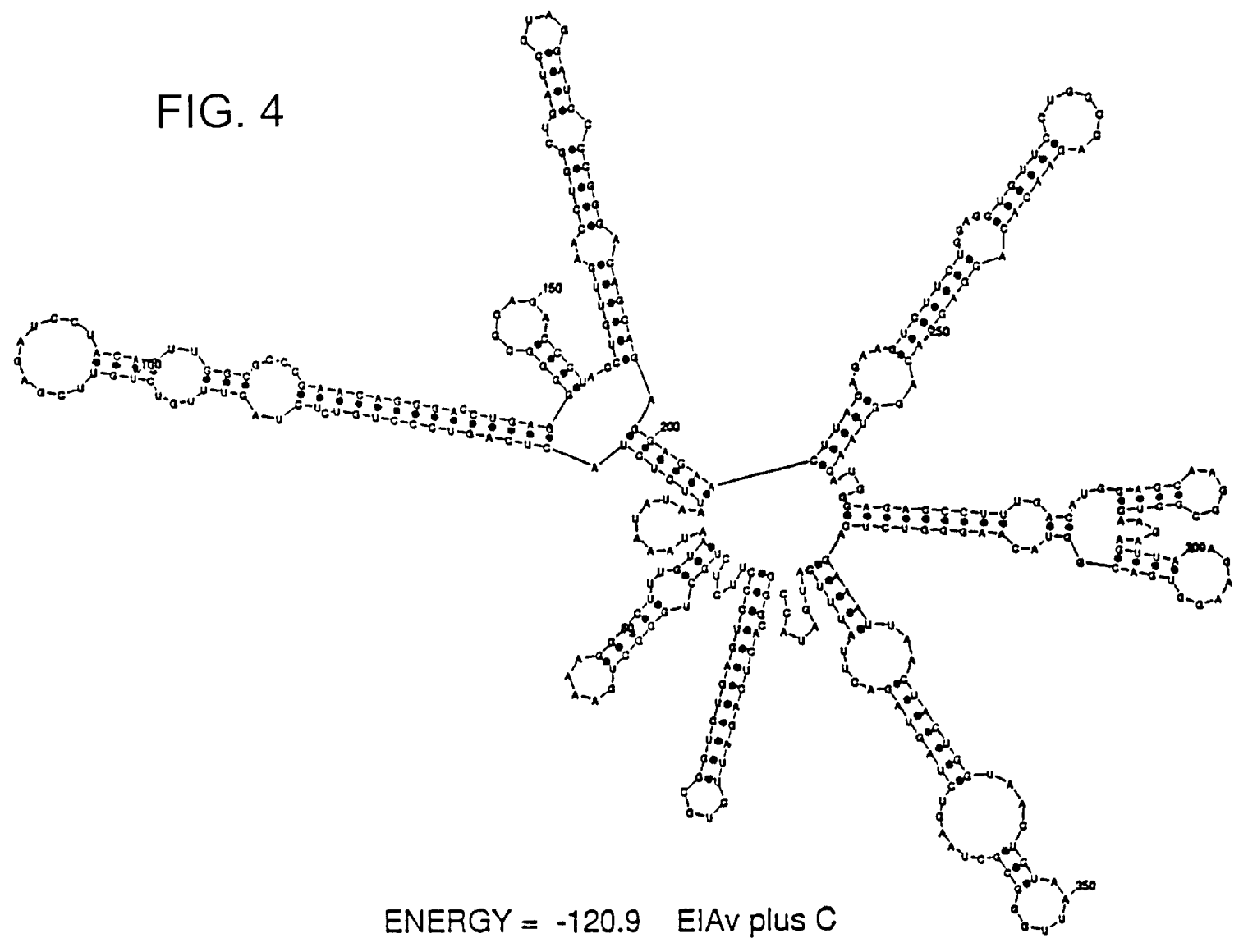

Based on the secondary structure prediction in FIG. 4, four further deletions were made within the area upstream and downstream of the major splice donor codon in pONY2.13lacZ.

pONY2.21lacZ contains deleted between position 409 to 421nt pONY2.22lacZ contains deleted between position 424 to 463nt pONY2.23lacZ contains deleted between position 470 to 524nt pONY2.24lacZ contains deleted between position 529 to 582nt pONY2.25lacZ contains deleted between position 584 to 645nt pONY2.26lacZ contains deleted between position 409 to 421nt and between position 470 to 542nt.

These vectors were used in a three plasmid co-transfection as described above and the virus generated was titred on D17 cells. It was found that deletions within this region severely affected the titre of the virus (Table 3). Constructs pONY2.23 and 2.26 gave the lowest titre. These both contained the deletion between position 470 to 524nt. The least severe deletion was the one between position 409 to 421nt. Based on this information the region around the major splice donor is useful for optimal packaging.

Similar secondary structure predictions and deletion analysis may be used to identify the packaging signal in other non-primate lentiviruses.

TABLE 1

Transduction efficiency of viral vectors.

| Vector | Envelope | Titer (l.f.u./ml)[a] | | |
|---|---|---|---|---|
| | | D17 | NIH3T3 | 293T |
| pONY2.1nlslacZ | Mock | <1 | <1 | <1 |
| pONY2.1nlslacZ | pHIT456 (MLVamp) | $1.0 \times 10^2$ | $8.4 \times 10^2$ | $2.0 \times 10^4$ |
| pONY2.1nlslacZ | pHIT123 (MLVeco) | <1 | $1.5 \times 10^4$ | <1 |
| pONY2.1nlslacZ | pRV67 (VSVG) | $1.0 \times 10^5$ | $3.6 \times 10^3$ | $2.0 \times 10^5$ |
| pHIT111 | Mock | <1 | <1 | <1 |
| pHIT111 | pHIT456 (MLVamp) | $1.3 \times 10^5$ | $2.6 \times 10^6$ | $2.0 \times 10^7$ |
| pHIT111 | pHIT123 (MLVeco) | <1 | $2.8 \times 10^6$ | <1 |
| pHIT111 | pRV67 (VSVG) | $3.0 \times 10^6$ | $2.0 \times 10^5$ | $5.0 \times 10^6$ |

[a]Each cell type was transduced and stained for β-galactosidase activity 48 hours after transduction of the target cells. Titers were averaged from three independent experiments and calculated as lac Z forming units per ml. There was no more than 10% variation between experiments.
pONY2.1nlsLacZ and the envelope expression plasmids were contransfected with the EIAV gagpol expression plasmid (pONY3).
pHIT111 and the envelope expression plasmids were cotransfected with the MLV gagpol expression plasmid (pHIT60).

TABLE 2

| Vector Genome | Titre (l.f.u/ml) |
|---|---|
| PONY2.10 | 3.30E + 04 |
| PONY2.11 | 1.60E + 05 |
| PONY2.12 | 1.40E + 05 |
| PONY2.13 | 1.70E + 05 |
| PONY2.14 | 5.40E + 02 |
| Mock | 1.0E + 01 |

TABLE 3

| Vector Genome | Titre (l.f.u/ml) |
|---|---|
| 2.21 | 1.20E + 04 |
| 2.22 | 3.80E + 03 |
| 2.23 | 1.20E + 02 |
| 2.24 | 5.20E + 02 |
| 2.25 | 5.60E + 02 |
| 2.26 | 1.00E + 02 |
| 2.13 | 4.00E + 04 |

EXAMPLE 2
Construction of pEGASUS-1

An EIAV—based vector was made (pEGASUS-1) that contains only 759nt of EIAV sequences (268nt-675nt and 7942nt-8292nt) as follows.

Sequences encompassing the EIAV polypurine tract (PPT) and the 3'LTR were obtained by PCR amplification from pONY2.10LacZ using primers PPTEIAV+ (Y8198): GACTACGACTAGTGTATGTTTAGAAAAACAAGG (SEQ ID NO: 31), and 3'NEGSpeI (Y8199) :CTAGGCTACTAGTACTGTAGGGATCTCGAACAG (SEQ ID NO: 32). The product was purified, digested with SpeI (ACTAGT) and ligated into pBS II KS+ which had been prepared by digestion with SpeI and treatment with alkaline phosphatase. Colonies obtained following transformation into E. coli, XL-1Blue were screened for the presence of the 3'LTR in the orientation in which the U5 region of the 3'LTR was proximal to the NotI site of the pBS II KS+ linker. The sequence of the cloned insert was determined and showed that it contained only one change from the EIAV clone pSPEIAV19 (AC: U01866). This was a 'C' insertion between bases 3 and 4 of the R region. The same change was found in the template used in the PCR reaction. The clone was termed pBS.3'LTR.

Next the reporter gene cassette, CMV promoter/LacZ, was introduced into the PstI site of pBS.3'LTR. The CMV/LacZ cassette was obtained as a PstI fragment from pONY2.10LacZ (see above). The ligation reaction to join the above fragments was transformed into E. coli, XL-1Blue. A number of clones in which the CMV/LacZ insert was orientated so that the LacZ gene was proximal to the 3'LTR were assessed for activity of the CMV/LacZ cassette by transfection into the cell line 293T using standard procedures. A clone which gave blue cells at 48 hours post-transfection following development with X-gal was selected for further use and termed pBS CMVLacZ.3'LTR. The 5'region of the EIAV vector was constructed in the expression vector pCIEneo which is a derivative of pCIneo (Promega) modified by the inclusion of approximately 400 base pairs derived from the 5'end of the full CMV promoter as defined previously. This 400 base pair fragment was obtained by PCR amplifcation using primers VSAT1 (GGGCTATATGAGATCTTGAATAATAAAATGTGT (SEQ ID NO: 33)) and VSAT2 (TATTAATAACTAGT (SEQ ID NO:34)) and pFIT60 as template. The product was digested with BglII and SpeI and ligated into pCIneo which had been digested similarly.

A fragment of the EIAV genome running from the R region to nt 150 of the gag coding region (nt 268 to 675) was amplified with primers CMV5'EIAV2 (Z0591) (GCTACGCAGAGCTCGTTTAGTGAACCGGGCACTC AGATTCTG (SEQ ID NO: 35): and 3'PSI.NEG (GCTGAGCTCTAGAGTCCTTTTCTTTTACAAAGTTGG (SEQ ID NO: 36)) using as template DNA. The 5'region of the primer CMV5'EIAV2 contains the sequences immediately upstream of the CMV promoter transcriptional start site and can be cut with SacI. 3'PSI.NEG binds 3' of the EIAV packaging sequences as defined by deletion analysis (above) and contains an XbaI site. The PCR product was trimmed with SacI and XbaI and ligated into pCIEneo which had been prepared for ligation by digestion with the same enzymes. This manipulation places the start of the EIAV R region at the transcriptional start point of the CMV promoter and transcripts produced thus start at the genuine start position used by EIAV and extend to the 3'-side of the packaging signal. Clones which appeared to be correct as assessed by restriction analysis were sequenced. A clone termed pCIEneo.5'EIAV was selected for further work.

In the next step the CMVLacZ and 3'LTR cassette in pBS.CMVLacZ.3'LTR was introduced into pCIEneo.5'EIAV. pBS.CMVLacZ.3'LTR was digested with ApaI, the 3'overhangs removed with T4 DNA polymerase, then digested with NotI. The fragment containing the CMV-LacZ.3 'LTR was purified by standard molecular biology techniques. The vector for ligation with this fragment was prepared from pCIEneo.5'EIAV by digestion with SalI, followed by filling-in of the 5' overhangs using T4 DNA polymerase. The DNA was then digested with NotI and purified prior to use in ligation reactions.

Following transformation into E.coli, XL-1Blue colonies were screened for the presence of the insert by restriction analysis to identify the required clone, designated pEGASUS-1.

The function of the pEGASUS-1 EIAV vector was compared to pONY2.10LacZ using the three plasmid co-transfection system as described in Example 1. Comparable titres were obtained from both vectors indicating that pEGASUS-1 contains all the sequences required for packaging with good efficiency.

EXAMPLE 3
Introduction of RRE's into EIAV Vectors

Further improvements to the EIAV vector pEGASUS-1 may be made by introduction of additional elements to improve titre. A convenient site for the introduction of such elements is the SalI site which lies between the XbaI to the 3' of the packaging signal and upstream of the CMV/LacZ cassette of pEGASUS-1. For example the RRE from HIV or EIAV can be inserted at this site.

The HIV-1 RRE was obtained from the HIV-1 molecular clone pWI3 (Kimpton and Emerman 1992 (J. Virol. 66: 2232–2239) by PCR amplification using primers RRE(+) GTCGCTGAGGTCGACAAGGCAAAGAGAAGAG (SEQ ID NO: 37) and RRE(−) GACCGGTACCGTCGACAAGGCACAGCAGTGG (SEQ ID NO: 38). The fragment of DNA and pEGASUS-1 were digested with SalI and following ligation, transformed into E.coli, XL-1 Blue. Colonies were screened for the presence of the HIV RRE and two clones, with the HIV RRE in either the positive or negative orientation, used for further work These vectors, pEGASUS-2.HIV RRE(+) or pEGASUS-2.HIV RRE(−) can be tested in 293T cells by carrying out a four plasmid co-transfection in which the plasmid pCIneoHIVrev, expressing the rev protein from HIV-1 is co-transfected with vector, pONY3 and pRV67 plasmids The EIAV RRE as defined previously (Martarano et al 1994) was obtained by PCR amplification as follows. Using pONY2.10LacZ as template 2 amplifications were performed to obtain the two parts of the EIAV RRE. The 5'-element was obtained using primers ERRE1 (TTCTGTCGACGAATCCCAGGGGGAATCTCAAC (SEQ ID NO: 39)) and ERRE2 (GTCACCTTCCAGAGGGCCCTGGCTAAGCATAACAG (SEQ ID NO: 40)) and the 3'element with ERRE3 (CTGTTATGCTTAGCCAGGGCCCTCTGGAAGGTGAC (SEQ ID NO: 41)) and ERRE4 (AATTGCTGACCCCCAAAATAGCCATAAG (SEQ ID NO: 42)). These products will anneal to each other hence can be used in second PCR reaction to obtain a DNA which 'encodes' the EIAV RRE. The PCR amplification is set up with out primers ERRE1 and ERRE4 for the first 10 cycles and then these primers are added to the reaction and a further 10 cycles of amplification carried out. The resulting PCR product and pEGASUS-1 were digested with SalI, ligated and transformed into E.coli XL-1Blue. Clones in which the EIAV RRE was in either the positive or negative orientations were selected for further work. The activity of these vectors was assessed in 4-way co-transfectioand pEGASUS-1 were digested with SalI, ligated and transformed into E.coli XL-1Blue. Clones in which the EIAV RRE was in either the positive or negative orientations were selected for further work. The activity of these vectors was assessed in three palsmid co-transfections, (EIAV rev being supplied by pONY3) or in 4-plasmid co-transfection experiments as described above, but using pCIneo.EIAV Rev to supply additional EIAV rev.

For construction of pCIneo EIAV REV the EIAV REV encoding sequences were derived by PCR amplification. The EIAV REV sequences were obtained using a two step 'overlapping' PCR amplification procedure as described above for the EIAV RRE. Template for the two reactions was pONY3 and primers for the 5'fragment were EIAV REV5'O (CCATGCACGTCTGCAGCCAGCATGGCAGAATCG AAG (SEQ ID NO: 43)) and EAIV REV IN (CCTGAGGATCTATTTTCCACCAGTCATTTC (SEQ ID NO: 44)) and for the 3'product EIAV REV IP (GTGGAAAATAGATCCTCAGGGCCCTCTGG (SEQ ID NO: 45)) and EIAV.REV3'O (GCAGTGCCGGATCCTCATAAATGTTTCCTCCTTCG (SEQ ID NO: 46)). The second PCR amplification was carried out with primers EIAV REV5'O and EIAV REV3'O being added after 10 cycles. The resulting product was ligated with the PCR fragment 'TA' cloning vector pCR2.1 (Invitrogen) the orientation of the EIAV REV insert was assessed by restriction enzyme analysis and the presence of the correct EIAV REV sequence confirmed. The construct was called pTopoRevpos. The EIAV REV insert was excised from pTopoRevpos by digestion with SpeI and NotI and ligated into pCIneo which had been digested with NheI and NotI.

EXAMPLE 4
Transduction of Human Macrophages

Primary human monocytes were obtained from leukocyte-enriched blood (from the National Blood Transfusion Service, Southmead Rd Bristol, UK) as follows. Peripheral blood mononuclear cells (PBMC) were enriched by centrifugation above a Ficoll discontinuous gradient (Pharmacia) according to the manufacturer's instructions. Macrophages were obtained from this cell population by adherence to tissue culture plastic over 7 days in RPMI 1640 medium (Dutch modified ; Sigma) containing 2% heat-inactivated human AB serum (Sigma) or 10% FCS (Sigma). Non-adherent cells were removed by extensive washing of the plates with medium.

Virus for transduction experiments was obtained by three plasmid co-transfection into 293T cells. The vector for the experiments was a pONY2.13 derivative in which the CMV/LacZ reporter cassette had been replaced with CMV/green fluorescent protein (GFP).

Vector pONY2.13GFP was made as follows. The sequence encoding the red-shifted GFP and eukaryotic translation signals was cut out of pEGFP-N1 (Clontech "http://www.clontech.com/") with BglII and XbaI and ligated into the general cloning vector pSP72 (Promega) which had been prepared by digestion with the same enzymes. The GFP-encoding sequences were then excised using XhoI and ligated into pONY2.13 which had been cut with XhoI (thereby releasing the LacZ coding region). Following transformation into E.coli, XL-1Blue clones in which the orientation of the GFP insert with respect to the CMV promoter was such that expression would be expected were determined restriction analysis and expression of GFP confirmed by transfection of DNA into 293T cells.

Vector was recovered by three plasmid co-transfection into 293T cells and harvested at 42–48 hours post-transfection: tissue culture fluid was 0.45 (m-filtered and virus was then pelleted by centrifugation at 50,000 g (20 Krpm), for 90 minutes at 4 (C in a SW40Ti rotor. Virus was resupended in 50–100 (l of complete media for 2 hours and then used in transduction experiments. Transductions with pONY2.13GFP vector were carried out as follows. Macrophages, seeded at 5×105 per well of 48-well plates were washed once with medium and then 300 (l of medium was put back on the cells. Virus was added to the medium and gently pipetted up 2–3 times to ensure mixing. Transduction efficiency was assessed at 3–5 days post-transduction. The number of transduced macrophages was determined using a fluorescence microscope. Expression of GFP can be monitored for extended periods, e.g., up to several weeks. Alternatively, transductions can be carried out with vectors carrying the LacZ marker. In such experiments the transduction frequency is assessed by detecting the presence of β-galactosidase using immunological procedures.

EXAMPLE 5
Introduction of EIAV Vectors in Vivo in Rat Brain

Adult Wistar rats were anaesthetised with a solution containing 1 part Nembutal (0.1 ml/35 gm body weight) 1 part Novetal (0.1 ml/35 gm body weight) and 2 parts dH2O, and placed into a stereotaxic apparatus. A midline incision was made along the rostral-to-caudal length of the scalp and the skin deflected back to expose the skull. Using stereotaxic coordinates (measured from Bregma) of 3.00 mm posterior and 3.00 lateral, a 1 mm diameter hole was drilled into the skull. Unilateral intracortical injections of EIAV vectors were then made using a 10 μl Hamilton syringe or a 1.0 μl fine glass capillary to various depths from the surface of the brain. The syringe was left in place an additional 5 min to prevent reflux. Control animals receive a single 10 μl intracortical injection of saline with the Hamilton or 1.0 μl with the fine glass capillary. Animals were then sutured and left to recover. Forty-eight hours later, these animals were deeply anesthetized as described above and perfused through the heart with 200 ml of phosphate-buffered saline (PBS). The brains were then dissected out, frozen into dry-ice cooled isopentane (−30° C.) and cut coronally at 1.0 μm with a cryostat. Every 5th section through the injection site and 2 mm rostral and caudal are collected onto Super-Frost slides, fixed and either X-gal or immunostained or stained with Cresyl Violet.

EXAMPLE 6
Transduction of Bronchial Cells Differentiated in Culture

Epithelial cells can be differentiated to form epithelia-like monolayers which display (>1000 Ω cm$^3$) electrical resistance and a cuboidal morphology. There are various wasys to do this for example Fuller et al 1984. This creates polarized cells. This polarity is functional and mimics epithelial cells in vivo. Thus EIAV vectors can be used to transduce these cells either through the basolateral surface or the apical surface using vectors and preparations as described in Examples 1–3.

EXAMPLE 7
A Minimal EIAV System

In order to eliminate the risk of accessory genes or coding sequences having deleterious effects in therapeutic applications, vector systems lacking tat, S2 and the dUTPase are constructed.

Construction of S2 Mutants

A) Vector Genome pONY2.13lacZ contains 109nt of gag (deleted from nucleotide positions 633 to 4949) (pONY2.13lacZ is described above). This vector is used to make an EIAV vector genome from which S2 expression is eliminated by deletion from nucleotide positions 5345 to 5397. This removes the ATG start codon of S2 and the start codon of env. To make the deletion within S2, PCR is carried out with SY2/SY5 and SY3/SY4 using pONY2.13 DNA as template. The two PCR products are pooled and PCR is carried out with primers SY5 and SY3. The 1.1 kb product is ligated into pGEMT-easy (Promega) to make pGEMS2 and sequenced to confirm the deletion. pONY2.13lacZDS2 is made by cutting out the 1.1 kb S2 region from pGEMS2 with Cel II and ligating it into pONY2.13lacZ.

Gagpol Construct

The same region of S2 is deleted in pONY3 to prevent recombination between pONY3DS2 and pONY2.13DS2 reconstituting the S2 gene. pONY3DS2 is made by PCR amplification with SY1/SY2 and SY3/SY4 using pONY3 DNA as template. The two PCR products are pooled and PCR is carried out with primers SY1 and SY3. The 0.7 kb product is ligated into pGEMT-easy (Promega) to make pGEMS22 and sequenced to confirm the deletion. The 0.7 kb S2 coding region is excised of pGEMS22 with Not I and inserted into pBluescript KS+ (Stratagene) to make pBPCRS2. The Eco RV and Nco I fragment from pONY3 (2.2 kb) is inserted into pBPCRS2 cut with Eco RV and Nco I to make pBpONYS2. This is then cut with Eco RV and Cel II (2.9 kb fragment) and inserted into pONY3 cut with Eco RV and Cel II to thereby making pONY3DS2.

Construction of dUTPase Mutant pONY3DdUTPase is made by site directed mutagenesis of nucleotide 4176 from a T to an A residue (Payne et al., Virology, 210:302–313). This mutates the aspartic acid to a glutamic acid. This is done by PCR amplification using PCR primers dUTPaseF and dUTPaseR. The template DNA is pONY3. The PCR product is inserted into pGEMT-easy and sequenced to confirm the mutation. This is called pGDdUTPase. pONY3 is cut with Not I and Eco RV (4.6 kb) and inserted into pBluescript KS+ (Stratagene) to make pBEV. The pGDdUTase is cut with Pac I and Pst I and the 0.4 kb band inserted into pBEV cut with Pac I and Pst 1. This is called pONY3pBDUTPase. This is then inserted into pONY3 via Not I and Eco RV (4.6 kb) to make pONY3DdUTPase.

Construction of the S2 and dUTPase Double Mutant

To make the double mutant of pONY3 the construct pBpONYS2 is used. pGDdUTPase is cut with Pac I and Pst I and the fragment inserted into pBpONYS2 cut with Pac I and Pst I to make construct pS2DdUTPase. This is then cut with Eco RV and Cel II and inserted into pONY3 cut with Eco RV and Cel II to make pONY3DS2DdUTPase.

Analysis of S2 and dUTPase Mutants pONY2.13lacZDS2, pONY3DdUTPase and pONY3DS2DdUTPase vectors are used in a number of combinations in three plasmid co-transfections to generate virus as described for MLV-based vectors (Soneoka et al 1995 Nucl. Acids Res. 23:628–633) and the virus generated is titred on 293T and D17 cells, in either dividing or non-dividing states. Cells are arrested in $G_1/S$ phase by treatment with aphidicolin (9) and then transduced with EIAV-based and MLV-based vectors pseudotyped with VSV-G (Table 4). The transduction efficiency of the MLV vector is lower by four orders of magnitude in aphidicolin treated cells as compared to untreated cells. The incomplete block to cell transduction by MLV is probably due to a small population of dividing cells. In contrast, no significant difference is observed in the case of the EIAV-based vectors. This demonstrates that the EIAV-based system does not require S2 or dUTPase either for production or transduction. Payne et al., (Payne et al., Virology, 210:302–313) and others have shown that EIAV dUTPase is required for the infection of horse macrophages. This may represent a restriction in infection of macrophages by EIAV.

The properties of the S2 and dUTPase mutants are tested by transduction of hippocampal embryonic day 14 neuronal cells cultured in minimal media for 7 days. No significant difference is found between the various EIAV vectors. However a much reduced transduction efficiency is seen for the MLV vector. This indicates that S2 and dUTPase is not required for the transduction of physiologically non-dividing cells.

In summary we can conclude that tat, S2 and dUTPase are not required in any part of the vector system for vector production or transduction.

EXAMPLE 8
Addition of Rev/RRE

The construction of pEGASUS-1 has been described above. This vector contains 759 bp of EIAV sequence. The introduction of the EIAV RRE (0.7 kb) into pEGASUS-1 to produce pEGASUS/RRE resulted in a four-fold increase in the titre when Rev is provided in trans (Table 2). This vector now contains, 1.47 kb of EIAV.

EXAMPLE 9
Construction of Improved Gagpol Expression Plasmids

In pONY3 there is an extended 5' untranslated region before the start of the gagpol coding sequence. It is likely that this unusually long sequence would compromise expression of the gagpol cassette. To improve gagpol expression pONY3 is modified to remove the remaining 5' LTR. This is done by cutting pONY3 with Nar I and Eco RV. The 2.4 kb fragment is inserted into pBluescript KS+ (Stratagene) at Cla I and Eco RV sites to make construct pBSpONY3.0. pBSpONY3.0 is cut with Xho I and Eco RV. The 2.4 kb fragment is inserted into pONY3 at Xho I and Eco RV to make pONY3.1.

Figure 10:
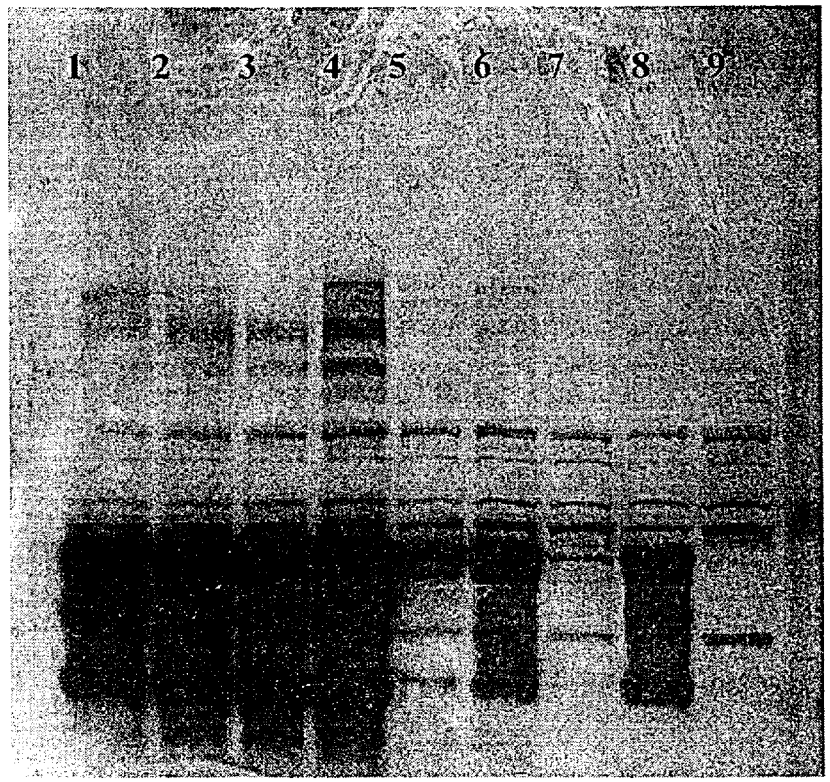
FIG. 10 shows analysis of gagpol expression constructs. 30 μg of total cellular protein was separated by SDS/PAGE, transferred to nitrocellulose and probed with anti-EIAV antibodies. The secondary antibody was anti-Horse HRP (Sigma). Titers were averaged from three independent experiments and calculated as lacZ forming units per ml. There was no more than 10% variation between experiments. pONY2.1nlslacZ and the envelope expression plasmids were co-transfected with the EIAV gagpol.

This manipulation removes the 5' LTR up to the Nar I site within the primer binding region (386nt). This construct gives a two fold increase in titre and increased protein expression (FIG. 10).

pONY3.1 like pONY3 encodes gag, gagpol, Tat, S2 and Rev. Since the S2 mutation experiments showed that S2 is not required either in the production system or in the EIAV vector genome it is possible to design a gagpol expression constructs without S2. Two such constructs, pHORSE and pHORSE3.1, are produced.

pHORSE is made by PCR amplification with EGAGP5'OUTER/EGAGPINNER3 and EGAGP3'OUTER/EGAGPINNER5 using pONY3 as template DNA. The two PCR products are purified pooled and re-amplified using primers EGAGP5'OUTER/EGAGP3'OUTER. This product is inserted into the Xho I and Sal I sites of pSP72 to make pSP72EIAVgagpolO'lap. pONY 3 is cut with Pvu II and Nco I and the 4.3 kb fragment is inserted into pSP72EIAVgagpolO'lap cut with Pvu II and Nco I to make pSPEGP. This is cut with Xho I and Sal I (4.7 kb) and inserted into pCI-Neo at the Xho I and Sal I sites. This construct is called pCIEGP. The RRE is cut out from pEGASUS with Sal I (0.7 kb) and inserted into pCIEGP construct at the Sal I site to make pHORSE.

When this construct is assayed for protein expression in the presence or absence of pCI-Rev (a construct expressing the EIAV Rev open reading frame, see above) it is found to be Rev dependent as expected. However, protein expression is much lower than from pONY3.1. In addition when used in virus production the titre is found to be 100 fold lower than that from pONY3.1.

Unexpectedly when the leader sequence (comprising sequences from the end of U5 of the 5'LTR to the ATG start of gag 383–524nt) of pONY3.1 is inserted into pHORSE, to make pHORSE3.1, protein expression and virus production improved. pHORSE3.1 is made by replacing the 1.5 kb Xho I/Xba I of pHORSE with the 1.6 kb Xho I/Xba I of pONY3.1. Titres obtained with pHORSE3.1 are similar to that of pONY3.1. The reason for the slightly lower titre of pHORSE3.1 compared to pONY3.1 may be due the requirement for a four plasmid co-transfection with pHORSE3.1 (due to the Rev dependence of this system). We can conclude therefore that a minimal EIAV vector system should have this leader for maximum gagpol expression.

When pHORSE3.1, pRV67, pCIRev and pEGASUS/RRE are used in a four plasmid co-transfection (Table 6) virus is produced at a high titre ($2.0 \times 10^4$ l.f.u./ml). This system lacks the second exon of Tat which is responsible for Tat transactivation (Southgate et al., J. Virology, 1995, 69:2605–2610). This demonstrates that the Tat is not required for the EIAV-based vector system.

By engineering the backbone of pHORSE3.1 to express Rev (replacing the Neo open reading frame with that of EIAV Rev) the requirement of a four plasmid co-transfection was eliminated. This was done by cutting pCI-Neo with Stu I and Bst XI and filling in the 5' overhangs with T4 DNA polymerase. This produced a vector fragment of 4.6 kb into which the Rev open reading frame from pTopoRevpos (cut with Sac I and Xba I giving a 0.6 kb band in which the 5' overhangs were filled in using T4 DNA polymerase) was inserted. This was called pCREV. The EIAV gagpol reading frame including the RRE and leader was cut from pHORSE3.1 with Xho I and Not I (5.5 kb) and inserted into pCREV at the Xho I and Not I sites to make pEGPR3.1.

Codon optimisation of the EIAV gagpol should eliminate the dependence of gagpol protein expression on the RRE/Rev system. The need of pEGASUS-1 for Rev/RRE can also be eliminated by using a heterologous RNA export system such as the constitutive transport element (CTE) from Mason-Pfizer Monkey virus (MPMV) (Bray et al., PNAS, 1994, 91:1256–1260, Kim et al., 1998)

TABLE 4

| Vector | gagpol | Titre on D17 cells (l.f.u./ml) Dividing | Non-dividing | Ratio (Non-dividing/dividing) |
| --- | --- | --- | --- | --- |
| S2+ | S2+, dUTPase+ | $2.2 \times 10^5$ | $1.1 \times 10^5$ | 0.5 |
| S2− | S2+, dUTPase+ | $1.5 \times 10^5$ | $1.3 \times 10^5$ | 0.9 |
| S2− | S2−, dUTPase+ | $1.0 \times 10^5$ | $1.2 \times 10^5$ | 1.2 |
| S2− | S2−, dUTPase− | $1.5 \times 10^5$ | $1.6 \times 10^5$ | 1.1 |
| S2+ | S2−, dUTPase+ | $2.2 \times 10^5$ | $2.3 \times 10^5$ | 1.0 |
| S2+ | S2−, dUTPase− | $1.5 \times 10^5$ | $1.4 \times 10^5$ | 1.0 |
| S2+ | S2+, dUTPase− | $1.5 \times 10^5$ | $1.4 \times 10^5$ | 1.0 |
| MLV Vector | | $1.2 \times 10^7$ | $6.7 \times 10^3$ | 0.0006 |
| Mock | | <1 | <1 | 1 |

TABLE 5

Comparison of pONY2.10LacZ and pEGASUS +/−EIAV RRE.

| Vector Genome | Gagpol | Titre (l.f.u./ml) |
| --- | --- | --- |
| pONY2.10LacZ | pONY3.0 | $7 \times 10^4$ |
| pEGASUS | pONY3.0 | $2.2 \times 10^4$ |
| pEGASUS/RRE | pONY3.0 | $8.6 \times 10^4$ |

Titres with Rev are higher for pEGASUS-1 even though it has no RRE. Possibly the effect of REV is via enhanced expression of gagpol.

TABLE 6

| Vector Genome | Gagpol | Titre (l.f.u./ml) |
| --- | --- | --- |
| pONY2.11lacZ | pONY3.1 | $1.7 \times 10^5$ |
| pONY2.11lacZ | pHORSE3.1 | $9.0 \times 10^4$ |
| pEGASUS/RRE | pONY3.1 | $8.0 \times 10^4$ |

TABLE 6-continued

| Vector Genome | Gagpol | Titre (l.f.u./ml) |
|---|---|---|
| pEGASUS/RRE | pHORSE3.1 | $2.0 \times 10^4$ |

Transfections were carried out in 293T cells with pCI-Rev and pRV67. The virus was titred on D17 cells
Primers

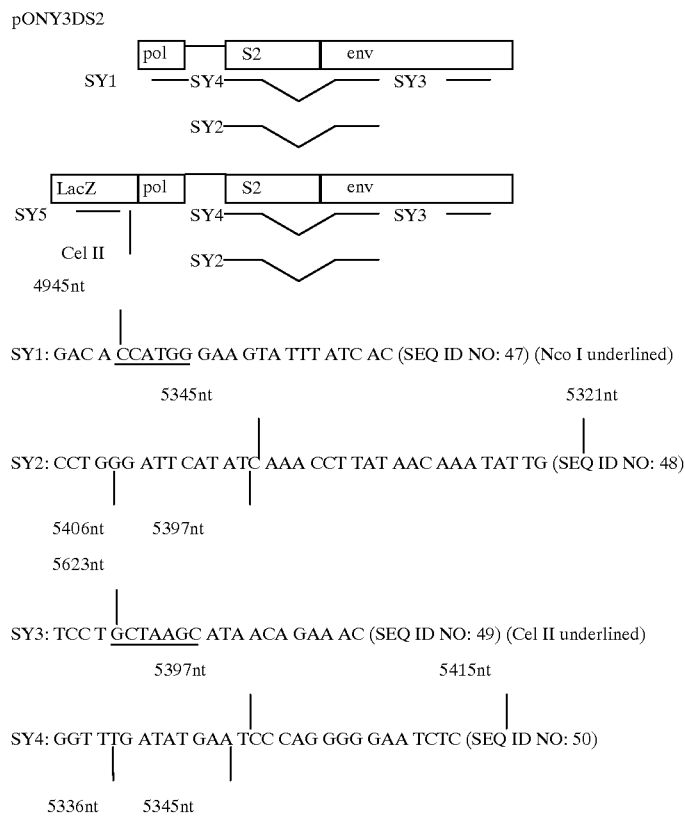

SY1: GAC A CCATGG GAA GTA TTT ATC AC (SEQ ID NO: 47) (Nco I underlined)

SY2: CCT GGG ATT CAT ATC AAA CCT TAT AAC AAA TAT TG (SEQ ID NO: 48)

SY3: TCC T GCTAAGC ATA ACA GAA AC (SEQ ID NO: 49) (Cel II underlined)

SY4: GGT TTG ATAT GAA TCC CAG GGG GAA TCTC (SEQ ID NO: 50)

SY5: ACCC CGTACG TCT TCC CGA GCG (SEQ ID NO: 51) (Sun I underlined)

dUTPaseF: GTTA TTAATTAATGGAGGAATAATTGAAGAAGGATATAC (SEQ ID NO: 52) (Pac I underlined) (The base in bold is the single base change from T to A that inactivated the dUTPase).

dUTPaseR: TCTT CTGCAGGTCCTGATCCTTGCTTAGTGC (SEQ ID NO: 53) (Pst I underlined)

S2StopR: GACCATGTTACCCCTTTACCATTAACTC-CCTAATATCAAAC (SEQ ID NO: 54) (The bases in bold are the base changes from TATGG to TTAGG that remove the start codon of S2).

S2StopF: GTAAAGGGGTAACATGGTCAGCATCG-CATTCTACGGGGAATCC (SEQ ID NO: 55) (The base in bold is the base change from TATGG to TACGG that remove the start codon of S2).

EGAGP5'OUTER: CCATGCACGT CTCGAGCCAGCATGGGAGACCCTTTGAC (SEQ ID NO: 56) (Xho I underlined)

EGAGP3'OUTER: CGAGCTAGAG GTCGACTCAATTTGGTTTATTAGTAAC (SEQ ID NO: 57) (Sal I underlined)

EGAGPINNER3: GCAATGGAATGACATCCCT CAGCTGCCAGTCC (SEQ ID NO: 58) (Pvu II underlined)

EGAGPINNER5: GGGATGTCATTCCATTGCCA CCATGGGAAGTATTTATCACTA (SEQ ID NO: 59) (Nco I underlined)

EXAMPLE 10 pONY4 Series of Vectors

In order to eliminate the use of Tat for the transcription of the EIAV genome and increase the amount of full length transcript the EIAV U3 (5' LTR) was replaced with the HCMV enhancer/promoter as in the case of the pEGASUS vectors (Example 2).

Plasmid construction pONY2.11 lacZ contains a deletion in gag such that only 373 bp of the gag ORF remains. pONY4 was made by replacing the 5' LTR with the CMV LTR from pEGASUS-1. pEGASUS-1 was cut with Bgl II/Xho I releasing a 3.2 kb fragment (containing the CMV LTR) which was inserted into pSP72 cut with Bgl II/Xho I. This construct was named pSPPEG213. This was cut with Hpa I/Nar I and the 1.3 kb fragment (encompassing the CMV LTR) was inserted into pONY2.11lacZ cut with Nae I/Nar I. pONY4.1 contains a deletion (2.1 kb) downstream of the lacZ gene (between the Sfu I and Sal I sites) such that tat, S2, env, rev and RRE, are either missing or severely truncated (FIG. 11c). pONY4.1 was made by cutting it with Sfu I/Sal I, blunt-ended by Klenow polymerase and religated. pONY4G was made by replacing the lacZ gene of pONY4 (Sac II/Kpn I and then blunting with Klenow polymerase) with that of GFP from pEGFP-Nl (Clontech) (Bam HI/Xba I and then blunting with Klenow polymerase) as a blunt fragment.

Production and Assay of Vectors

Vector stocks were generated by calcium-phosphate transfection of human kidney 293T cells plated on 10 cm dishes with 16 µg of vector plasmid, 16 µg of gag-pol plasmid and 8 µg of envelope plasmid. 36–48 h after transfection, supernatants were filtered (0.45 µm) aliquoted and stored at −70° C. Concentrated vector preparations were made by ultracentrifugation of at 20 000 rpm (SW40Ti rotor) for 90 min, at 4° C. The virus was resuspended in PBS for 3–4 h aliquoted and stored at −70° C. Transduction was carried out in the presence of polybrene (8 µg/ml). It was consistently observed that pONY2.11lacZ gave about 2 to 4 fold higher titres than the less deleted pONY2.10lacZ. When U3 in the 5' LTR was replaced with the CMV enhancer /promoter as in pONY4 then titres increase a further 5 to 10 fold.

EXAMPLE 11
EIAV 'Self-inactivating' Vectors (SIN-vectors)

The expression of the transgene from EIAV vectors in particular cell types may be influenced by elements in the LTR's. To remove such elements SIN (Self Inactivating) vectors can be constructed however the precise configuration of the vector may be influenced by the requirement to maintain certain sequences necessary for efficient production of the vector (Mol Cell Biol 1996 September;16(9):4942–51. RNA structure is a determinant of poly(A) site recognition by cleavage and polyadenylation specificity factor. Graveley B R, Fleming E S, Gilmartin G M) (J Virol 1996 March;70(3):1612–7. A common mechanism for the enhancement of mRNA 3' processing by U3 sequences in two distantly related lentiviruses. Graveley B R, Gilmartin G M). In addition SIN vectors provide a way for eliminating the production of full length transcripts in transduced cells.

Figure 12:
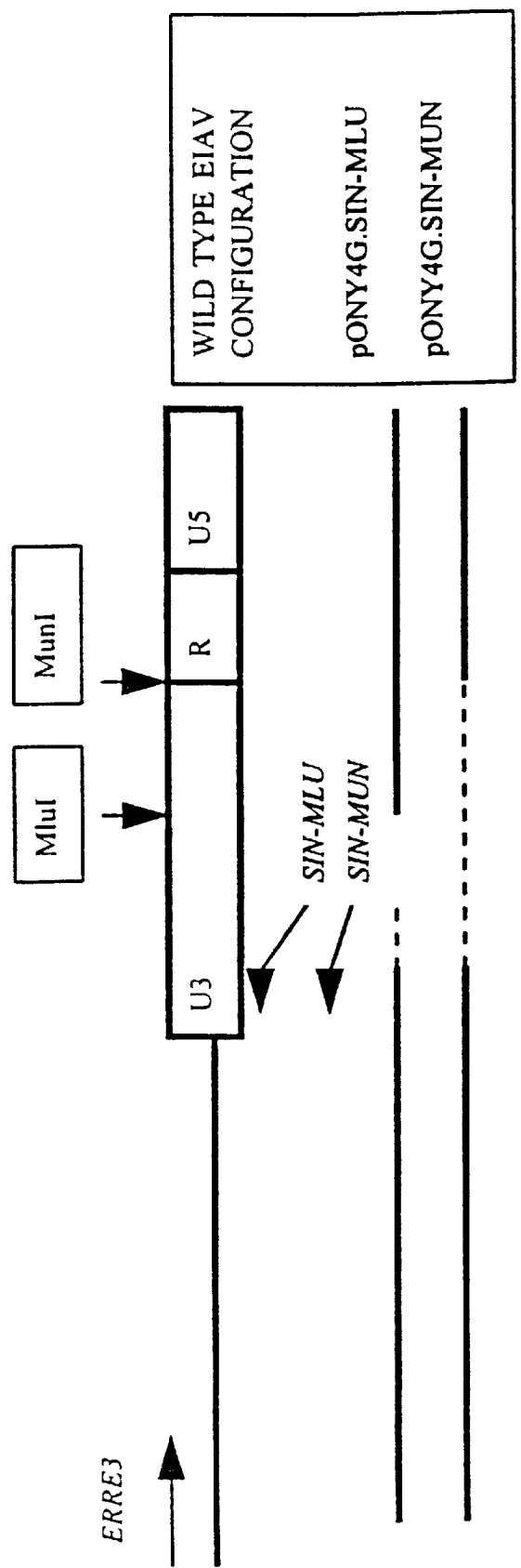
FIG. 12 shows two SIN vectors.

Two SIN vectors were made: one containing the putatively important sequences (for polyadenylation), located between the Mlu I and Mun I sites and one in which these sequences were deleted. The 5' border of the deletions was 112 bases from the 5' end of the U3 region of the 3 'LTR. The structure of two SIN vectors is shown in FIG. 12.

Deletions present in pONY4G.SIN-MLU and pONY4G.SIN-MUN vectors are indicated in dashed lines. Primers are shown in italic.

DNA sequences between nucleotides 7300 and 8079 (numbered according to EIAV clone pSPEAIV19, Accession No. U01866) were obtained using polymerase chain reaction amplification using pONY4G as template. The positive sense primer was ERRE3 and the negative primers for amplification were SIN-MLU (C7143: GTCGAG-CACGCGT*TTGCCTAGCAACATGAGCTAG* (SEQ ID NO: 60)(MluI site in bold) or SIN-MUN (C7142: GTC-GAGCCAATTG*TTGCCTAGC* (SEQ ID NO: 61) *AACATGAGCTAG* (MunI site in bold) where the underlined sequences are complimentary to nucleotides 8058 to 8079 (of pSPEIAV19). The PCR products were digested with NspV and either MluI or MunI respectively. These were then ligated into pONY4G prepared for ligation by digestion with NspV (SfuI) and either MluI (partial digestion) or MunI respectively.

EXAMPLE 12
EIAV Vectors with Reverse Configuration Internal Promoter-reporter Cassettes In EIAV vectors such as pONY4Z or pONY4G the internal CMV-reporter cassette is orientated so that transcription from the 5'LTR and the internal promoter are co-directional and the polyadenylation signal in the 3'LTR is used for transcripts from both promoters. An alternative configuration is achieved by reversing the internal promoter-reporter cassette, however a polyadenylation signal must be placed downstream of the cassette.

An example of this 'reverse orientation' vector was made as follows. pONY4Z was digested with PstI and the overhanging termini trimmed back with T4 DNA polymerase. This was then used as the 'vector' fragment in a ligation with the MluI to AseI fragment from pEGFP-C1 which contains sequences including the CMV-GFP-SV40 early mRNA polyA signal cassette. Prior to ligation this fragment was flush-ended with T4 DNA polymerase. The vector encoding plasmid was called pONY4Greverse.

Vector particles were recovered from pONY4Greverse by co-transfection with pONY3.1 and pRV67, which express EIAV gag/pol and VSV-G protein respectively. The titre on D17 canine cells from pONY4Greverse was 13-fold lower than from pONY4G vector recovered in parallel.

The lower titre of pONY4Greverse was probably due to interference between the CMV promoters which drive transcription of the genome and the GFP towards each other however truncation of the genomic RNA by the SV40-derived polyadenylation signal present in the inserted CMV-GFP-polyA cassette could also have been a factor. An improved vector was made by replacing the polyadenylation signal of pONY4Greverse with the bovine growth hormone polyadenylation (BGHpA) signal. To make this improvement pONY4Greverse was digested with BstAPI and the ends flushed with T4 DNA polymerase, then cut with PstI. This 'vector' fragment was then ligated to a DNA fragment representing the BGHpA which was prepared from pcDNA3.1+ (Invitrogen) by digestion with SphI, and then the ends blunted with T4 DNA polymerase, then digested with PstI.

EXAMPLE 13
Construction and Use of poly.A Signals Containing Introns

In the pONY vectors described here the polyadenylation signal used is that from EIAV. This is found in the 3' LTR at the border of R and U5. This signal may not be optimal because it is not of a consensus sequence (see Whitelaw and Proudfoot 1986 EMBO 5; 2915–2922 and Levitt et al 1989 Gen. and Dev. 3; 1019–1025 for description of consensus polyadenylation signal).

Figure 13:
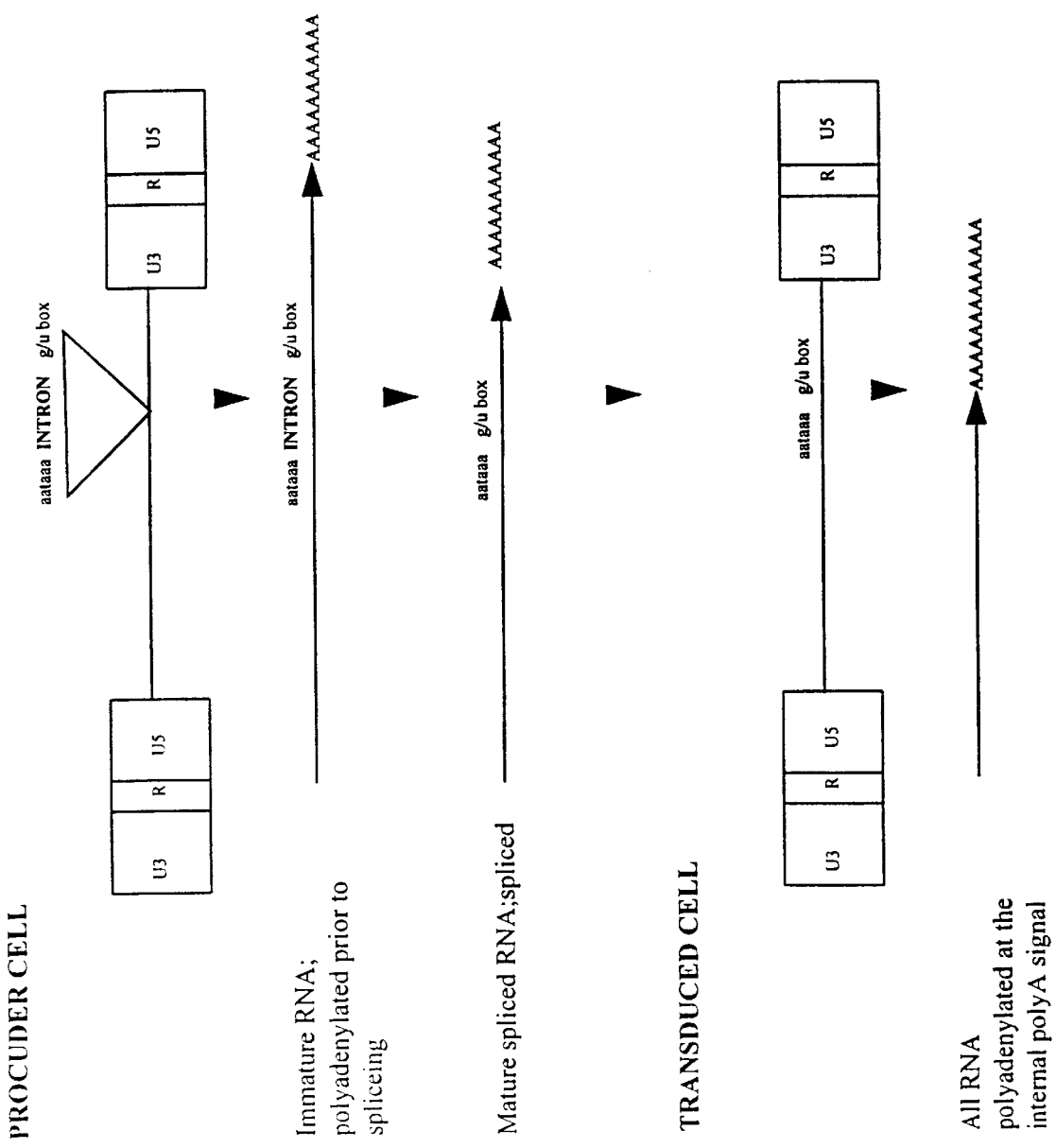
FIG. 13 is a representation of a vector with a split polyA signal.

One method of improving the viral polyadenylation is to replace the 3' LTR poly A signal with that of a consensus/strong polyadenylation signal. By such a method the signal would now be optimal in the producer cell. However upon transduction this signal is lost because during replication, the 5' LTR is the source of the poly A signal (see *Retroviruses* 1998 CSH press (Ed. J.Coffin) for review of retroviral life cycle). One novel way of overcoming the problem (of no strong polyadenylation signal upon transduction) is to include the poly A signal in a manner as will now be outlined: The method is to use a 'split poly-A signal' where by an intron splits the aataaa motif from that of the essential g/u box. Such a signal has previously been used by Liu et al (1993 N.A.R 21;5256–5263) to demonstrate both that large gaps between the aataaa and the g/u box will disable the poly A signal and that the polyadenylation process preceeds splicing. By placing a split-polyA signal within the retroviral vector such a signal will not be functional until transduction of target cells. This is because polyadenylation preceeds splicing and as such the upstream split-polyA signal will not be used during vector expression within the producer cell. Outlined in FIG. 13 is a schematic representation of how such a retroviral vector, containing a split polyA signal, would function—both in producer and in transduced cells. First this Figure demonstrates that although there exists an upstream consensus polyadenylation signal, the initial vector transcripts are still polyadenylated at the usual 3' LTR using either a viral or other poly A signal as so desired. This is because although the upstream poly A signal is functional in the final vector genome, this signal is not read by the polyadenylation machinery because it is created only during intron removal and thus not present in the primary RNA transcript. Second, this figure demonstrates that upon transduction the resulting vector transcripts are now polyadenylated at the first signal; this being now a normal strong polyadenylation signal with no introns to distance the essential aataaa and g/u box.

Figure 14:
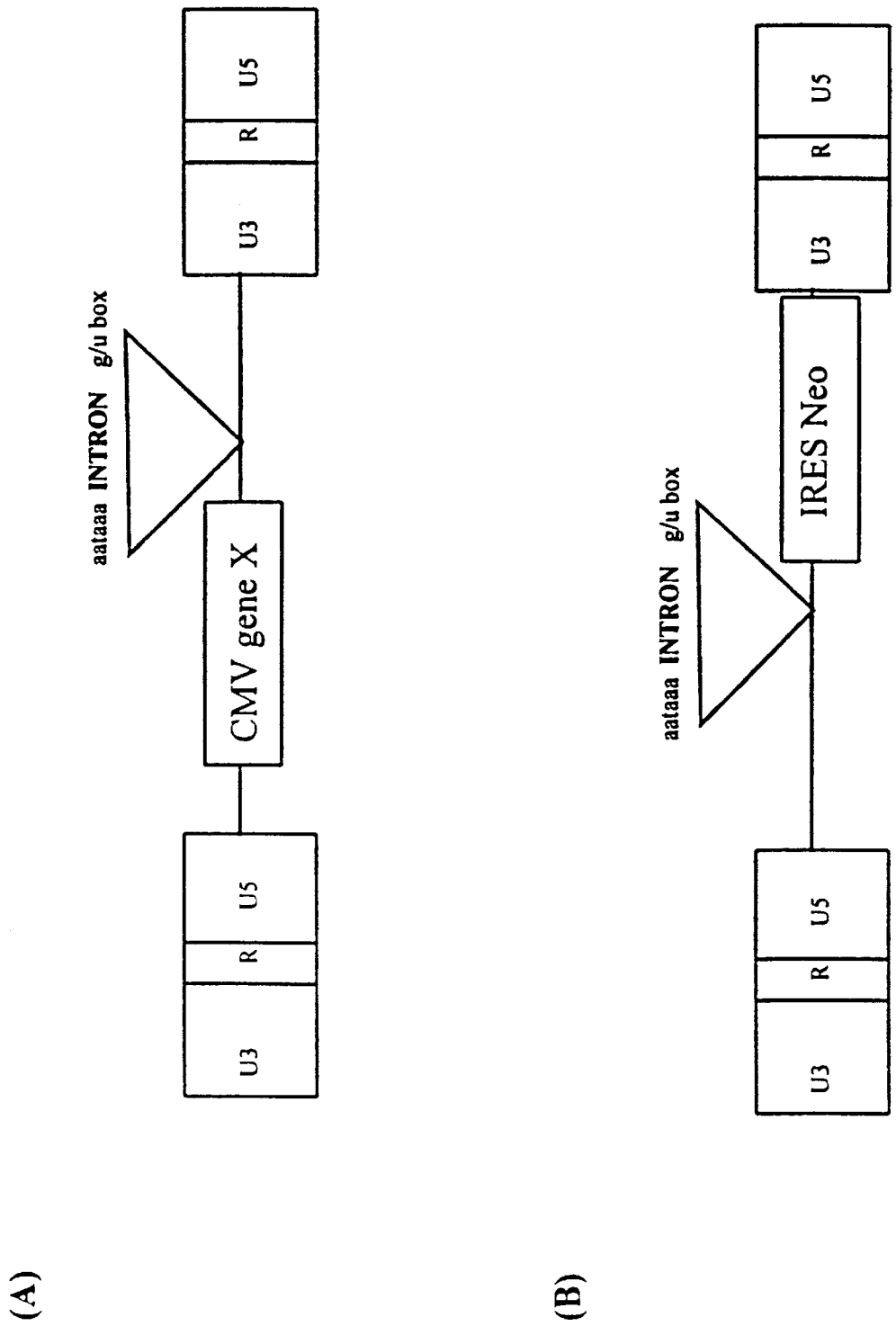
FIG. 14 is a representation of a vector with a split polyA signal.

There are a number of advantages to inclusion of such a split-poly A signal within a retroviral vector; these include the following:
(1) The use of strong non-viral based polyadenylation signal within the transduced cell will enhance gene expression within such cells.
(2) The use of such poly A signals upstream of the natural LTR (see FIG. 13) based signals will, upon transduction, generate shorter RNA transcripts that contain less viral sequence at their 3' end and as such will not be able to undergo subsequent retroviral reverse transcription. Indeed if the desired gene is expressed from an internal promoter such as the CMV, rather than an LTR; the resulting transcript expressed in the transduced cell could be designed to contain no viral sequence at all (see FIG. 3A).
(3) Inclusion of such a signal upstream of the 3'LTR will mean expression of the RNA downstream to the split poly A signal will be limited only to the producer cell because such RNA will not be transcribed in the transduced cell. This will therefore restrict certain sequence expression (for example IRESneo; see FIG. 14B) to producer cells.
(4) The presence of an intron within the producer cell will help with nuclear export of vector RNA from the nucleus.
(5) Because upon transduction their now exists an internal functional poly A signal, the viral poly A signal in the 5' LTR (the one copied to the 3' position during reverse transcription) can be removed/deleted if desired. This is of use for preventing the process of promoter-proximal polydenylation from the 5' LTR in the producer cell (see Scott and Imperiale 1997 (Mol. Cell. Biol. 17;2127–35) and thus encourage full length transcript production of the virus.

EXAMPLE

Figure 15:
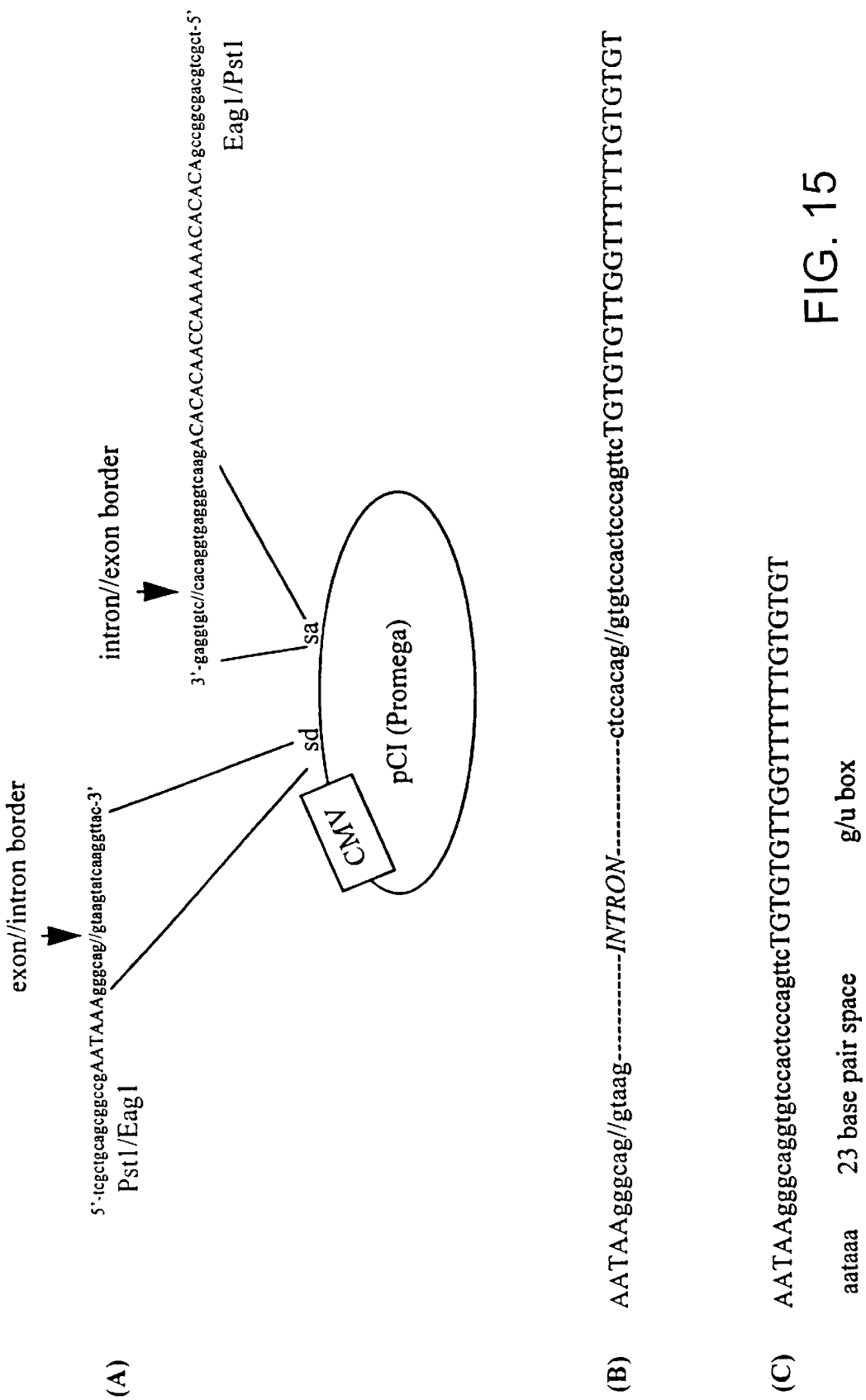
FIG. 15 is a representation of a vector with a split polyA signal. A. SEQ ID NOs: 2 and 3. B SEQ ID NO: 4. C. SEQ ID NO: 5.
Figure 16:
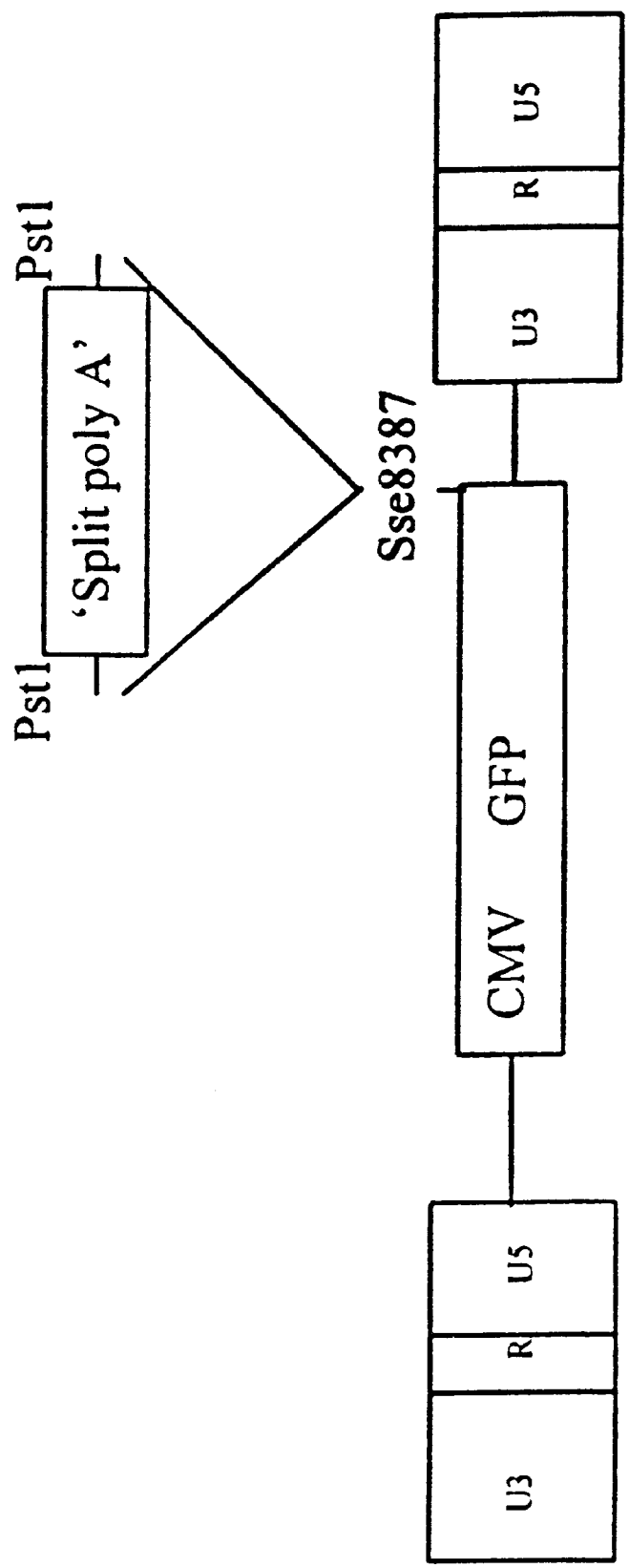
FIG. 16 shows construction of pONY4-GFP with a split polyA signal.

To demonstrate the use of such a signal in a retrovirus; the "split poly A signal" cassette is constructed as described in FIG. 15; with the intronic sequence being derived from pCI (Promega). Once made this cassette is cloned into the pONY 4 GFP vector using the Pstl compatible unique sse8387 site of pONY4-GFP (see FIG. 16). Upon transduction the resulting vector will now polyadenylate prior to the 3'LTR and consequently no viral RNA 3' to lacZ will be transcribed (see FIG. 16).

EXAMPLE 14
Construction of MLV/EIAV Vectors

By replacing the EIAV LTR sequences with the MLV equivalents, the pONY vectors will no longer possess functional tar elements within the repeat regions (R) and as a consequence the U3 promoter will function without the requirement of Tat in the transduced cell.

Figure 17:
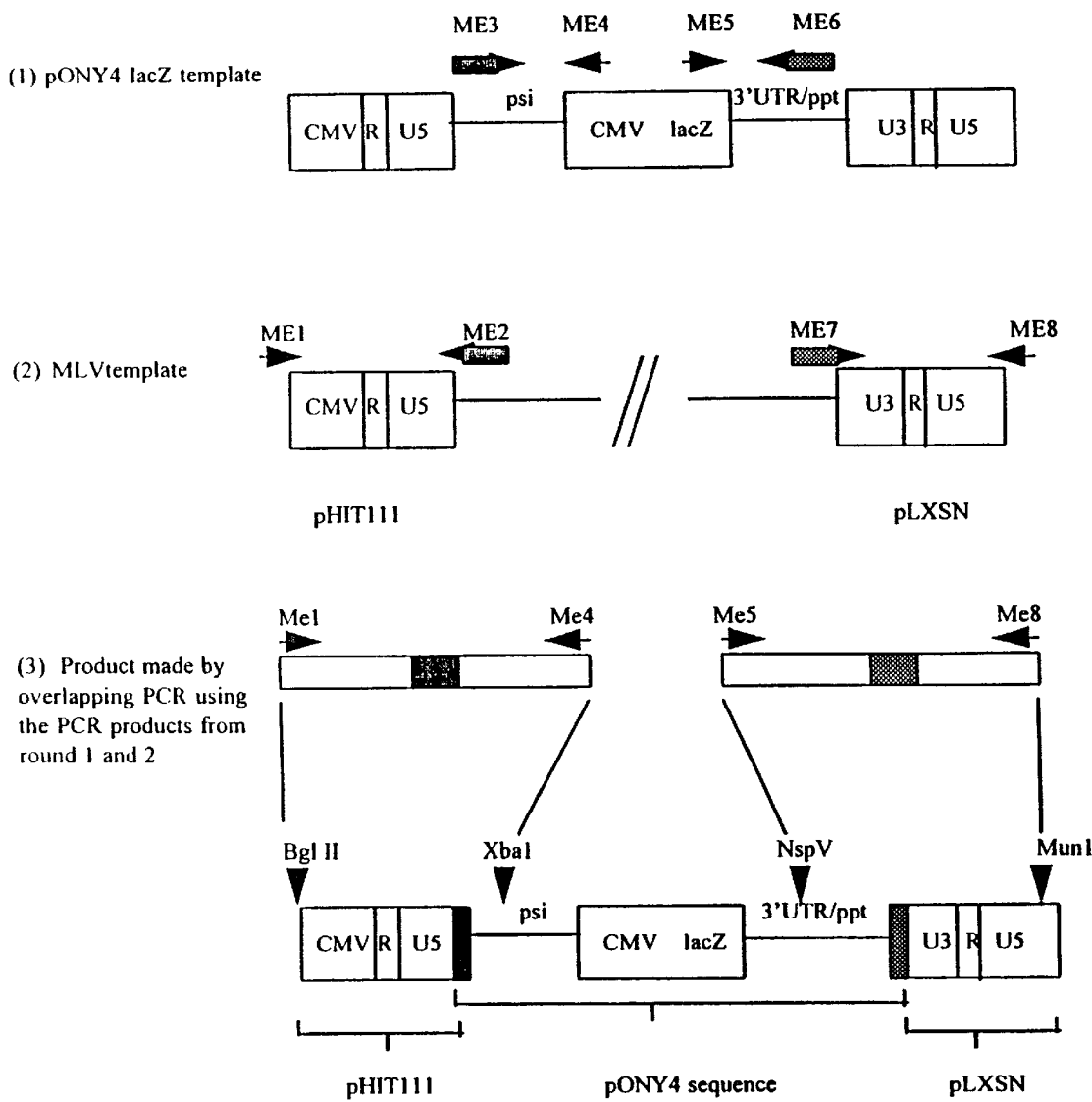
FIG. 17 shows construction of a MLV/EIAV vector.
Figure 19:
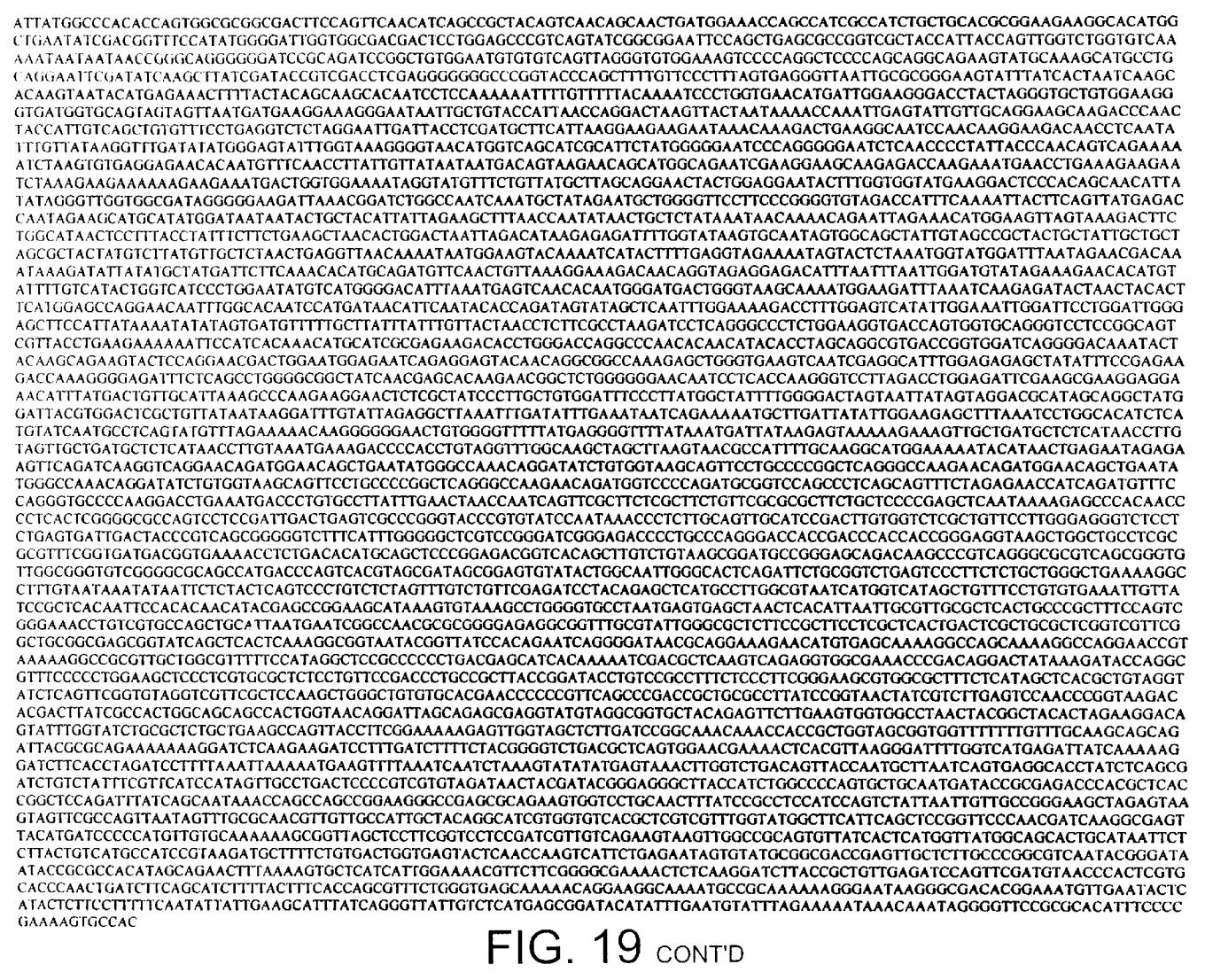

Outlined in FIG. 17 is how such a vector is made by overlapping PCR with primers described in FIG. 18. Primers Me1 and Me2 are used to amplify a PCR product from the MLV vector pHIT 111 (Soneoka et al 1995 NAR 23;628–633) whilst Me3 and Me4 are used to amplify a product from pONY4 lacZ. The resulting two products are then combined in a primerless PCR reaction to overlap them (homology between the two products is shaded in FIG. 17). The final full length product is cut BglII and Xbal and used to replace the BglII-Xbal fragment of pONY4 lacZ (containing the CMV/R/U5) to make pONY4-5'MLV. The resulting vector now has the CMV/R/U5 sequence from MLV linked to the EIAV U5 sequence (sequence required for genome recognition by intergrase prior to intergration). The next step involves PCR amplification with primers Me5 and Me6 from pONY4 LacZ template and PCR amplification with Me7 and Me8 from pLXSN template (Miller and Rosman 1989 Biotechniques 7:980–990). These two PCR products are then overlapped by primerless PCR (homology between primers shown as hatched box) and the resulting fragment cut with NspV and Munl and inserted into the NspV/Munl sites of pONY4-5'MLV; thus replacing the 3'EIAV LTR with a 3'MLV LTR fused to the 3'UTR/ppt/U3 intergrase binding site of pONY 4 lacZ. The resulting plasmid, named pONY-MOUSE (see FIG. 19 for complete DNA sequence), titres at $10^{4-5}$ per ml when combined with pONY3.1 and pRV67 in the HIT system.

EXAMPLE 15
Early Promoter Driving Lentiviral Vector Genome

In this example an EIAV genome is expressed from a vaccinia early promoter P7.5E (Davison 1989a). The promoter has been engineered to produce an EIAV genome with the correct 5' RNA end. In addition the vaccinia early termination sequence has been inserted downstream of the EIAV genome. This is inserted into the transfer plasmid pSC65, which can homologously recombine into the TK region of the MVA genome. Recombinant viruses can be selected by their lack of sensitivity to BudR (Earl et al. 1998).

Figure 11:
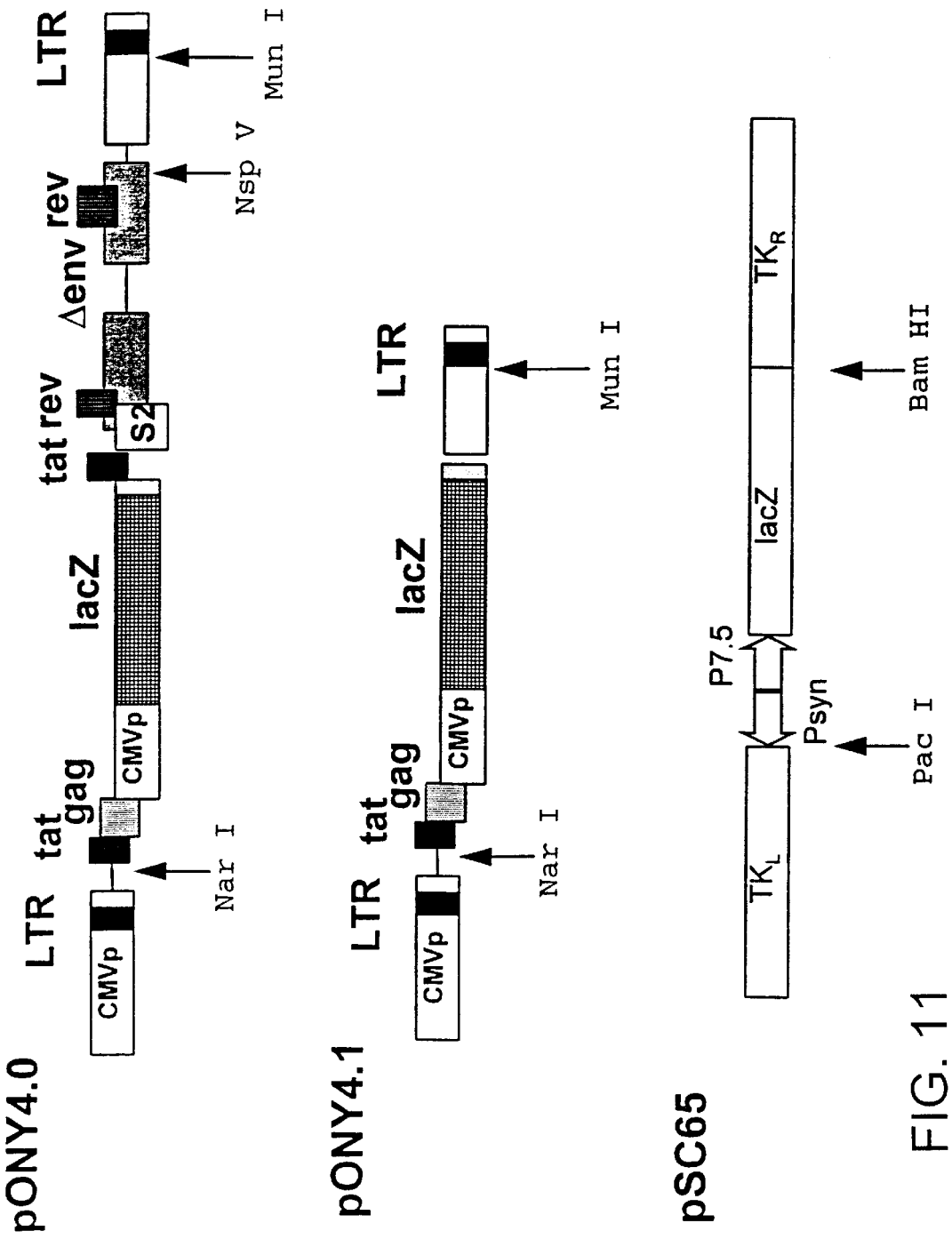
FIG. 11 shows examples of the pONY4 vectors.

FIG. 11 is a schematic representation of the EIAV genome vectors pONY4.0 and pONY4.1 which have been described in Example 10 and the vaccinia transfer vector pSC65 (Chakrabarti et al 1997). The P7.5E sequence is AAAAG-TAGAAAATATATTCTAATTTATT (SEQ ID NO: 62). The Early termination sequence for the early promoters is TTTTTNT (N=any nucleotide) (Fields).

Figure 20:
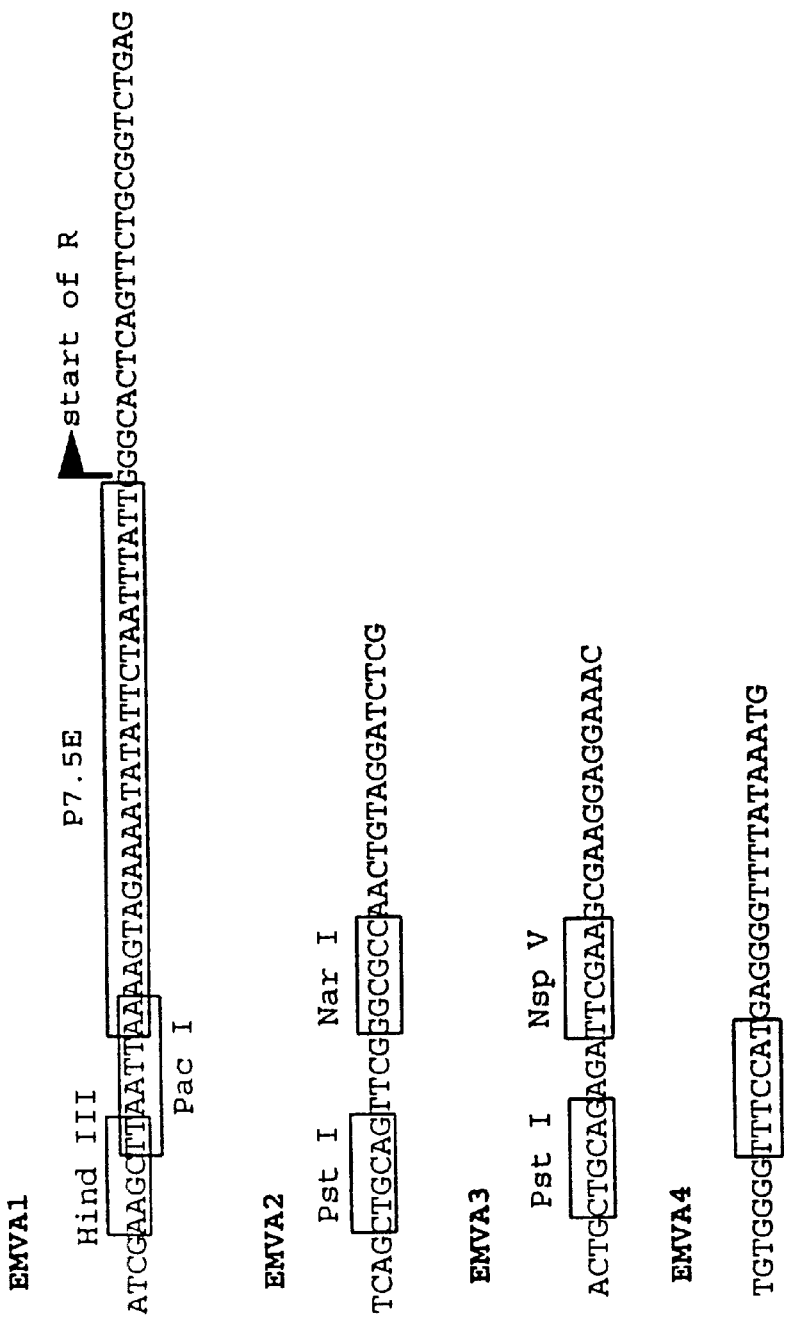
Figure 22:
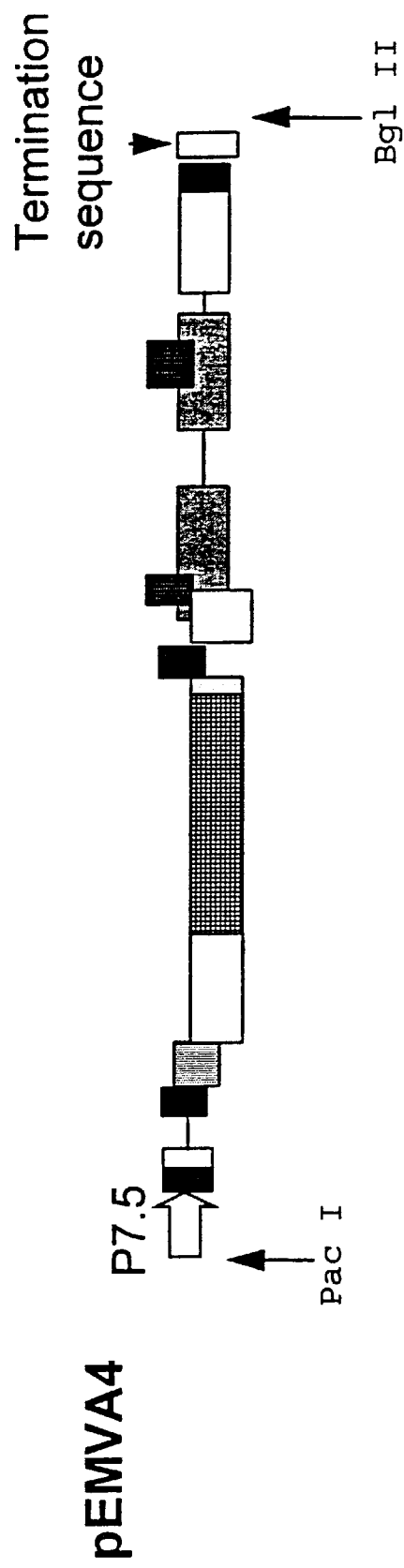
FIG. 22 shows pEMVA4 (after PCR with primers EMVA 1–8).
Figure 23:
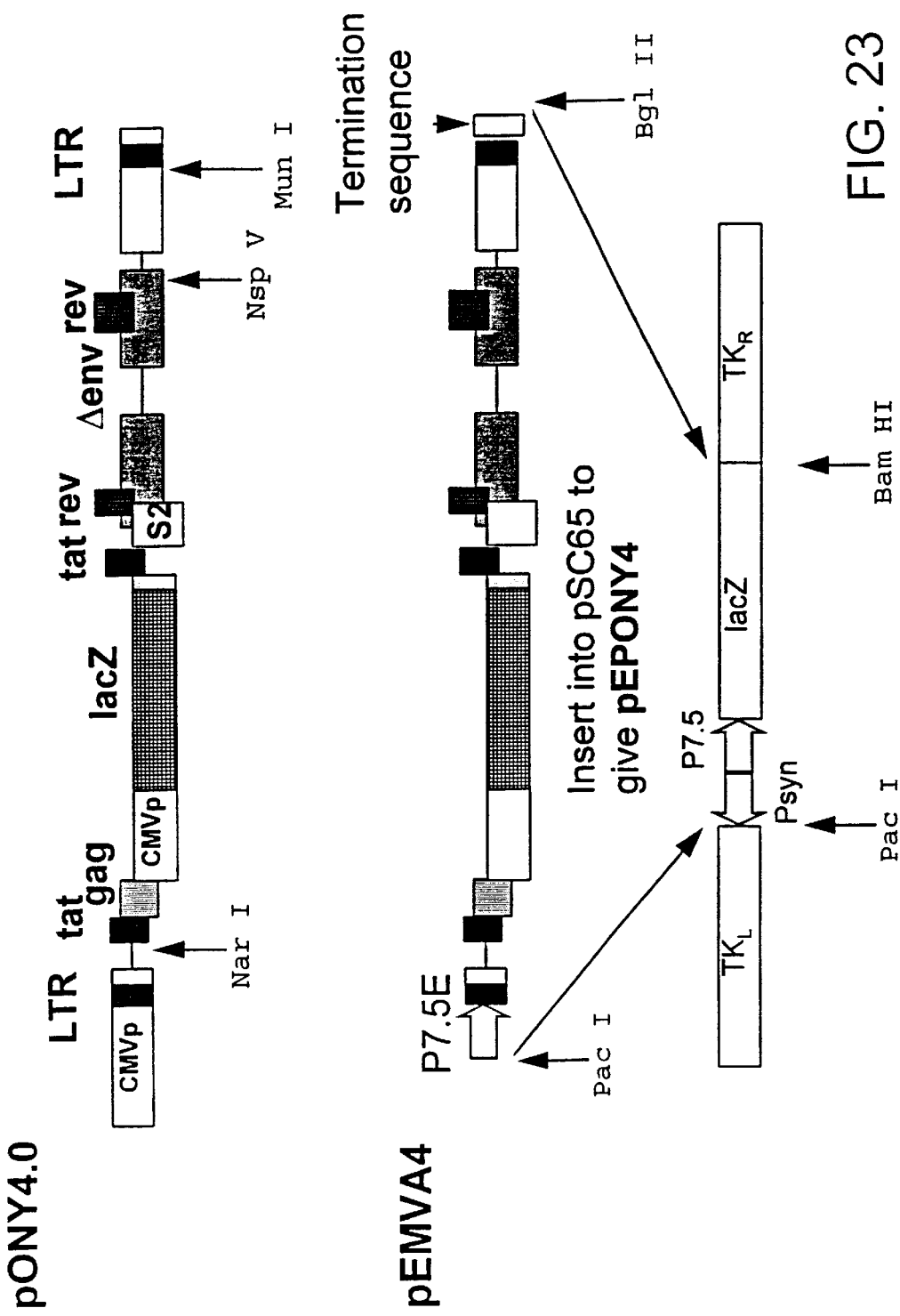
FIG. 23 shows pEMVA4.

The DNA manipulations are as follows and FIGS. 20 and 21 give the sequence of the PCR primers. PCR with primers EMV A1/2 produces the 5' LTR with the U3 region replaced by the P7.5E promoter. This is inserted into the plasmid pSP72 (Promega) using the Hind III/Pst I sites to make pEMVA1. EIAV U3 contains a sequence matching the criteria for vaccinia early termination (TTTTTAT). Using primers EMVA3/4 and EMVA5/6 and overlapping PCR this region is mutated to TTTCCAT in order to prevent early termination. This PCR product is inserted into the pEMVA1 using the Bgl II/Pst I sites to generate pEMVA2. A termination sequence (TTTTTTTTT) is inserted downstream of the 3' LTR R region using primers EMVA7/8. This PCR product is inserted into pEMVA2 using the Mun I/Bgl II sites making pEMVA3. Into this plasmid the rest of the EIAV vector genome (pONY4) is inserted via the Nar I/Nsp V sites making pEMVA4 (FIG. 22). This is then cut with Pac I/Bgl II and inserted into pSC65 cut with Pac I/Bam HI to make pEPONY4 (Bgl II and Bam HI are compatible) (FIG. 23). This removes the two vaccinia promoters and the lacZ coding cassette from pSC65.

Figure 24:
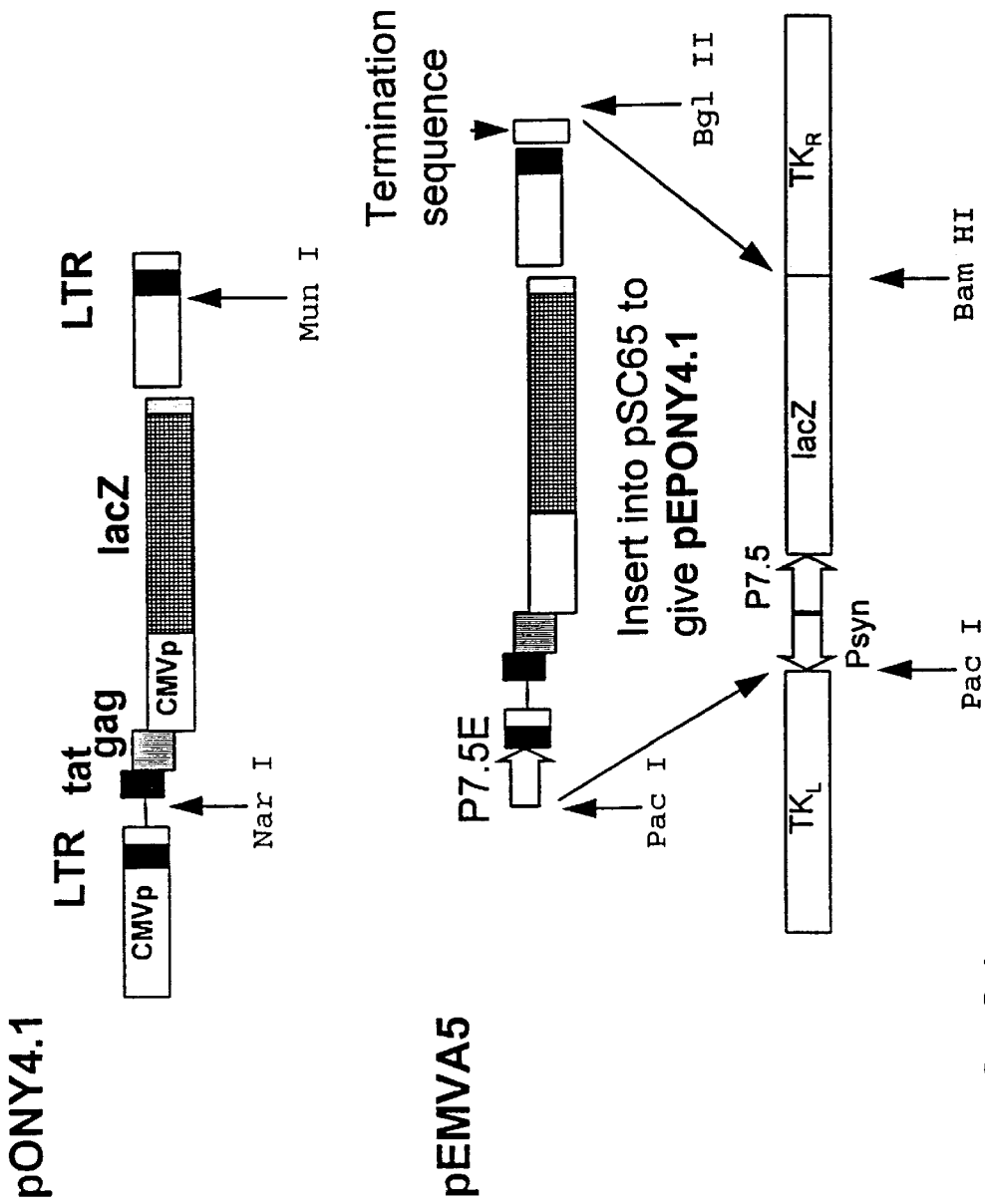
FIG. 24 shows pEMVA5.

In order to make the minimal EIAV genome version of this construct that is analogous to pONY4.1, pEMVA4 is cut with Sal I/Nsp V blunt ended and religated to make pEMVA5 (FIG. 24). This removes much of the sequence between the end of the lac Z gene and the end envelope region, hence this vector is Tat, Rev, S2 and Env minus. This is described in Example 10. This is then cut with Pac I/Bgl II and inserted into pSC65 cut with Pac I/Bam HI to make pEPONY4.1 (Bgl II and Bam HI are compatible) (FIG. 24). This removes the two vaccinia promoters and the lacZ coding cassette from pSC65.

Both pEPONY4.0 and pEPONY4.1 are suitable for inserting the genome expression cassettes into the TK region of the MVA genome (Carroll M W and Moss B Virology 1997 November 24;238(2):198–211) using a BHK TK-ve cell line (ECACC 85011423) and standard procedures for the construction of recombinant poxviruses (Earl et al 1998a & 1998b)

EXAMPLE 16
Synthetic Early/late Promoter Driving Lentiviral Vector Genome

The synthetic early/late promoter of vaccinia has a requirement for sequences downstream of the RNA initiation site (Davison 1989b). For this promoter to be used to generate a retroviral genome either the R regions have to be modified or a ribozyme is used to make the correct 5' end. Modifying the R regions is problematic as the initiation site has not been conclusively identified and varies with the sequence (Davison 1989b). Below is described the generation of a transfer plasmid that expresses the EIAV genome from the synthetic early/late promoter (Psyn). Downstream of this promoter is inserted a ribozyme that ensures the creation of the correct 5' end of the RNA. This construct also contains the early termination sequence.

Figure 26:
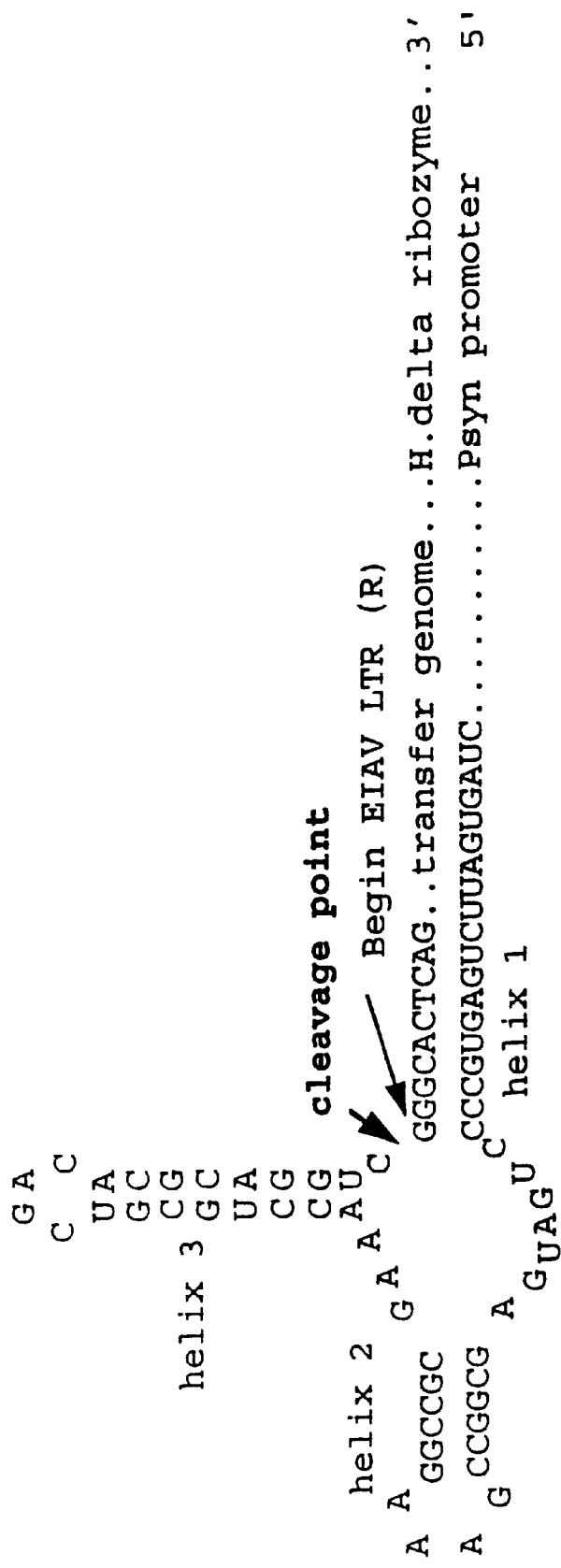
Figure 27:
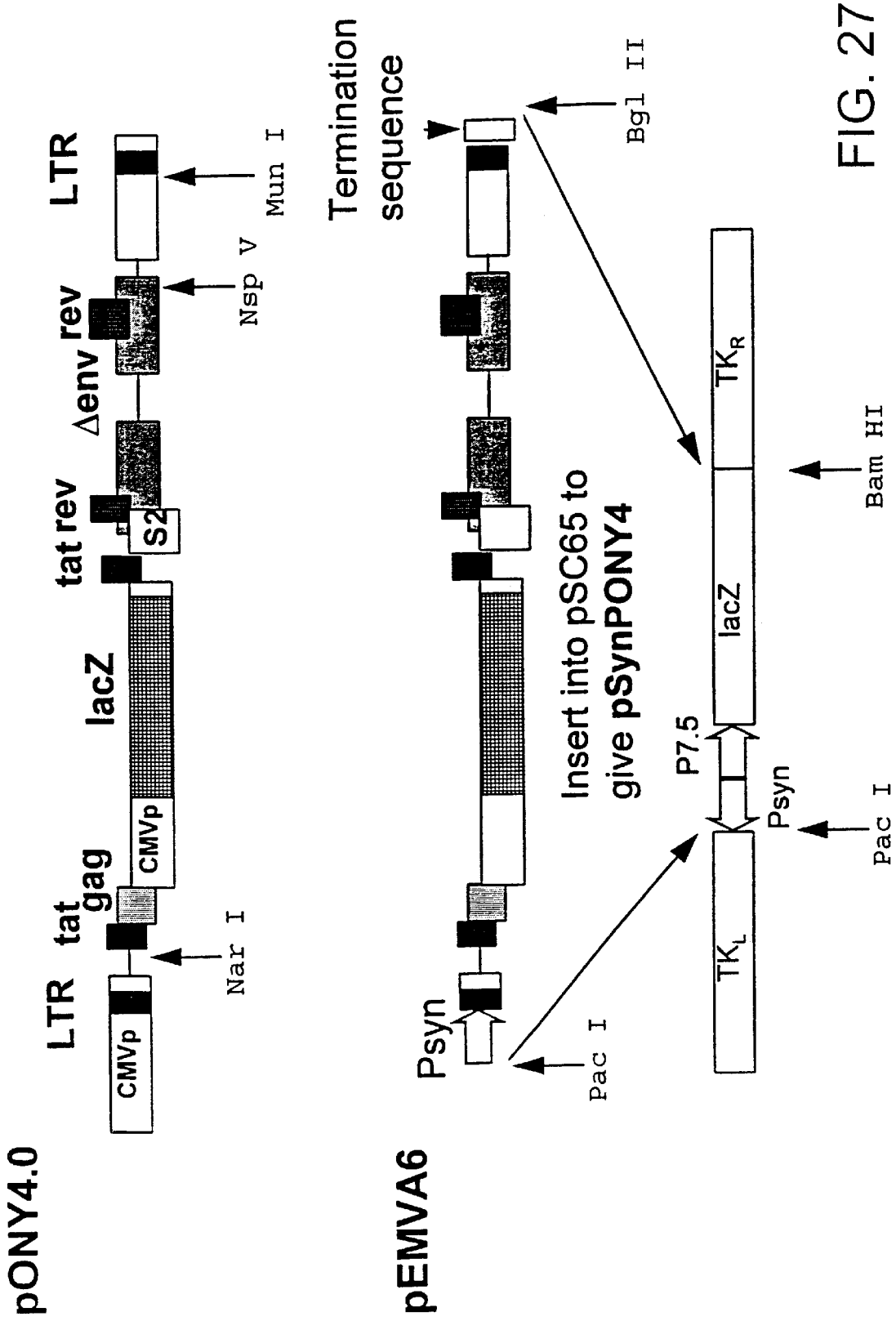
FIG. 27 shows pEMVA6.

The DNA manipulations are as follows: PCR with primers EMVA9/1 produces the 5' LTR with the U3 region replaced by the Psyn promoter and a hammerhead ribozyme (FIG. 25 and 26). This is inserted into the plasmid pEMVA4 (Example 15) using the Pac I/Nar I sites to make pEMVA6 (FIG. 27). This is then cut with Pac I/Bgl II and inserted into pSC65 cut with Pac I/Bam HI to make pSynPONY4 (Bgl II and Bam HI are compatible) (FIG. 27). This removes the two vaccinia promoters and the lacZ coding cassette from pSC65.

Figure 28:
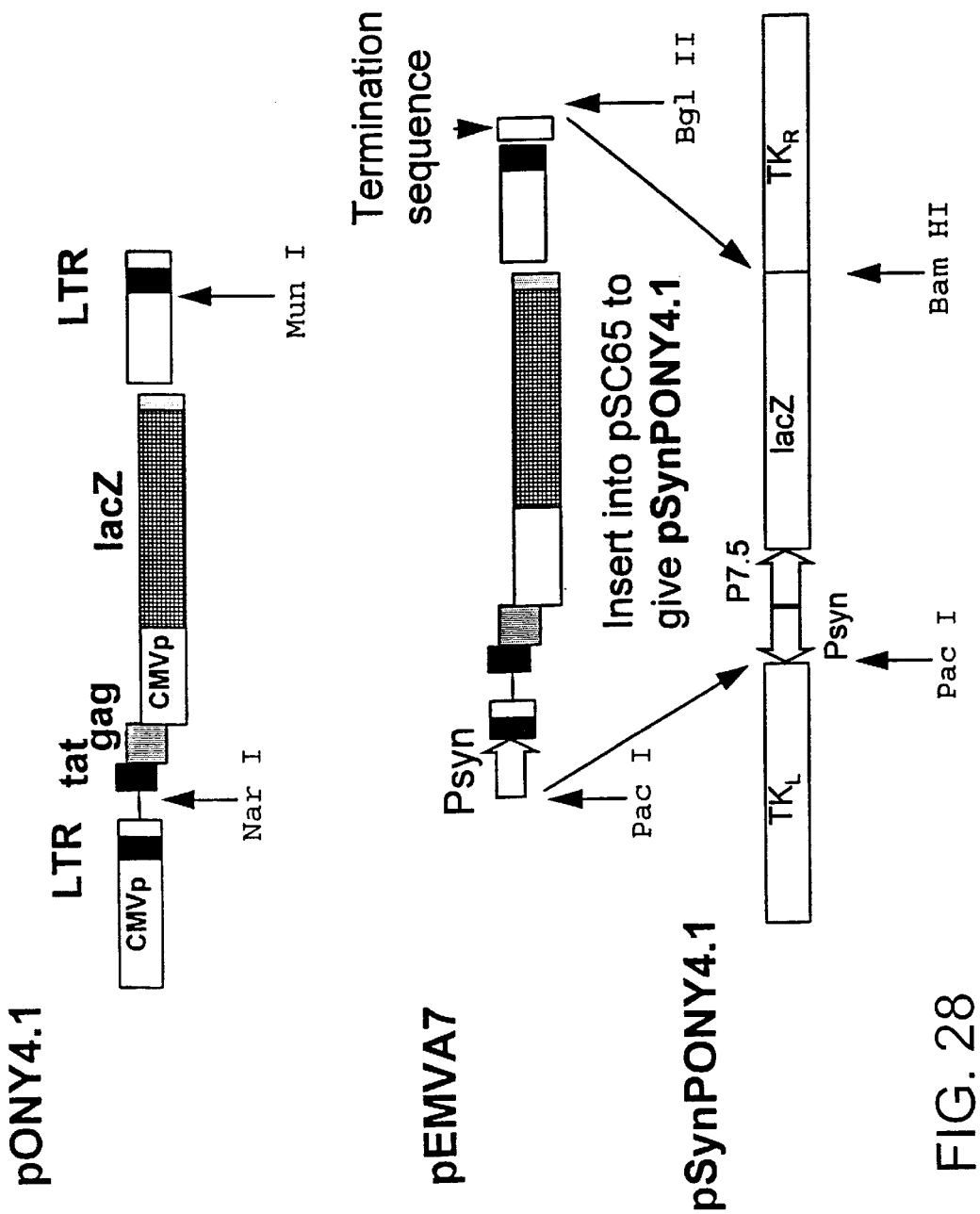
FIG. 28 shows pEMVA7 and pSynPONY4.1.

In order to make the minimal EIAV genome version of this construct that is analogous to pONY4.1, pEMVA6 is cut with Sal I/Nsp V blunt ended and religated to make pEMVA7 (FIG. 28). This is then cut with Pac I/Bgl II and inserted into pSC65 (a vaccinia transfer vector) cut with Pac I/Bam HI to make pSynPONY4.1 (Bgl II and Bam HI are compatible) (FIG. 28). This removes the two vaccinia promoters and the lacZ coding cassette from pSC65.

Both pSynPONY4.0 and pSynPONY4.1 are suitable for inserting the genome expression cassettes into the TK region of the MVA genome (Carroll M W and Moss B Virology 1997 November 24;238(2):198–211) using standard procedures for the construction of recombinant poxviruses (Earl et al 1998a & 1998b)

EXAMPLE 17
T7 Promoter Driving Lentiviral Vector Genome

The T7 promoter can be used to generate a retroviral genome which can make the correct 5' end. Below is described the generation of a transfer plasmid that expresses the EIAV genome from the T7 promoter (T7). Downstream of this promoter is inserted a T7 termination sequence. This is inserted into the transfer plasmid pSC65, which can homologously recombine into the TK region of the MVA genome. The T7 promoter requires the T7 polymerase. MVA viruses are available which express T7 polymerase from Vaccinia promoters (Wyatt et al 1995).

The T7 promoter has the sequence (−)TAATACGACTCACTATAGG (SEQ ID NO: 63)(+2) with transcription beginning after A with preferably a run of Gs. The T7 termination sequence is CTAGCATAACCCCT-TGGGGCCTCTAAACGGGTCTTGAGGGGTTTTTG (SEQ ID NO: 64). The T7 promoter and terminator sequences are as those described in the plasmid pCITE-4a (+) (Novagen).

Figure 29:
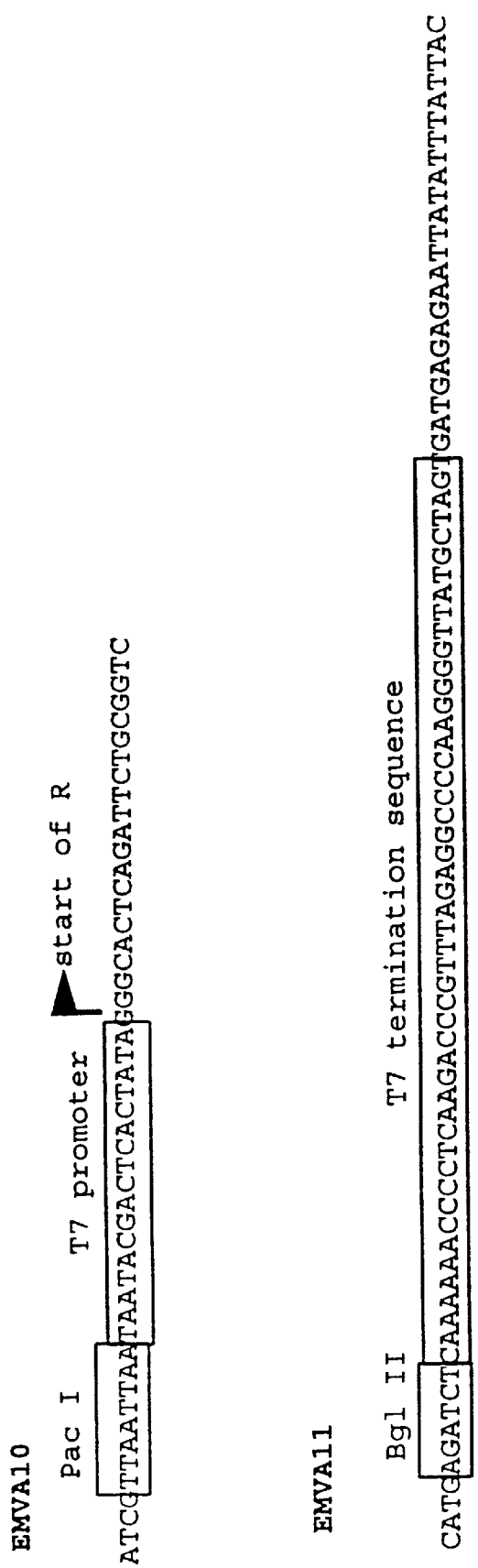
FIG. 29 shows EMVA 10/11 (SEQ ID NOs: 25 and 26).
Figure 30:
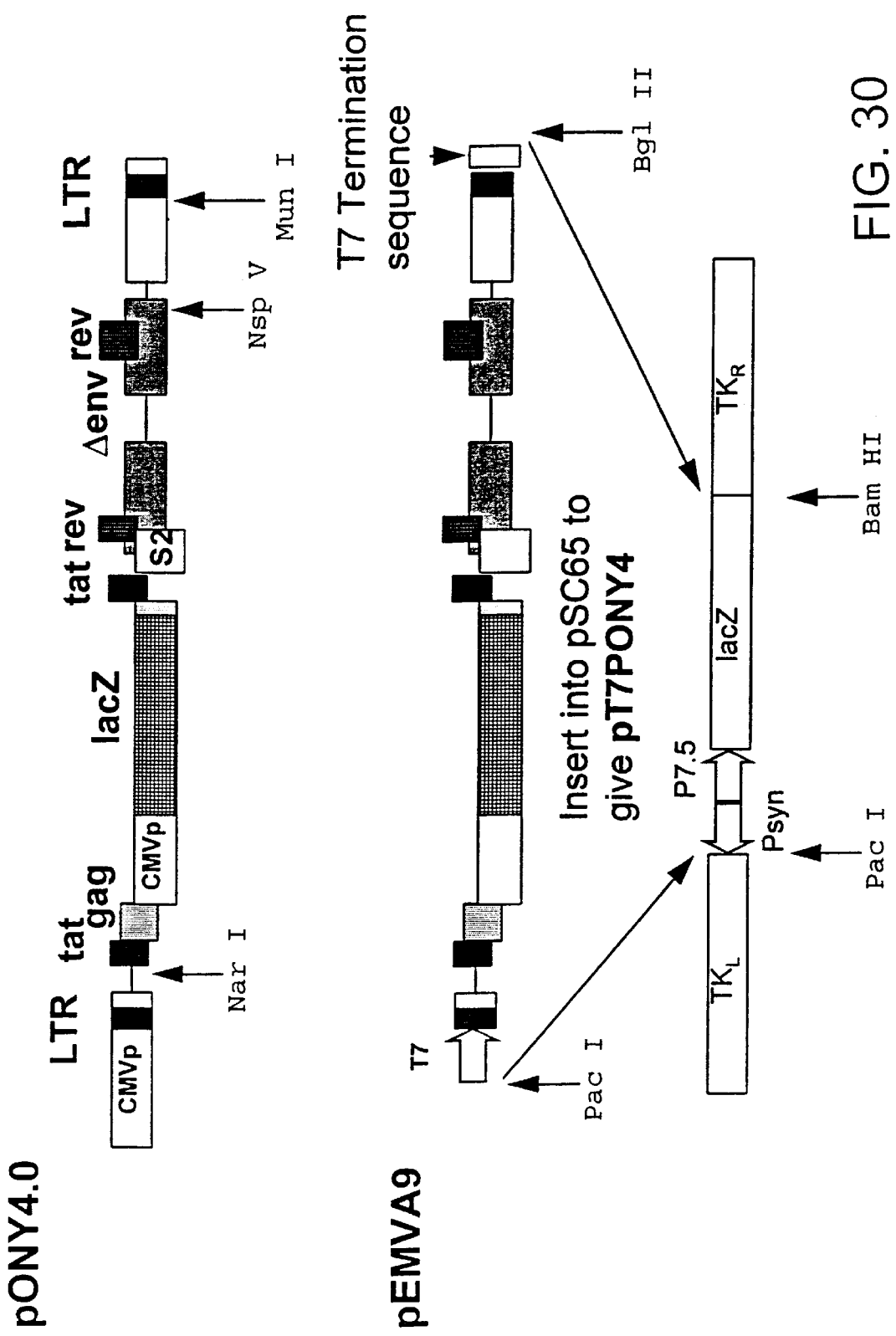
FIG. 30 shows pEMVA9.

The DNA manipulations are as follows. PCR with primers EMVA10/11 (FIG. 29) produces the 5' LTR with the U3 region replaced by the T7 promoter. This is inserted into the plasmid pEMVA4 using the Pac I/Nar I sites to make pEMVA8 (FIG. 30). PCR with primers EMVA11/7 produces part of the 3' LTR with a T7 termination sequence. This is inserted into pEMVA8 using the Mun I/Bgl II sites to make pEMVA9. This is then cut with Pac I/Bgl II and inserted into pSC65 (a vaccinia transfer vector) cut with Pac I/Bam HI to make pT7PONY4 (Bgl II and Bam HI are compatible) (FIG. 30). This removes the two vaccinia promoters and the lacZ coding cassette from pSC65.

Figure 31:
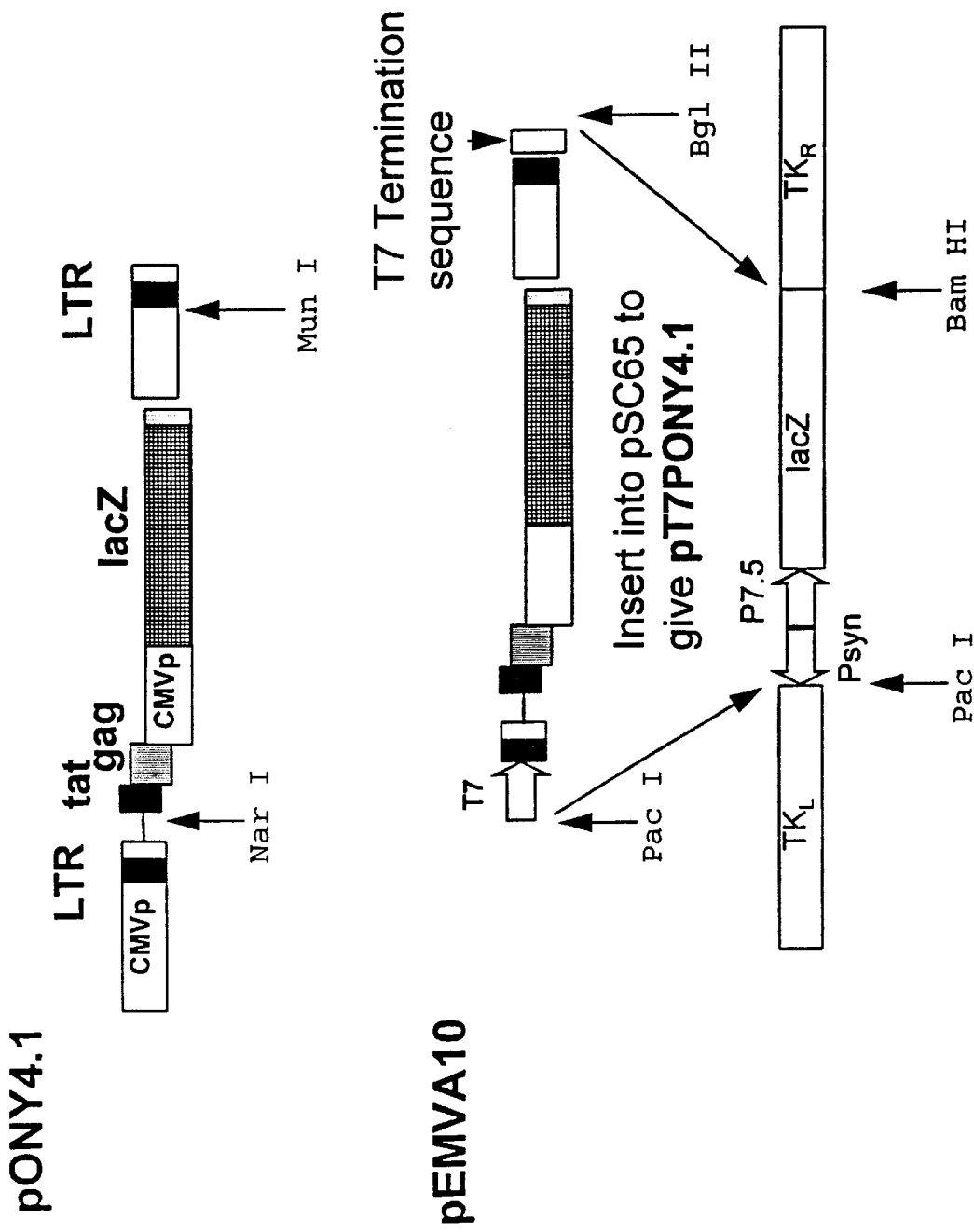
FIG. 31 shows pEMVA10.

To make the minimal EIAV genome version of this construct (pONY4.1) pEMVA9 is cut with Sal I/Nsp V blunt ended and religated to make pEMVA10 (FIG. 31). This is then cut with Pac I/Bgl II and inserted into pSC65 (a vaccinia transfer vector) cut with Pac I/Bam HI to make pT7PONY4.1 (Bgl II and Bam HI are compatible) (FIG. 31). This removes the two vaccinia promoters and the lacZ coding cassette from pSC65.

Both pT7PONY4.0 and pT7PONY4.1 are suitable for inserting the genome expression cassettes into the TK region of the MVA genome (Carroll M W and Moss B Virology 1997) using standard procedures for the construction of recombinant poxviruses (Earl et al 1998a & 1998b).

EXAMPLE 18
Construction of an EIAV gag/pol Cassette For Expression in Vaccinia.

Normally EIAV gag/pol requires Rev/RRE for expression as Rev enables the unspliced transcript to be exported out of the nucleus. As Pox viruses are cytoplasmic, EIAV viral RNA export should not be a problem. But if Rev has other functions such as RNA stability or acts as a translation enhancer it can be expressed in a similar way to EIAV gag/pol (Martarano 1994). Alternatively the EIAV gag/pol sequence can be codon optimised to overcome the Rev/RRE requirement for export and enhance RNA stability. Below is described the creation of a vector that expresses EIAV gag/pol from a synthetic early/late promoter (Psyn). This is inserted into the transfer plasmid pLW-22 (Wyatt and Moss Appendix 1, Earl et al 1998a & b), which can homologously recombine into the Del II region of the MVA genome. Recombinant viruses can be selected by their expression of lac Z.

Figure 32:
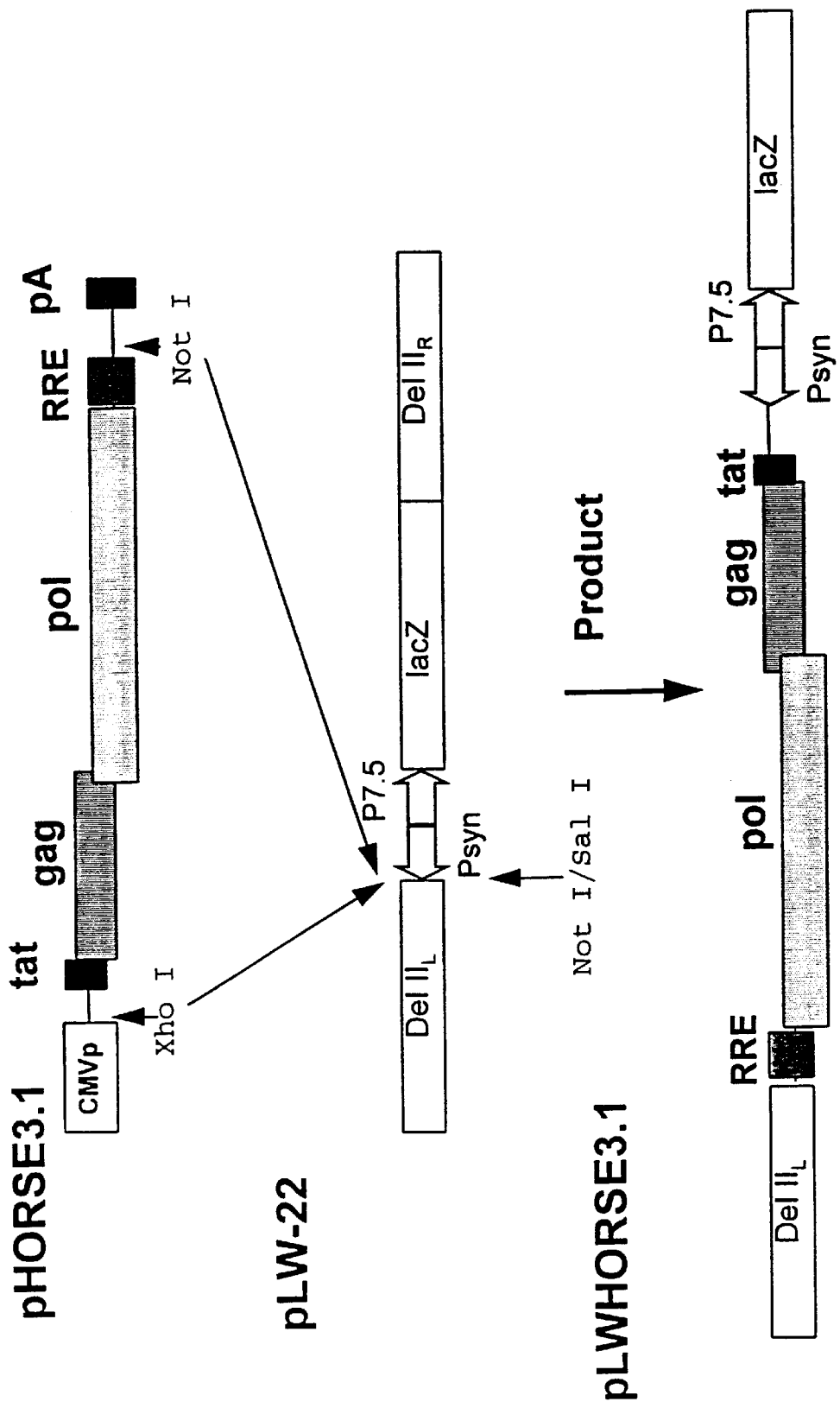
FIG. 32 shows pLWHORSE3.1.

EIAV gag/pol including the leader the gag/pol open reading frame and the RRE can be obtained from cutting pHORSE3.1 (Example 9) with Xho I/Not I to give a 5.5 kb band (FIG. 32). This is then inserted into the vaccinia transfer vector pLW-22 cut with Sal I/Not I (Sal I and Xho I are compatible) to make pLWHORSE3.1 (FIG. 32).

EXAMPLE 19
Construction of an EIAV rev Cassette for Expression in Vaccinia

In the event that Rev is required for EIAV viral vector production from a poxvirus it can be expressed from a synthetic early/late promoter. This construct is inserted into the transfer plasmid pMC03, which can homologously recombine into the Del III region of the MVA genome. Recombinant viruses can be selected by their expression of GUS (Carroll et al. 1995).

Figure 33:
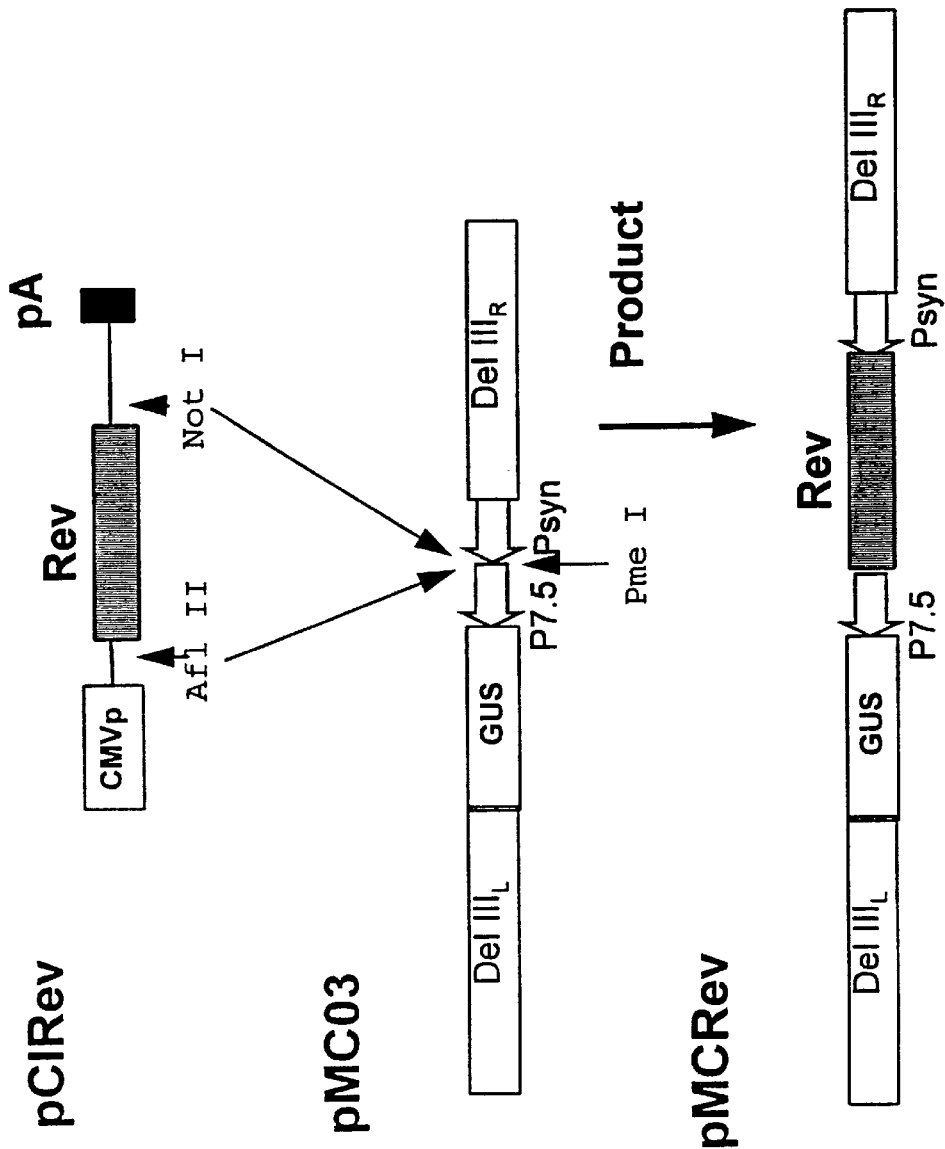
FIG. 33 shows pMCRev.

The DNA manipulations are as follows. Plasmid pCIRev is described in Example 9. It is an EIAV Rev expression plasmid. This is cut with Afl II/Not I (0.6 kb), blunt ended by T4 DNA polymerase and inserted into pMC03 (Carroll et al. 1995) cut with Pme I to make pMCRev (FIG. 33).

EXAMPLE 20
Construction of Heterologous Envelope Cassettes for Expression in Vaccinia EIAV can be pseudotyped with a number of envelopes such as VSV-G and amphotropic MLV envelope. Below is described the creation of a MVA transfer vector that expresses the amphotropic envelope or VSV-G envelope from the P7.5 early/late promoter. The transfer vector is pYT6 which can homologously recombine into the HA region of MVA. Recombinant viruses can be selected by direct live immunostaining for expression of the env.

Figure 34:
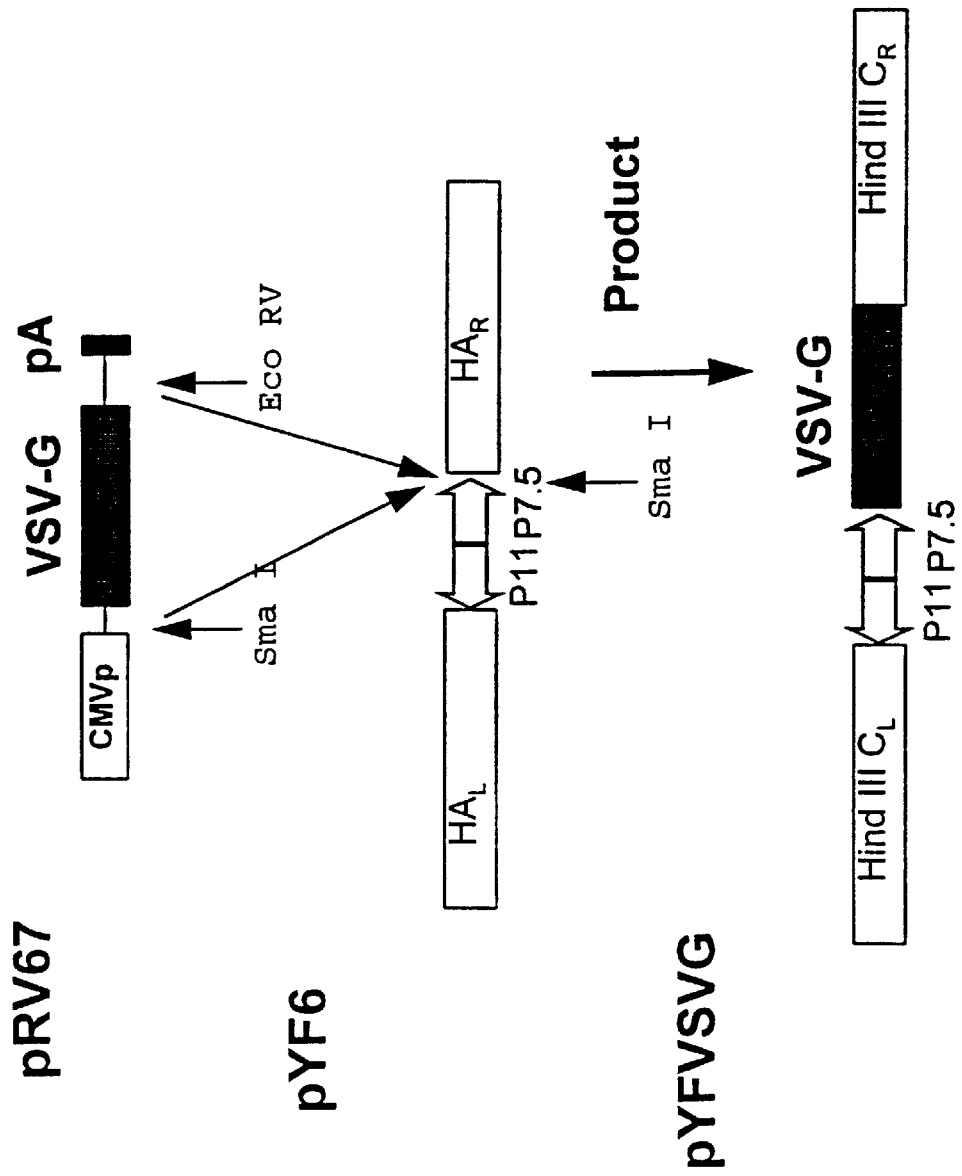
FIG. 34 shows pYFVSVG.
Figure 35:
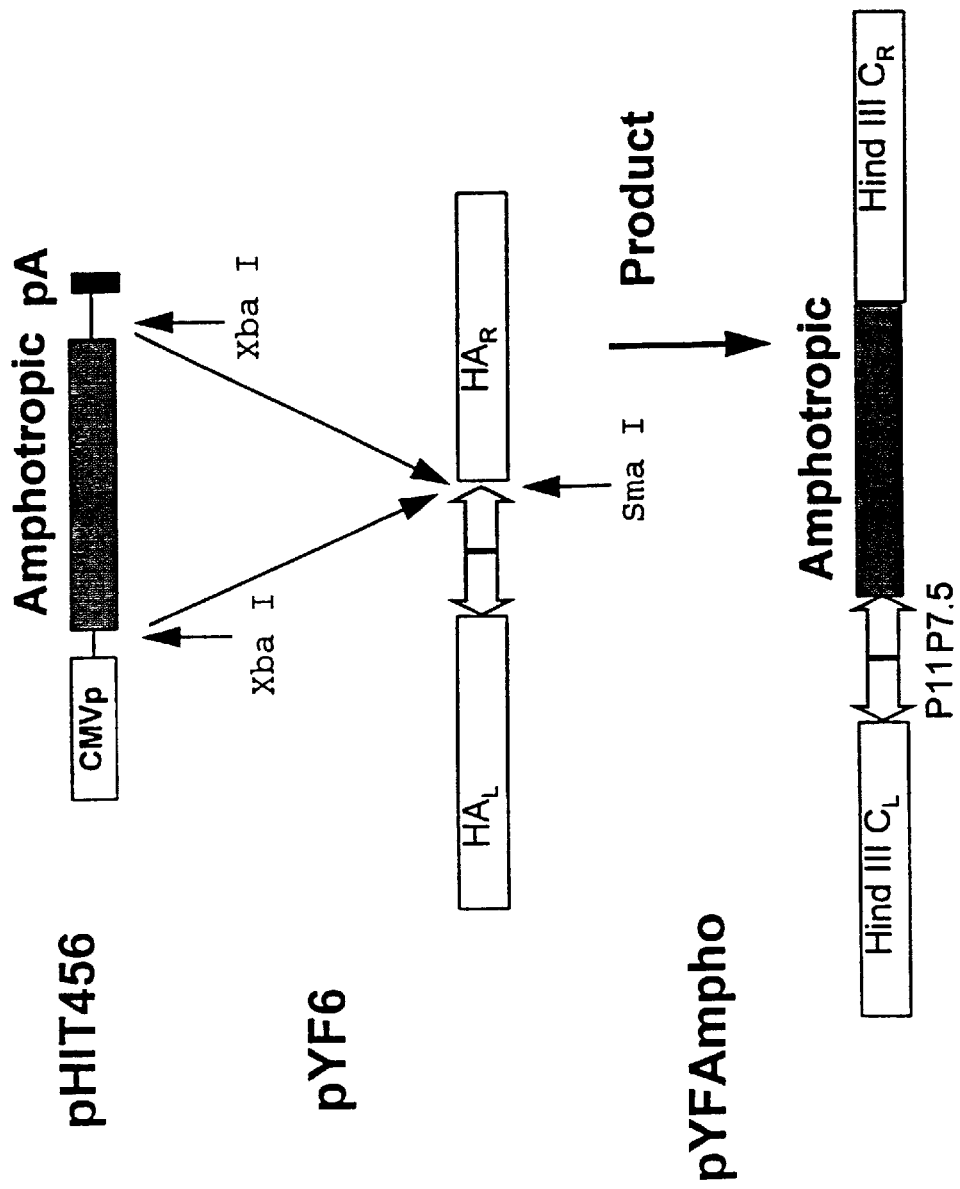
FIG. 35 shows pYFAmpho.

In order to produce a transfer vector containing a VSV-G cassette, the VSV-G expression plasmid pRV67 (Kim et al. 1998) is cut with Sma I/Eco RV(1.7 kb) and the resulting fragment inserted into pYF6 cut with Sma I to make pYFVSVG (FIG. 34). Similarly, to produce an analogous amphotropic envelope construct pHIT456 (Soneoka 1995) is cut with Xba I and the 2.2 kb band blunt ended by T4 DNA polymerase and inserted into pYF6 cut with Sma I making pYFAmpho (FIG. 35).

Both pYFAmpho and pYFVSVG are suitable for inserting the genome expression cassettes into into the HA region of the MVA genome using standard procedures for the construction of recombinant poxviruses (Earl et al 1998a & b, Flexner et al 1987)

EXAMPLE 21
Construction and Amplification of MVA-Lenti Recombinants

Figure 36:
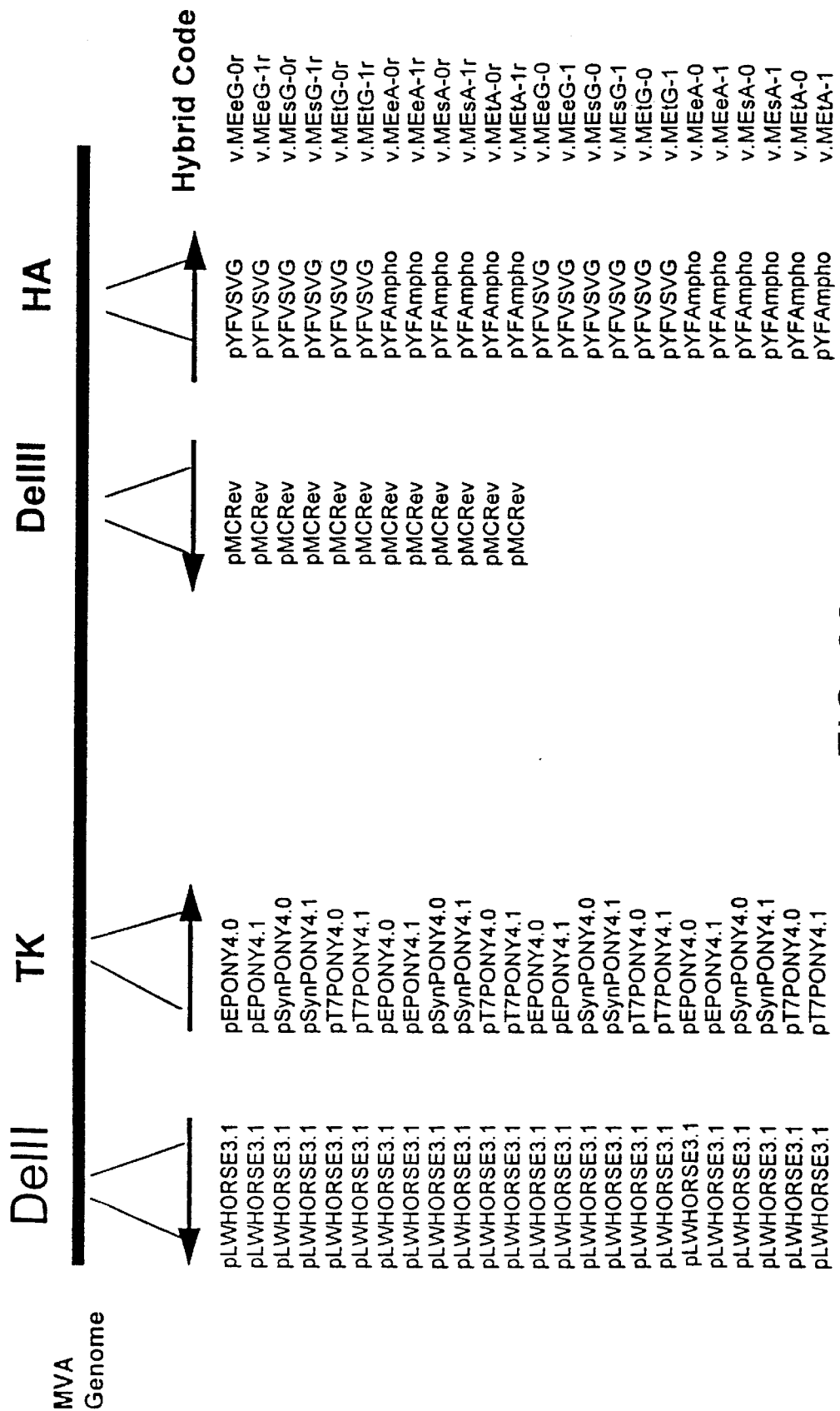
FIG. 36 shows recombinant MVA constructs.

The recombinant vaccinia viruses containing multiple inserts encoding the components of the EIAV vectors (FIG. 25) are constructed by sequential recombination with the relevant transfer plasmids. The construction of v.MEeG-0r (FIG. 36) is used as an example:

1. A plasmid carrying gag-pol (pLWHORSE3.1) is transfected into BHK-21 or CEF cells, that have been previously infected with MVA (as described in Carroll and Moss 1997, Earl et al 1998a & b).
2. After two days of infection recombinant MVA virus is assayed on BHK-21/CEF and cells are over-layed with agar medium containing the substrate for the colour marker β-galactosidase (Chakrabarti et al 1985) which is expressed from within pLW22.
3. Blue plaques are picked and plaque purified until a homogeneous recombinant virus population is obtained.
4. Recombinant virus is then used to recombine with transfer plasmids containing the other recombinant genes: pMCRev in which selection is based on GUS expression (Carroll & Moss 1995), the genome (pEPONY4.0) in which selection is based on a TK negative phenotype using BudR (Carroll & Moss 1997, Earl et al 1998a & b) and VSVG (pYFVSVG) in which recombinants are identified by direct immunostaining of VSVG (Earl et al 1998a & b).

Recombinant viruses may be amplified in BHK-21 or CEF cells as described below

Propagation of Vaccinia Virus

The highly attenuated strain MVA is derived from the replication competent strain Ankara and has endured over 570 passages in primary chick embryo fibroblast cells. MVA replication was initially thought to be restricted to CEF cells as only minimal replication in mammalian cells was reported. However, further analysis has shown that Baby Hamster Kidney cells (BHK-21) are able to support high titre production of MVA. MVA may thus be grown on BHK-21 or primary CEF cells (Carroll & Moss (1997) Virology 238:198–211).

To prepare CEF cells, 10 day old chick embryos are gutted and limbs and head are removed before being minced and trypsinised in a solution of 0.25% trypsin and incubation at 37° C. The cell suspension is filtered through a course filter mesh and cells are washed and concentrated by centrifugation at 2000 rpm in a Sorvall RC-3B at 1500 rpm for 5 mins. Cells are suspended in MEM containing 10% FCS, aliquotted into 175 cm flasks and incubated at 37° C. in a $CO_2$ incubator. When monolayers are 95% confluent they are trypsinised and used to seed additional flasks or six well plates. Alternatively, primary cultures are transferred to a 31° C. incubator for later use (Sutter and Moss (1992) Proc Natl Acad Sci U S A 89:10847–10851).

Preparation of Crude, Semi-purified and Purified Virus Stocks

Crude virus stocks are prepared for initial recombinant virus analysis or as viral stocks used for subsequent high titre virus preparations. Vaccinia virus preparations can be semi-purified by centrifuging out cell membranes and nuclei or by additional steps involving sucrose centrifugation to prevent contamination by preexpressed recombinant protein products and cellular organelles. Methods used are a modification of those described by Earl et al., 1998a & b; Earl and Moss, ibid, pp. 16.17.1–16.17.16; Earl and Moss, ibid, pp. 16.18.1–16.18.10; and Bronte et al., (1997) Proc Natl Acad Sci U S A 94(7):3183–3188.

Crude Virus

MVA is grown in either CEF or BHK-21 (obtained from the ATCC) and WR is grown in HeLa or BS-C-1 (ATCC) in 175 $cm^2$ tissue culture flasks. Briefly, confluent monolayers are infected with an moi of approx. 1 pfu with MVA or WR. Virus is suspended in 10 ml MEM containing 2% FCS and added to 175 $cm^2$ flasks containing confluent cell monolayers. After inoculation for 1 hour at 37° C. an additional 20 ml MEM containing 2% FCS is added. After 48–72 hours infected cells are scraped into the medium and pelleted at 1500 g for 5 mins. For crude virus preparations cells are resuspended 2 ml MEM (2%) per 175 $cm^2$ flask. Cells are freeze thawed three times, sonicated and aliquotted into 1 ml freezing tubes. A representative aliquot is freeze thawed and titred to determine virus concentration. Virus stocks are stored below −20° C.

Semi-pure Preparations

Infected cells are harvested as described previously (Earl et al a & b; Earl and Moss; 1991). After centrifugation cells are resuspended in PBS (2 ml/175 $cm^2$ flask) and homogenised by 30–40 strokes in a tight fitting glass dounce homogeniser, on ice. Cell breakage is checked by microscopy. Nuclei, cellular organelles and membranes are removed by a centrifugation at 300 g for 5 mins (4° C.), keep supernatant. The cell pellet is resuspended in 1 ml/175 $cm^2$ flask and centrifugation repeated. The supernatants are pooled, aliquoted and stored.

Purified Preparation

Infected cells are harvested as previously described (Earl et al.a & b; Earl and Moss; 1991) and resuspended in 10 mM Tris.Cl, pH 9.0 (2 ml/flask), keeping samples on ice from this point of the procedure. Homogenise as described previously using 10 mM Tris. The lysate is sonicated (on ice) using an XL 2015 sonicating cup (Misonics, USA) at maximum output (500 W) for 1 min. The sample is placed on ice for 1 min and the sonication repeated up to 3 times, A maximum of 5 ml is sonicated at a time, and ice is replenished during sonication. The lysate is gently layered onto a cushion of 17 ml of 36% sucrose (in 10 mM Tris.Cl, pH 9.0) in a SW-27 centrifuge tube. Lyates are centrifuged for 80 mins in an SW-27 rotor at 13 500 rpm (32,900×g), 4° C. The supernatant is discarded and the viral pellet resuspended in sterile PBS and sonicated in a cup sonicator for 1 min (on ice). Concentrated virus is aliquoted and stored at below −20° C.

EXAMPLE 22
Production of EIAV Vector Particles From MVA-EIAV Hybrids

As described above large scale preparations of recombinant MVA-EIAV are made. These preparations are used to infect mammalian cells that are non-permissive for MVA, such that the resulting supernatant will only contain EIAV and not infectious MVA (Meyer et al 1991, Carroll and Moss 1997). A suitable cell line is MRC5 (ATCC). Cells are infected at an MOI of 3. Infections are allowed to run for approximately 48 hours before supernatants are harvested and EIAV vector particles either used directly or concentrated/purified by ultracentrifugation or cross-flow methods. To produce large scale preparations, are grown in suspension or on microcarriers or in roller bottles. EIAV vectors carrying gene of interest prepared in these ways are used to transduce target cells in vivo or in vitro.

References

Blomer, U., Naldini, L., Kafri, T., Trono, D., Verma, I. M., and Gage, F. H. (1997). Highly efficient and sustained gene transfer in adult neurons with a lentivirus vector. J Virol 71, 6641–6649.

Blomer, U., Naldini, L., Verma, I. M., Trono, D., and Gage, F. H. (1996). Applications of gene therapy to the CNS. Hum Mol Genet 5 Spec No, 1397–404.

Clever, J., Sassetti, C., and Parslow, T. G. (1995). RNA secondary structure and binding sites for gag gene products in the 5' packaging signal of human immunodeficiency virus type 1. J Virol 69, 2101–9.

Clever, J. L., and Parslow, T. G. (1997). Mutant human immunodeficiency virus type 1 genomes with defects in RNA dimerization or encapsidation. J Virol 71, 3407–14.

Fields, B. N., Knipe, D. M., and Howley, P. M. (1996). Fields Virology, R. M. Chanock, J. L. Melnick, T. P. Monath, B. Roizman and S. E. Straus, eds. (Philadelphia. N.Y.: Lippincott—Raven Publishers).

Fuller S, von Bonsdorff C H, Simons K. Vesicular stomatitis virus infects and matures only through the basolateral surface of the polarized epithelial cell line, MDCK. Cell 1984 August;38(1):65–77

Harrison, G. S., Long, C. J., Maxwell, F., Glode, L. M., and Maxwell, I. H. (1992). Inhibition of HIV production in cells containing an integrated, HIV-regulated diphtheria toxin A chain Gene. AIDs Research and Human Retrovirus 8, 39–45.

Hayashi T, Shioda T, Iwakura Y, Shibuta H. RNA packaging signal of human immunodeficiency virus type 1. Virology 1992 June; 1 88(2):590–599

Kim V. N., Mitrophanous K., Kingsman S. M., Kingsman A. J. 1998. Minimal Requirement for a Lentiviral Vector Based on Human Immunodeficiency Virus Type 1. J. Virol. 1998 72:811–6.

Kim, S. Y., R. Byrn, J. Groopman, and D. Baltimore. 1989. Temporal aspects of DNA and RNA synthesis during human immunodeficiency virus infection: evidence for differential gene expression. J. Virol. 63:3708–3713.

Lewis, P. F., and M. Emerman. 1994. Passage through mitosis is required for oncoretroviruses but not for the human immunodeficiency virus. J Virol. 68:510–6.

Mann R, Mulligan R C, Baltimore D. Construction of a retrovirus packaging mutant and its use to produce helper-free defective retrovirus. Cell 1983 May;33(1):153–159

Martarano, L., Stephens, R., Rice, N., and Derse, D. (1994). Equine infectious anemia virus trans-regulatory protein Rev controls viral mRNA stability, accumulation, and alternative splicing. J Virol 68, 3102–11.

Naldini, L., Blomer, U., Gage, F. H., Trono, D., and Verma, I. M. (1996). Efficient transfer, integration, and sustained long-term expression of the transgene in adult rat brains injected with a lentiviral vector. Proc Natl Acad Sci U S A 93, 11382–11388.

Naldini, L., Blomer, U., Gallay, P., Ory, D., Mulligan, R., Gage, F. H., Verma, I. M., and Trono, D. (1996). In vivo gene delivery and stable transduction of nondividing cells by a lentiviral vector [see comments]. Science 272, 263–7.

Payne, S. L., Rausch, J., Rushlow, K., Montelaro, R. C., Issel, C., Flaherty, M., Perry, S., Sellon, D., and Fuller, F. (1994). Characterization of infectious molecular clones of equine infectious anaemia virus. J Gen Virol 75, 425–9.

Yee, J.-K., M. Atsushi, P. LaPorte, K. Bouic, J. C. Burns, and T. Friedmann (1994) A general method for th generation of high-titer, pantropic retroviral vectors: Highly efficient infection of primary hepatocytes. Proc. Natl. Acad. Sci. USA 91:9564–9568.

Zufferey, R., Nagy, D., Mandel, R. J., Naldini, L., and Trono, D. (1997). Multiply attenuated lentiviral vector achieves efficient gene delivery in vivo. Nat Biotechnol 15, 871–875.

Cannon 1996 J Virol 1996 70:8234–40. Murine leukemia virus-based Tat-inducible long terminal repeat replacement vectors: a new system for anti-human immunodeficiency virus gene therapy. Cannon P M, Kim N, Kingsman S M, Kingsman A J.

Carroll M W, Moss B E. coli beta-glucuronidase (GUS) as a marker for recombinant vaccinia viruses. Biotechniques 1995 19:352–4

Carroll M W, Moss B Host range and cytopathogenicity of the highly attenuated MVA strain of vaccinia virus: propagation and generation of recombinant viruses in a non-human mammalian cell line. Virology 1997 238:198–211

Chakrabarti S, Brechling K, Moss B Vaccinia virus expression vector: coexpression of beta-galactosidase provides visual screening of recombinant virus plaques. Mol Cell Biol 1985 12:3403–9

Chakrabarti S, Sisler J R, Moss B Biotechniques 1997 6:1094–7 Compact, synthetic, vaccinia virus early/late promoter for protein expression.

Davison 1989a J Mol Biol 1989 20;210(4):749–69. Structure of vaccinia virus early promoters. Davison A J, Moss B Davison 1989b J Mol Biol 1989 210(4):771–84 . Structure of vaccinia virus late promoters. Davison A J, Moss B PL. Earl (a), N. Cooper, L S Wyatt, B. Moss & M. W. Carroll 1998 Preparation of Cell Cultures and Vaccinia Virus Stocks. Current Protocols in Molecular Biology Supplement 43 Unit 16.16. John Wiley and Sons Inc.

PL. Earl (b), B. Moss L. S. Wyatt, & M. W. Carroll 1998 Generation of Recombinant Vaccinia Viruses. Current Protocols in Molecular Biology. Supplement 43 Unit 16.17. Current Protocols in Molecular Biology. John Wiley and Sons Inc.

Flexner C, Hugin A, Moss B Nature 1987 330(6145):259–62 Prevention of vaccinia virus infection in immunodeficient mice by vector-directed IL-2 expression.

Holzer G W, Falkner F G Construction of a vaccinia virus deficient in the essential DNA repair enzyme uracil DNA glycosylase by a complementing cell line. J Virol 1997 71:4997–5002

Kim V N, Mitrophanous K, Kingsman S M, Kingsman A J Minimal requirement for a lentivirus vector based on human immunodeficiency virus type 1. J Virol 1998 72:811–6

Mackett M, Smith G L, Moss B Vaccinia virus: a selectable eukaryotic cloning and expression vector. Proc Natl Acad Sci U S A 1982 7923:7415–9

Mahnel H, Mayr A Berl Munch Tierarztl Wochenschr 1994 August; 107(8):253–6 [Experiences with immunization against orthopox viruses of humans and animals using vaccine strain MVA].[Article in German] Zentralbl Bakteriol [B] 1978 December; 167(5–6):375–90

Martarano L, Stephens R, Rice N, Derse D Equine infectious anemia virus trans-regulatory protein Rev controls viral mRNA stability, accumulation, and alternative splicing. J Virol 1994 May;68(5):3102–11

Mayr A, Stickl H, Muller H K, Danner K, Singer H [The smallpox vaccination strain MVA: marker, genetic structure, experience gained with the parenteral vaccination and behavior in organisms with a debilitated defence mechanism]. Zentralbl Bakteriol [B]. 1978, December; 167(5–6):375–90. German.

Meyer H, Sutter G, Mayr A Mapping of deletions in the genome of the highly attenuated vaccinia virus MVA and their influence on virulence. J Gen Virol 1991 72:1031–

Moss B Poxviridae: The viruses and their replication Chapter 83. p2637–2672. In Fields, B. N., Knipe, D. M. & Howley, P. M. Fields Virology. Third Edition edn Vol. 2 eds Chanock, R. M., Melnick, J. L., Monath, T. P., Roizman, B. & Straus, S. E. Lippincott—Raven Publishers, Philadelphia. N.Y., 1996

Moss B, Carroll M W, Wyatt L S, Bennink J R, Hirsch V M, Goldstein S, Elkins W R, Fuerst T R, Lifson J D, Piatak M, Restifo N P, Overwijk W, Chamberlain R, Rosenberg S A, Sutter G Host range restricted, non-replicating vaccinia virus vectors as vaccine candidates. Adv Exp Med Biol 1996;397:7–13

Panicali D, Paoletti E Construction of poxviruses as cloning vectors: insertion of the thymidine kinase gene from herpes simplex virus into the DNA of infectious vaccinia virus.

Proc Natl Acad Sci U S A 1982 79:4927–31

Soneoka Y, Cannon P M, Ramsdale E E, Griffiths J C, Romano G, Kingsman S M, Kingsman A J 1995 Nucleic Acids Res 1995 23628–33. A transient three-plasmid expression system for the production of high titer retroviral vectors.

Sutter G, Moss B Nonreplicating vaccinia vector efficiently expresses recombinant genes. Proc Natl Acad Sci U S A 1992 November 15;89(22):10847–51

Taylor J, Weinberg R, Tartaglia J, Richardson C, Alkhatib G, Briedis D, Appel M, Norton E, Paoletti E Nonreplicating viral vectors as potential vaccines: recombinant canarypox virus expressing measles virus fusion (F) and hemagglutinin (HA) glycoproteins. Virology 1992 March;187 (1):321–8

Paoletti E, Tartaglia J, Taylor J Safe and effective poxvirus vectors—NYVAC and ALVAC. Dev Biol Stand 1994;82:65–9

Wyatt L S, Moss B, Rozenblatt S Replication-deficient vaccinia virus encoding bacteriophage T7 RNA polymerase for transient gene expression in mammalian cells. Virology 1995 June 20;210(1):202–5

Wyatt L S, Carroll M W, Czemy C P, Merchlinsky M, Sisler J R, Moss B Marker rescue of the host range restriction defects of modified vaccinia virus Ankara. Virology 1998 251:334–42

Wyatt L S, Shors S T, Murphy B R, Moss B Development of a replication-deficient recombinant vaccinia virus vaccine effective against parainfluenza virus 3 infection in an animal model. Vaccine 1996 October;14(15):1451–8

What is claimed is:

1. An equine infectious anemia virus (EIAV) vector comprising a gag gene nucleotide coding sequence that is modified so as to contain a deletion located at least 354 nucleotides downstream from the ATG initiation codon of the gag gene in EIAV.

2. The EIAV vector according to claim 1 wherein the deletion is from nucleotide 354 to at least the C-terminus of the gag-pol coding region in EIAV.

3. The EIAV vector according to claim 1 wherein the deletion additionally removes nucleotide 300 of the gag gene nucleotide coding sequence in EIAV.

4. The EIAV vector according to any one of claims 1, 2, or 3 wherein the deletion further includes at least one nucleotide upstream from the nucleotide at position 354 downstream from the ATG initiation codon of the gag gene in EIAV, and wherein the vector retains the first 150 nucleotides of the gag gene nucleotide coding sequence in EIAV.

5. The EIAV vector according to any one of claims 1, 2, or 3 wherein the deletion further includes at least one nucleotide upstream from the nucleotide at position 354 downstream from the ATG initiation codon of the gag gene in EIAV, and wherein the vector retains the first 109 nucleotides of the gag gene coding nucleotide sequence in EIAV.

6. The EIAV vector according to any one of claims 1, 2, or 3 wherein the deletion further includes at least one nucleotide upstream from the nucleotide at position 354 downstream from the ATG initiation codon of the gag gene in EIAV, and wherein the vector retains the first 2 nucleotides of the gag gene nucleotide coding sequence in EIAV.

7. The EIAV vector according to any one of claims 1, 2 or 3 wherein one or more accessory genes are absent from the vector.

8. The EIAV vector according to claim 7 wherein the accessory genes are selected from the group consisting of dUTPase, S2, rev and tat, and combinations thereof.

9. The EIAV vector according to claim 4 wherein the EIAV gag gene coding sequence is only the first 150 nucleotides of the gag gene coding sequence in EIAV.

10. The EIAV vector according to claim 5 wherein the EIAV gag gene coding sequence is only the first 109 nucleotides of the gag gene coding sequence in EIAV.

11. The EIAV vector according to claim 6 wherein the EIAV gag gene coding sequence is only the first 2 nucleotides of the gag gene coding sequence in EIAV.

12. A method for expressing a gene product comprising contacting a cell with the EIAV vector of any one of claims 1, 2 or 3, wherein the vector includes a nucleic acid sequence encoding said gene product.

13. An isolated cell comprising the EIAV vector according to any one of claims 1, 2 or 3.

14. A delivery system comprising the EIAV vector according to any one of claims 1, 2 or 3, and a pharmaceutically acceptable carrier.

15. The EIAV vector according to any one of claims 1, 2 or 3 further comprising a heterologous nucleotide sequence of interest.

16. An isolated equine infectious anemia virus (EIAV)-based vector particle comprising functionally active gag-pol proteins, and further comprising a nucleic acid sequence of EIAV gag nucleotide residues having a deletion located at least 350 nucleotides downstream from the ATG initiation codon of the EIAV gag coding sequence.

17. The EIAV vector according to claim 2 wherein the deletion additionally removes nucleotide 300 of the gag gene nucleotide coding sequence in EIAV.

18. The EIAV vector according to claim 4 wherein one or more accessory genes are absent from the vector.

19. The EIAV vector according to claim 18 wherein the accessory genes are selected from the group consisting of dUTPase, S2, rev and tat, and combinations thereof.

20. The EIAV vector according to claim 5 wherein one or more accessory genes are absent from the vector.

21. The EIAV vector according to claim 20 wherein the accessory genes are selected from the group consisting of dUTPase, S2, rev and tat, and combinations thereof.

22. The EIAV vector according to claim 6 wherein one or more accessory genes are absent from the vector.

23. The EIAV vector according to claim 22 wherein the accessory genes are selected from the group consisting of dUTPase, S2, rev and tat, and combinations thereof.

24. An equine infectious anemia virus (EIAV)-based retroviral vector particle comprising a gag gene nucleotide coding sequence that is modified so as to contain a deletion located at least 354 nucleotides downstream from the ATG initiation codon of the gag gene in EIAV.

25. The EIAV-based retroviral vector particle according to claim 24 wherein the deletion is from nucleotide 354 to at least the C-terminus of the gag-pol coding region in EIAV.

26. The EIAV-based retroviral vector particle according to claim 24 wherein the deletion additionally removes nucleotide 300 of the gag gene nucleotide coding sequence in EIAV.

27. The EIAV-based retroviral vector particle according to any one of claims 24, 25, or 26 wherein the deletion further includes at least one nucleotide upstream from the nucleotide at position 354 downstream from the ATG initiation codon of the gag gene in EIAV, and wherein the vector particle retains the first 150 nucleotides of the gag gene nucleotide coding sequence in EIAV.

28. A production system for producing the EIAV-based retroviral vector particle of any one of claims 24, 25 or 26 comprising a packaging cell comprising an EIAV-based RNA genome, a gag-pol gene, and an envelope gene, wherein said genome comprises a gag gene nucleotide coding sequence that is modified so as to contain a deletion located at least 354 nucleotides downstream from the ATG initiation codon of the gag gene nucleotide coding sequence in EIAV.

29. An EIAV-based retroviral vector particle produced by the production system of claim 28.

30. The EIAV-based retroviral vector particle according to any one of claims 24, 25, or 26 wherein the deletion further includes at least one nucleotide upstream from the nucleotide at position 354 downstream from the ATG initiation codon of the gag gene in EIAV, and wherein the vector particle retains the first 109 nucleotides of the gag gene nucleotide coding sequence in EIAV.

31. The EIAV-based retroviral vector particle according to any one of claims 24, 25, or 26 wherein the deletion further includes at least one nucleotide upstream from the nucleotide at position 354 downstream from the ATG initiation codon of the gag gene in EIAV, and wherein the vector particle retains the first 2 nucleotides of the gag gene nucleotide coding sequence in EIAV.

32. The EIAV-based retroviral vector particle according to any one of claims 24, 25 or 26 wherein one or more accessory genes or gene products therefrom are absent from the vector particle.

33. The EIAV-based retroviral vector particle according to claim 32 wherein the accessory genes are selected from the group consisting of dUTPase, S2, rev and tat, and combinations thereof.

34. The EIAV-based retroviral vector particle according to claim 27 wherein the EIAV gag gene coding sequence is only the first 150 nucleotides of the gag gene coding sequence in EIAV.

35. The EIAV-based retroviral vector particle according to claim 30 wherein the EIAV gag gene coding sequence is only the first 109 nucleotides of the gag gene coding sequence in EIAV.

36. The EIAV-based retroviral vector particle according to claim 31 wherein the EIAV gag gene coding sequence is only the first 2 nucleotides of the gag gene coding sequence in EIAV.

37. The EIAV-based retroviral vector particle according to claim 25 wherein the deletion additionally removes nucleotide 300 of the gag gene nucleotide coding sequence in EIAV.

38. The EIAV-based retroviral vector particle according to claim 27 wherein one or more accessory genes or gene products therefrom are absent from the vector particle.

39. The EIAV-based retroviral vector particle according to claim 38 wherein the accessory genes are selected from the group consisting of dUTPase, S2, rev and tat, and combinations thereof.

40. The EIAV-based retroviral vector particle according to claim 30 wherein one or more accessory genes or gene products therefrom are absent from the vector particle.

41. The EIAV-based retroviral vector particle according to claim 40 wherein the accessory genes are selected from the group consisting of dUTPase, S2, rev and tat, and combinations thereof.

42. The EIAV-based retroviral vector particle according to claim 31 wherein one or more accessory genes or gene products therefrom are absent from the vector particle.

43. The EIAV-based retroviral vector particle according to claim 42 wherein the accessory genes are selected from the group consisting of dUTPase, S2, rev and tat, and combinations thereof.

44. A method for expressing a gene product comprising contacting a cell with the EIAV-based retroviral vector particle of any one of claims 24, 25 or 26, wherein the vector particle includes a nucleic acid sequence encoding said gene product.

45. An isolated cell comprising the EIAV-based retroviral vector particle according to any one of claims 24, 25 or 26.

46. A delivery system comprising the EIAV-based retroviral vector particle according to any one of claims 24, 25 or 26, and a pharmaceutically acceptable carrier.

47. The EIAV-based retroviral vector particle according to any one of claims 24, 25 or 26 further comprising a heterologous nucleotide sequence of interest.

48. The EIAV-based retroviral particle according to claim 32 further comprising a heterologous nucleotide sequence of interest.

49. The EIAV-based retroviral particle according to claim 33 further comprising a heterologous nucleotide sequence of interest.

50. The EIAV vector according to claim 7 further comprising a heterologous nucleotide sequence of interest.

51. The EIAV vector according to claim 8 further comprising a heterologous nucleotide sequence of interest.

52. The production system of claim 28 further comprising a heterologous nucleotide sequence of interest.

53. The production system of claim 28 wherein one or more accessory genes or gene products thereof are absent.

54. The method of claim 53 wherein the accessory genes are selected from the group consisting of dUTPase, S2, rev and tat, and combinations thereof.

55. A method for producing the EIAV-based retroviral vector particle of any one of claims 24, 25 or 26 comprising co-expressing in a packaging cell nucleic acid sequence(s) encoding an EIAV-based RNA genome, a gag-pol gene, and an envelope gene, wherein said genome comprises a gag gene nucleotide sequence that is modified so as to contain a deletion located at least 354 nucleotides downstream from the ATG initiation codon of the gag gene in EIAV.

56. The method of claim 55 wherein the genome includes a heterologous nucleotide sequence of interest.

57. The method of claim 56 wherein one or more accessory genes or gene products thereof are absent.

58. The method of claim 57 wherein the accessory genes are selected from the group consisting of dUTPase, S2, rev and tat, and combinations thereof.

59. A production system for producing the EIAV-based retroviral vector particle of any one of claim 16 comprising a packaging cell comprising an EIAV-based RNA genome, a gag-pol gene, and an envelope gene, wherein said genome comprises a nucleic acid sequence of EIAV gag nucleotide residues having a deletion located at least 350 nucleotides downstream from the ATG initiation codon of the EIAV gag coding sequence.

60. An EIAV-based retroviral vector particle produced by the production system of claim 59.

61. A method for producing the EIAV-based retroviral vector particle of claim 16 comprising co-expressing in a packaging cell nucleic acid sequence(s) encoding an EIAV-based RNA genome, a gag-pol gene, and an envelope gene, wherein said genome comprises a nucleic acid sequence of EIAV gag nucleotide nucleotide residues having a deletion located at least 350 nucleotides downstream from the ATG initiation codon of the EIAV gag gene coding sequence.

62. The method of claim 61 wherein the genome includes a heterologous nucleotide sequence of interest.

63. The method of claim 62 wherein one or more accessory genes or gene products thereof are absent.

64. The method of claim 63 wherein the accessory genes are selected from the group consisting of dUTPase, S2, rev and tat, and combinations thereof.

* * * * *

UNITED STATES PATENT AND TRADEMARK OFFICE
CERTIFICATE OF CORRECTION

PATENT NO. : 6,312,683 B1
DATED : November 6, 2001
INVENTOR(S) : Kingsman et al.

It is certified that error appears in the above-identified patent and that said Letters Patent is hereby corrected as shown below:

<u>Title page,</u>
Item [56], References Cited, OTHER PUBLICATIONS, change "J. Mol. Biol. 201, 1980, p. 771-784, Davidson et al. "Structure of Vaccinia Virus Late Promoters" to
-- J. Mol. Biol. 201, 1989, p. 771-784, Davidson et al. "Structure of Vaccinia Virus Late Promoters" --

Signed and Sealed this

Sixteenth Day of September, 2003

JAMES E. ROGAN
*Director of the United States Patent and Trademark Office*

SEQUENCE LISTING

```
<160> NUMBER OF SEQ ID NOS:    64

<210> SEQ ID NO 1
<211> LENGTH: 381
<212> TYPE: RNA
<213> ORGANISM: Equine infectious anemia virus

<400> SEQUENCE: 1
augauaccgg gcacucagau ucugcggucu gagucccuuc ucugcugggc ugaaaaggcc      60
uuuguauaaa uauaauucuc uacucagucc cugucucuag uuugucuguu cgagauccua     120
caguuggcgc ccgaacaggg accugagggg gcgcagaccc uaccuguuga accuggcuga     180
ucguaggauc cccgggacag cagaggagaa cuuacagaag ucuucuggag uguuccugg     240 ggagaacaca ggaggacagg uaagauggga gacccuuuga cauggagcaa ggcgcucaag     300
aaguuaagaa ggugacggua caaggucuc aguuaacucu gguaacugua auugggcgcu     360
aagucuaggu agacuuauuu c                                               381

<210> SEQ ID NO 2
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: sequence showing part of split polyA signal

<400> SEQUENCE: 2
```

```
tcgctgcagc ggaataaagg gcaggtaagt atcaaggtta c                 41
```

<210> SEQ ID NO 3
<211> LENGTH: 60
<212> TYPE: DNA
<213> ORGANISM: Artificial Sequence, primer
<220> FEATURE:
<221> NAME/KEY: misc_feature
<222> LOCATION: (1)..(60)
<223> OTHER INFORMATION: sequence showing the part of split polyA
      signal

<400> SEQUENCE: 3

```
tcgctgcagc ggacacacaa aaaccaaca cacagaactg ggaagtggac acctgtggag   60
```

<210> SEQ ID NO 4
<211> LENGTH: 63
<212> TYPE: DNA
<213> ORGANISM: Artificial Sequence
<220> FEATURE:
<221> NAME/KEY: misc_feature
<222> LOCATION: (1)..(63)
<223> OTHER INFORMATION: sequence showing both the parts of polyA
      signal

<400> SEQUENCE: 4

```
aataaagggc aggtaagctc cacaggtgtc cactccagtt ctgtgtgttg gttttttgtg   60
tgt                                                                63
```

<210> SEQ ID NO 5
<211> LENGTH: 50
<212> TYPE: DNA
<213> ORGANISM: Artificial Sequence
<220> FEATURE:
<221> NAME/KEY: polyA_signal
<222> LOCATION: (1)..(50)
<223> OTHER INFORMATION: sequence of the polyA signal

<400> SEQUENCE: 5

```
aataaagggc aggtgtccac tccagttctg tgtgttggtt tttgtgtgt          50
```

<210> SEQ ID NO 6
<211> LENGTH: 33
<212> TYPE: DNA
<213> ORGANISM: Artificial Sequence, primer
<220> FEATURE:
<221> NAME/KEY: misc_feature
<222> LOCATION: (1)..(33)
<223> OTHER INFORMATION: primer

<400> SEQUENCE: 6

```
tcgatagatc tgagtccgtt acataactta cgg                          33
```

<210> SEQ ID NO 7
<211> LENGTH: 57
<212> TYPE: DNA
<213> ORGANISM: Artificial Sequence,primer
<220> FEATURE:
<221> NAME/KEY: misc_feature
<222> LOCATION: (1)..(57)
<223> OTHER INFORMATION: primer

<400> SEQUENCE: 7

```
gatctcgaac agacaaacta gagacaggga ctgcaaacag caagaggctt tattggg    57
```

<210> SEQ ID NO 8
<211> LENGTH: 30

```
<212> TYPE: DNA
<213> ORGANISM: Artificial Sequence,primer
<220> FEATURE:
<221> NAME/KEY: misc_feature
<222> LOCATION: (1)..(30)
<223> OTHER INFORMATION: primer

<400> SEQUENCE: 8
gtccctgtct ctagtttgtc tgttcgagat                                              30

<210> SEQ ID NO 9
<211> LENGTH: 27
<212> TYPE: DNA
<213> ORGANISM: Artificial Sequence,primer
<220> FEATURE:
<221> NAME/KEY: misc_feature
<222> LOCATION: (1)..(27)
<223> OTHER INFORMATION: primer

<400> SEQUENCE: 9 gggatccac tagttctaga gatattc                                                  27

<210> SEQ ID NO 10
<211> LENGTH: 27
<212> TYPE: DNA
<213> ORGANISM: Artificial Sequence,primer
<220> FEATURE:
<221> NAME/KEY: misc_feature
<222> LOCATION: (1)..(27)
<223> OTHER INFORMATION: primer

<400> SEQUENCE: 10
ccttagacct ggagattcga agcgaag                                                 27

<210> SEQ ID NO 11
<211> LENGTH: 53
<212> TYPE: DNA
<213> ORGANISM: Artificial Sequence,primer
<220> FEATURE:
<221> NAME/KEY: misc_feature
<222> LOCATION: (1)..(53)
<223> OTHER INFORMATION: primer

<400> SEQUENCE: 11
ccaaacctac aggtggggtc tttcatttac aaggttatga gagcatcagc aac                    53

<210> SEQ ID NO 12
<211> LENGTH: 27
<212> TYPE: DNA
<213> ORGANISM: Artificial Sequence,primer
<220> FEATURE:
<221> NAME/KEY: misc_feature
<222> LOCATION: (1)..(27)
<223> OTHER INFORMATION: primer

<400> SEQUENCE: 12
aatgaaagac cccacctgta ggtttgg                                                 27

<210> SEQ ID NO 13
<211> LENGTH: 41
<212> TYPE: DNA
<213> ORGANISM: Artificial Sequence,primer
<220> FEATURE:
<221> NAME/KEY: misc_feature
<222> LOCATION: (1)..(41)
<223> OTHER INFORMATION: primer

<400> SEQUENCE: 13
```

-continued gtagagtgcc caattgccag tatacactcc gctatcgcta c                41

<210> SEQ ID NO 14
<211> LENGTH: 11299
<212> TYPE: DNA
<213> ORGANISM: Artificial Sequence
<220> FEATURE:
<221> NAME/KEY: misc_feature
<222> LOCATION: (1)..(11299)
<223> OTHER INFORMATION: plasmid
<308> DATABASE ACCESSION NUMBER: AX003194
<309> DATABASE ENTRY DATE: 2000-08-24
<313> RELEVANT RESIDUES: (1)..(11299)

<400> SEQUENCE: 14

```
ctaaattgta agcgttaata ttttgttaaa attcgcgtta aattttttgtt aaatcagctc      60
atttttaac caataggccg aaatcggcaa atcccttat aaatcaaaag aatagaccga       120
gatagggttg agtgttgttc cagtttggaa caagagtcca ctattaaaga acgtggactc     180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag      300
cccccgattt agagcttgac ggggaaagcc aacctggctt atcgaaatta atacgactca    360
ctatagggag accggcagat ctgagtccgt tacataactt acgtaaatg gcccgcctgg     420
ctgaccgccc aacgaccccc gcccattgac gtcaataatg acgtatgttc ccatagtaac    480
gccaataggg actttccatt gacgtcaatg gtgagtagt ttacggtaaa ctgcccactt      540
ggcagtacat caagtgtatc atatgccaag tacgccccct attgacgtca atgacggtaa    600
atggcccgcc tggcattatg cccagtacat gaccttatgg gactttccta cttggcagta    660
catctacgta ttagtcatcg ctattaccat ggtgatgcgg ttttggcagt acatcaatgg    720
gcgtggatag cggtttgact cacggggatt tccaagtctc cacccattg acgtcaatgg      780
gagtttgttt tggcaccaaa atcaacggga ctttccaaaa tgtcgtaaca actccgcccc    840
attgacgcaa atgggcggta ggcgtgtacg gtgggaggtc tatataagca gagctcgttt    900
agtgaaccgc gccagtcttc cgatagactg cgtcgcccgg gtacccgtat tcccaataaa     960
gcctcttgct gtttgcatcc gaatcgtggt ctcgctgttc cttgggaggg tctcctctga    1020
gtgattgact acccacgacg ggggtctttc atttctctag tttgtctgtt cgagatccta    1080
cagttggcgc ccgaacaggg acctgagagg ggcgcagacc ctacctgttg aacctggctg    1140
atcgtaggat cccccgggaca gcagaggaga acttacagaa gtcttctgga ggtgttcctg    1200
gccagaacac aggaggacag gtaagatggg agaccctttg acatggagca aggcgctcaa    1260
gaagttagag aaggtgacgg tacaagggtc tcagaaatta actactggta actgtaattg    1320
ggcgctaagt ctagtagact tatttcatga taccaacttt gtaaaagaaa aggactggca    1380
gctgagggat gtcattccat tgctggaaga tgtaactcag acgctgtcag gacaagaaag    1440
agaggccttt gaaagaacat ggtgggcaat ttctgctgta aagatgggcc tccagattaa    1500
taatgtagta gatggaaagg catcattcca gctcctaaga gcgaaatatg aaagaagac     1560
tgctaataaa aagcagtctg agccctctga agaatatctc tagagtgtga ttttaagggc    1620
gaattctgca ggagtgggga ggcacgatgg ccgctttggt cgaggcggat ccggccatta    1680
gccatattat tcattggtta tatagcataa atcaatattg gctattggcc attgcatacg    1740
ttgtatccta atcataatat gtacatttat attggctcat gtccaacatt accgccatgt    1800
tgacattgat tattgactag ttattaatag taatcaatta cggggtcatt agttcatagc    1860
```

```
ccatatatgg agttccgcgt tacataactt acggtaaatg gcccgcctgg ctgaccgccc   1920 aacgacccccc gcccattgac gtcaataatg acgtatgttc ccatagtaac gccaataggg   1980
actttccatt gacgtcaatg ggtggagtat ttacggtaaa ctgcccactt ggcagtacat   2040
caagtgtatc atatgccaag tacgccccct attgacgtca atgacggtaa atggcccgcc   2100
tggcattatg cccagtacat gaccttatgg actttcctac ttggcagta catctacgta   2160 ttagtcatcg ctattaccat ggtgatgcgg ttttggcagt acatcaatgg gcgtggatag   2220
cggtttgact cacggggatt tccaagtctc cacccccattg acgtcaatgg gagtttgttt   2280
tggcaccaaa atcaacggga ctttccaaaa tgtcgtaaca actccgcccc attgacgcaa   2340
atgggcggta ggcatgtacg gtgggaggtc tatataagca gagctcgttt agtgaaccgt   2400
cagatcgcct ggagacgcca tccacgctgt tttgacctcc atagaagaca ccgggaccga   2460
tccagcctcc gcggccccaa gcttcagctg ctcgaggatc tgcggatccg ggaattccc    2520 cagtctcagg atccaccatg ggggatcccg tcgttttaca acgtcgtgac tgggaaaacc   2580
ctggcgttac ccaacttaat cgccttgcag cacatcccccc tttcgccagc tggcgtaata   2640
gcgaagaggc ccgcaccgat cgcccttccc aacagttgcg cagcctgaat ggcgaatggc   2700
gctttgcctg gtttccggca ccagaagcgg tgccggaaag ctggctggag tgcgatcttc   2760
ctgaggccga tactgtcgtc gtcccctcaa actggcagat gcacggttac gatgcgccca   2820
tctacaccaa cgtaacctat cccattacgg tcaatccgcc gtttgttccc acggagaatc   2880
cgacgggttg ttactcgctc acatttaatg ttgatgaaag ctggctacag gaaggccaga   2940
cgcgaattat ttttgatggc gttaactcgg cgtttcatct gtggtgcaac gggcgctggg   3000
tcggttacgg ccaggacagt cgtttgccgt ctgaatttga cctgagcgca ttttacgcg    3060 ccggagaaaa ccgcctcgcg gtgatggtgc tgcgttggag tgacggcagt tatctggaag   3120
atcaggatat gtgcggatg agcggcattt tccgtgacgt ctcgttgctg cataaaccga   3180
ctacacaaat cagcgatttc catgttgcca ctcgctttaa tgatgatttc agccgcgctg   3240
tactggaggc tgaagttcag atgtgcggcg agttgcgtga ctacctacgg gtaacagttt   3300
ctttatggca gggtgaaacg caggtcgcca gcggcaccgc gccttcggc ggtgaaatta    3360 tcgatgagcg tggtggttat gccgatcgcg tcacactacg tctgaacgtc gaaaacccga   3420
aactgtggag cgccgaaatc ccgaatctct atcgtgcggt ggttgaactg cacaccgccg   3480
acggcacgct gattgaagca gaagcctgcg atgtcggttt ccgcgaggtg cggattgaaa   3540
atggtctgct gctgctgaac ggcaagccgt tgctgattcg aggcgttaac cgtcacgagc   3600
atcatcctct gcatggtcag gtcatggatg agcagacgat ggtgcaggat atcctgctga   3660
tgaagcagaa caactttaac gccgtgcgct gttcgcatta tccgaaccat ccgctgtggt   3720
acacgctgtg cgaccgctac ggcctgtatg tggtggatga agccaatatt gaaacccacg   3780
gcatggtgcc aatgaatcgt ctgaccgatg atccgcgctg gctaccggcg atgagcgaac   3840
gcgtaacgcg aatggtgcag cgcgatcgta atcacccgag tgtgatcatc tggtcgctgg   3900
ggaatgaatc aggccacggc gctaatcacg acgcgctgta tcgctggatc aaatctgtcg   3960
atccttcccg cccggtgcag tatgaaggcg gcggagccga caccacgcc accgatatta   4020 tttgcccgat gtacgcgcgc gtggatgaag accagcccct tccggctgtg ccgaaatggt   4080
ccatcaaaaa atggcttcg ctacctggag agacgcgccc gctgatcctt gcgaatacg    4140 cccacgcgat gggtaacagt cttggcggtt cgctaaaata ctggcaggcg tttcgtcagt   4200
atccccgttt acagggcggc ttcgtctggg actgggtgga tcagtcgctg attaaatatg   4260
```

```
atgaaaacgg caacccgtgg tcggcttacg gcggtgattt tggcgatacg ccgaacgatc    4320
gccagttctg tatgaacggt ctggtctttg ccgaccgcac gccgcatcca gcgctgacgg    4380
aagcaaaaca ccagcagcag tttttccagt tccgtttatc cgggcaaacc atcgaagtga    4440
ccagcgaata cctgttccgt catagcgata acgagctcct gcactggatg gtggcgctgg    4500
atggtaagcc gctggcaagc ggtgaagtgc ctctggatgt cgctccacaa ggtaaacagt    4560
tgattgaact gcctgaacta ccgcagccgg agagcgccgg gcaactctgg ctcacagtac    4620
gcgtagtgca accgaacgcg accgcatggt cagaagccgg gcacatcagc gcctggcagc    4680
agtggcgtct ggcggaaaac ctcagtgtga cgctccccgc cgcgtccac gccatcccgc     4740 atctgaccac cagcgaaatg gattttgca tcgagctggg taataagcgt tggcaattta     4800
accgccagtc aggctttctt tcacagatgt ggattggcga taaaaacaa ctgctgacgc      4860 cgctgcgcga tcagttcacc cgtgcaccgc tggataacga cattggcgta agtgaagcga    4920
cccgcattga ccctaacgcc tgggtcgaac gctggaaggc ggcgggccat taccaggccg    4980
aagcagcgtt gttgcagtgc acggcagata cacttgctga tgcggtgctg attacgaccg    5040
ctcacgcgtg gcagcatcag gggaaaacct tatttatcag ccggaaaacc taccggattg    5100
atggtagtgg tcaaatggcg attaccgttg atgttgaagt ggcgagcgat acaccgcatc    5160
cggcgcggat tggcctgaac tgccagctgg cgcaggtagc agagcgggta aactggctcg    5220
gattagggcc gcaagaaaac tatcccgacc gccttactgc cgcctgtttt gaccgctggg    5280
atctgccatt gtcagacatg tataccccgt acgtcttccc gagcgaaaac ggtctgcgct    5340
gcgggacgcg cgaattgaat tatggcccac cagtggcg cggcgacttc cagttcaaca     5400
tcagccgcta cagtcaacag caactgatgg aaaccagcca tcgccatctg ctgcacgcgg    5460
aagaaggcac atgctgaat atcgacggtt tccatatggg gattggtggc gacgactcct    5520
ggagcccgtc agtatcggcg gaattccagc tgagcgccgg tcgctaccat taccagttgg    5580
tctggtgtca aaataataa taaccgggca ggggggatcc gcagatccgg ctgtggaatg     5640
tgtgtcagtt agggtgtgga agtccccag gctccccagc aggcagaagt atgcaaagca    5700
tgcctgcagg aattcgatat caagcttatc gataccgtcg acctcgaggg ggggcccggt     5760
acccagcttt tgttcccttt agtgagggtt aattgcgcgg gaagtattta tcactaatca     5820
agcacaagta atacatgaga aactttact acagcaagca caatcctcca aaaaattttg      5880
tttttacaaa atccctggtg aacatgattg gaagggacct actagggtgc tgtggaaggg     5940
tgatggtgca gtagtagtta atgatgaagg aaagggaata attgctgtac cattaaccag    6000
gactaagtta ctaataaaac caaattgagt attgttgcag gaagcaagac ccaactacca    6060
ttgtcagctg tgtttcctga ggtctctagg aattgattac ctcgatgctt cattaaggaa    6120
gaagaataaa caaagactga aggcaatcca acaaggaaga caacctcaat atttgttata    6180
aggtttgata tatgggagta tttggtaaag gggtaacatg gtcagcatcg cattctatgg    6240
gggaatccca gggggaatct caaccccctat tacccaacag tcagaaaaat ctaagtgtga    6300
ggagaacaca atgtttcaac cttattgtta taataatgac agtaagaaca gcatggcaga    6360
atcgaaggaa gcaagagacc aagaaatgaa cctgaaagaa gaatctaaag aagaaaaaag    6420
aagaaatgac tggtggaaaa taggtatgtt tctgttatgc ttagcaggaa ctactggagg    6480
aatactttgg tggtatgaag gactcccaca gcaacattat atagggttgg tggcgatagg    6540
gggaagatta aacggatctg gccaatcaaa tgctatagaa tgctgggggtt ccttcccggg    6600
```

```
gtgtagacca tttcaaaatt acttcagtta tgagaccaat agaagcatgc atatggataa    6660
taatactgct acattattag aagctttaac caatataact gctctataaa taacaaaaca    6720
gaattagaaa catggaagtt agtaaagact tctggcataa ctcctttacc tatttcttct    6780
gaagctaaca ctggactaat tagacataag agagattttg gtataagtgc aatagtggca    6840
gctattgtag ccgctactgc tattgctgct agcgctacta tgtcttatgt tgctctaact    6900
gaggttaaca aaataatgga agtacaaaat catacttttg aggtagaaaa tagtactcta    6960
aatggtatgg atttaataga acgacaaata aagatattat atgctatgat tcttcaaaca    7020
catgcagatg ttcaactgtt aaaggaaaga caacaggtag aggagacatt taatttaatt    7080
ggatgtatag aaagaacaca tgtatttgt  catactggtc atccctggaa tatgtcatgg    7140
ggacatttaa atgagtcaac acaatgggat gactgggtaa gcaaaatgga agatttaaat    7200
caagagatac taactacact tcatggagcc aggaacaatt tggcacaatc catgataaca    7260
ttcaatacac cagatagtat agctcaattt ggaaaagacc tttggagtca tattggaaat    7320
tggattcctg gattgggagc ttccattata aaatatatag tgatgttttt gcttatttat    7380
ttgttactaa cctcttcgcc taagatcctc agggccctct ggaaggtgac cagtggtgca    7440
gggtcctccg gcagtcgtta cctgaagaaa aaattccatc acaaacatgc atcgcgagaa    7500
gacacctggg accaggccca acacaacata cacctagcag gcgtgaccgg tggatcaggg    7560
gacaaatact acaagcagaa gtactccagg aacgactgga atggagaatc agaggagtac    7620
aacaggcggc caaagagctg ggtgaagtca atcgaggcat ttggagagag ctatatttcc    7680
gagaagacca aggggagat ttctcagcct ggggcggcta tcaacgagca caagaacggc    7740
tctgggggga acaatcctca ccaagggtcc ttagacctgg agattcgaag cgaaggagga    7800
aacatttatg actgttgcat taaagcccaa gaaggaactc tcgctatccc ttgctgtgga    7860
tttcccttat ggctattttg gggactagta attatagtag gacgcatagc aggctatgga    7920
ttacgtggac tcgctgttat aataaggatt tgtattagag gcttaaattt gatatttgaa    7980
ataatcagaa aaatgcttga ttatattgga gagctttaa atcctggcac atctcatgta    8040
tcaatgcctc agtatgttta gaaaaacaag gggggaactg tggggttttt atgagggtt    8100 ttataaatga ttataagagt aaaaagaaag ttgctgatgc tctcataacc ttgtaaatga    8160
aagaccccac ctgtaggttt ggcaagctag cttaagtaac gccatttgc  aaggcatgga    8220 aaaatacata actgagaata gagaagttca gatcaaggtc aggaacagat ggaacagctg    8280
aatatgggcc aaacaggata tctgtggtaa gcagttcctg ccccggctca gggccaagaa    8340
cagatggaac agctgaatat gggccaaaca ggatatctgt ggtaagcagt tcctgccccg    8400
gctcagggcc aagaacagat ggtccccaga tgcggtccag ccctcagcag tttctagaga    8460
accatcagat gtttccaggg tgccccaagg acctgaaatg accctgtgcc ttatttgaac    8520
taaccaatca gttcgcttct cgcttctgtt cgcgcgcttc tgctccccga gctcaataaa    8580
agagcccaca cccctcact  cggggcgcca gtcctccgat tgactgagtc gcccgggtac    8640
ccgtgtatcc aataaaccct cttgcagttg catccgactt gtggtctcgc tgttccttgg    8700
gagggtctcc tctgagtgat tgactacccg tcagcggggg tctttcattt ggggggctcgt    8760 ccgggatcgg gagacccctg cccagggacc accgacccac caccgggagg taagctggct    8820
gcctcgcgcg tttcggtgat gacggtgaaa acctctgaca catgcagctc ccggagacgg    8880
tcacagcttg tctgtaagcg gatgccggga gcagacaagc ccgtcaggc  gcgtcagcgg    8940 gtgttggcgg gtgtcgggc  gcagccatga cccagtcacg tagcgatagc ggagtgtata    9000
```

```
ctggcaattg ggcactcaga ttctgcggtc tgagtccctt ctctgctggg ctgaaaaggc   9060
ctttgtaata aatataattc tctactcagt ccctgtctct agtttgtctg ttcgagatcc   9120
tacagagctc atgccttggc gtaatcatgg tcatagctgt ttcctgtgtg aaattgttat   9180
ccgctcacaa ttccacacaa catacgagcc ggaagcataa agtgtaaagc ctggggtgcc   9240
taatgagtga gctaactcac attaattgcg ttgcgctcac tgcccgcttt ccagtcggga   9300
aacctgtcgt gccagctgca ttaatgaatc ggccaacgcg cggggagagg cggtttgcgt   9360
attgggcgct cttccgcttc ctcgctcact gactcgctgc gctcggtcgt tcggctgcgg   9420
cgagcggtat cagctcactc aaaggcggta atacggttat ccacagaatc aggggataac   9480
gcaggaaaga acatgtgagc aaaaggccag caaaaggcca ggaaccgtaa aaaggccgcg   9540
ttgctggcgt ttttccatag gctccgcccc cctgacgagc atcacaaaaa tcgacgctca   9600
agtcagaggt ggcgaaaccc gacaggacta taaagatacc aggcgtttcc ccctggaagc   9660
tccctcgtgc gctctcctgt tccgaccctg ccgcttaccg gatacctgtc gcctttctc    9720 ccttcgggaa gcgtggcgct ttctcatagc tcacgctgta ggtatctcag ttcggtgtag   9780
gtcgttcgct ccaagctggg ctgtgtgcac gaaccccccg ttcagcccga ccgctgcgcc   9840
ttatccggta actatcgtct tgagtccaac ccggtaagac acgacttatc gccactggca   9900
gcagccactg gtaacaggat tagcagagcg aggtatgtag cggtgctac agagttcttg    9960 aagtggtggc ctaactacgg ctacactaga aggacagtat ttggtatctg cgctctgctg  10020
aagccagtta ccttcggaaa aagagttggt agctcttgat ccggcaaaca aaccaccgct  10080
ggtagcggtg gttttttgt ttgcaagcag cagattacgc gcagaaaaaa aggatctcaa    10140
gaagatcctt tgatctttc tacggggtct gacgctcagt ggaacgaaaa ctcacgttaa    10200
gggattttgg tcatgagatt atcaaaaagg atcttcacct agatcctttt aaattaaaaa   10260
tgaagtttta aatcaatcta agtatatat gagtaaactt ggtctgacag ttaccaatgc    10320
ttaatcagtg aggcacctat ctcagcgatc tgtctatttc gttcatccat agttgcctga  10380
ctccccgtcg tgtagataac tacgatacgg gagggcttac catctggccc cagtgctgca  10440
atgataccgc gagacccacg ctcaccggct ccagatttat cagcaataaa ccagccagcc  10500
ggaagggccg agcgcagaag tggtcctgca actttatccg cctccatcca gtctattaat  10560
tgttgccggg aagctagagt aagtagttcg ccagttaata gtttgcgcaa cgttgttgcc  10620
attgctacag gcatcgtggt gtcacgctcg tcgtttggta tggcttcatt cagctccggt  10680
tcccaacgat caaggcgagt tacatgatcc cccatgttgt gcaaaaaagc ggttagctcc  10740
ttcggtcctc cgatcgttgt cagaagtaag ttggccgcag tgttatcact catggttatg  10800
gcagcactgc ataattctct tactgtcatg ccatccgtaa gatgcttttc tgtgactggt  10860
gagtactcaa ccaagtcatt ctgagaatag tgtatgcggc gaccgagttg ctcttgcccg  10920
gcgtcaatac gggataatac cgcgccacat agcagaactt taaaagtgct catcattgga  10980
aaacgttctt cggggcgaaa actctcaagg atcttaccgc tgttgagatc cagttcgatg  11040
taacccactc gtgcacccaa ctgatcttca gcatctttta ctttcaccag cgtttctggg  11100
tgagcaaaaa caggaaggca aaatgccgca aaaaagggaa taagggcgac acggaaatgt  11160
tgaatactca tactcttcct ttttcaatat tattgaagca tttatcaggg ttattgtctc  11220
atgagcggat acatatttga atgtatttag aaaaataaac aatagggt tccgcgcaca    11280 tttccccgaa aagtgccac                                               11299
```

<210> SEQ ID NO 15
<211> LENGTH: 66
<212> TYPE: DNA
<213> ORGANISM: Artificial Sequence,primer
<220> FEATURE:
<221> NAME/KEY: misc_feature
<222> LOCATION: (1)..(66)
<223> OTHER INFORMATION: primer

<400> SEQUENCE: 15
atcgaagctt aattaaaagt agaaaatata ttctaattta ttgggcactc agttctgcgg    60
tctgag                                                               66

<210> SEQ ID NO 16
<211> LENGTH: 35
<212> TYPE: DNA
<213> ORGANISM: Artificial Sequence,primer
<220> FEATURE:
<221> NAME/KEY: misc_feature
<222> LOCATION: (1)..(35)
<223> OTHER INFORMATION: primer

<400> SEQUENCE: 16
tcagctgcag ttcgggcgcc aactgtagga tctcg                               35

<210> SEQ ID NO 17
<211> LENGTH: 33
<212> TYPE: DNA
<213> ORGANISM: Artificial Sequence,primer
<220> FEATURE:
<221> NAME/KEY: misc_feature
<222> LOCATION: (1)..(33)
<223> OTHER INFORMATION: primer

<400> SEQUENCE: 17
actgctgcag agattcgaag cgaaggagga aac                                 33

<210> SEQ ID NO 18
<211> LENGTH: 31
<212> TYPE: DNA
<213> ORGANISM: Artificial Sequence,primer
<220> FEATURE:
<221> NAME/KEY: misc_feature
<222> LOCATION: (1)..(31)
<223> OTHER INFORMATION: primer

<400> SEQUENCE: 18
tgtggggttt ccatgagggg ttttataaat g                                   31

<210> SEQ ID NO 19
<211> LENGTH: 30
<212> TYPE: DNA
<213> ORGANISM: Artificial Sequence,primer
<220> FEATURE:
<221> NAME/KEY: misc_feature
<222> LOCATION: (1)..(30)
<223> OTHER INFORMATION: primer

<400> SEQUENCE: 19
ccctcatgga aacccacgt tccccccttg                                      30

<210> SEQ ID NO 20
<211> LENGTH: 33
<212> TYPE: DNA
<213> ORGANISM: Artificial Sequence,primer
<220> FEATURE:
<221> NAME/KEY: misc_feature

```
<222> LOCATION: (1)..(33)
<223> OTHER INFORMATION: primer

<400> SEQUENCE: 20
ctgaagatct gaatctgagt gcccaattgt cag                                   33

<210> SEQ ID NO 21
<211> LENGTH: 23
<212> TYPE: DNA
<213> ORGANISM: Artificial Sequence,primer
<220> FEATURE:
<221> NAME/KEY: misc_feature
<222> LOCATION: (1)..(23)
<223> OTHER INFORMATION: primer

<400> SEQUENCE: 21
ctgacaattg ggcactcaga ttc                                             23

<210> SEQ ID NO 22
<211> LENGTH: 44
<212> TYPE: DNA
<213> ORGANISM: Artificial Sequence,primer
<220> FEATURE:
<221> NAME/KEY: misc_feature
<222> LOCATION: (1)..(44)
<223> OTHER INFORMATION: primer

<400> SEQUENCE: 22
catgagatct taaaaaaaaa tgatgagaga attatattta ttac                       44

<210> SEQ ID NO 23
<211> LENGTH: 21
<212> TYPE: DNA
<213> ORGANISM: Equine infectious anemia virus
<220> FEATURE:
<221> NAME/KEY: misc_feature
<222> LOCATION: (1)..(21)

<400> SEQUENCE: 23
gggcactcag attctgcggt c                                               21

<210> SEQ ID NO 24
<211> LENGTH: 77
<212> TYPE: DNA
<213> ORGANISM: Equine infectious anemia virus

<400> SEQUENCE: 24
cuagugauuc ugagugcccc ugaugagcgg ccgaaaggcc gcgaaaccug cguacgacac     60
gcaggucggg cactcag                                                    77

<210> SEQ ID NO 25
<211> LENGTH: 50
<212> TYPE: DNA
<213> ORGANISM: Artificial Sequence
<220> FEATURE:
<221> NAME/KEY: promoter
<222> LOCATION: (13)..(29)
<223> OTHER INFORMATION: T7 promoter

<400> SEQUENCE: 25
atcgttaatt aataatacga ctcactatag ggcactcaga ttctgcggtc                50

<210> SEQ ID NO 26
<211> LENGTH: 82
<212> TYPE: DNA
<213> ORGANISM: Artificial Sequence
```

-continued

```
<220> FEATURE:
<221> NAME/KEY: terminator
<222> LOCATION: (11)..(59)
<223> OTHER INFORMATION: T7 termination sequence

<400> SEQUENCE: 26
catgagatct caaaaaaccc ctcaagaccc gtttagaggc cccaagggt tatgctagtg    60 atgagagaat tatatttatt ac                                             82

<210> SEQ ID NO 27
<211> LENGTH: 7252
<212> TYPE: DNA
<213> ORGANISM: Artificial Sequence, plasmid
<220> FEATURE:
<221> NAME/KEY: misc_feature
<222> LOCATION: (1)..(7252)
<223> OTHER INFORMATION: plasmid vector
<300> PUBLICATION INFORMATION:
<308> DATABASE ACCESSION NUMBER: AX003206
<309> DATABASE ENTRY DATE: 2000-08-24
<313> RELEVANT RESIDUES: (1)..(7252)

<400> SEQUENCE: 27
agcttttgcg atcaataaat ggatcacaac cagtatctct taacgatgtt cttcgcagat    60
gatgattcat tttttaagta tttggctagt caagatgatg aaatcttcat tatctgatat   120
attgcaaatc actcaatatc tagactttct gttattatta ttgatccaat caaaaaataa   180
attagaagcc gtgggtcatt gttatgaatc tctttcagag gaatacagac aattgacaaa   240
attcacagac tttcaagatt ttaaaaaact gtttaacaag gtccctattg ttacagatgg   300
aagggtcaaa cttaataaag gatatttgtt cgactttgtg attagtttga tgcgattcaa   360
aaaagaatcc tctctagcta ccaccgcaat agatcctgtt agatacatag atcctcgtcg   420
caatatcgca ttttctaacg tgatggatat attaaagtcg aataaagtga acaataatta   480
attctttatt gtcatcatga acggcggaca tattcagttg ataatcggcc ccatgttttc   540
aggtaaaagt acagaattaa ttagacgagt tagacgttat caaatagctc aatataaatg   600
cgtgactata aaatattcta acgataatag atacggaacg ggactatgga cgcatgataa   660
gaataatttt gaagcattgg aagcaactaa actatgtgat ctcttggaat caattacaga   720
tttctccgtg ataggtatcg atgaaggaca gttctttcca gacattgttg aattagatcg   780
ataaaaatta attaattacc cgggtaccag gcctagatct gtcgacttcg agcttattta   840
tattccaaaa aaaaaaata aaatttcaat ttttaagctt tcactaattc caaacccacc   900
cgctttttat agtaagtttt tcacccataa ataataaata caataattaa tttctcgtaa   960
aagtagaaaa tatattctaa tttattgcac ggtaaggaag tagatcataa ctcgagcatg  1020
ggagatcccg tcgttttaca acgtcgtgac tgggaaaacc ctggcgttac ccaacttaat  1080
cgccttgcag cacatccccc tttcgccagc tggcgtaata gcgaagaggc ccgcaccgat  1140
cgcccttccc aacagttgcg cagcctgaat ggcgaatggc gctttgcctg gtttccggca  1200
ccagaagcgg tgccggaaag ctggctggag tgcgatcttc ctgaggccga tactgtcgtc  1260
gtcccctcaa actggcagat gcacggttac gatgcgccca tctacaccaa cgtaacctat  1320
cccattacgt caatccgcc gtttgttccc acgagaatc cgacgggttg ttactcgctc  1380
acatttaatg ttgatgaaag ctggctacag gaaggccaga cgcgaattat ttttgatggc  1440
gttaactcgg cgtttcatct gtggtgcaac gggcgctggg tcggttacgg ccaggacagt  1500
cgtttgccgt ctgaatttga cctgagcgca ttttacgcg ccggagaaaa ccgcctcgcg  1560
```

-continued

```
gtgatggtgc tgcgttggag tgacggcagt tatctggaag atcaggatat gtggcggatg    1620
agcggcattt tccgtgacgt ctcgttgctg cataaaccga ctacacaaat cagcgatttc    1680
catgttgcca ctcgctttaa tgatgatttc agccgcgctg tactggaggc tgaagttcag    1740
atgtgcggcg agttgcgtga ctacctacgg gtaacagttt ctttatggca gggtgaaacg    1800
caggtcgcca gcggcaccgc gcctttcggc ggtgaaatta tcgatgagcg tggtggttat    1860
gccgatcgcg tcacactacg tctcaacgtc gaaaacccga actgtggag cgccgaaatc    1920 ccgaatctct atcgtgcggt ggttgaactg cacaccgccg acggcacgct gattgaagca    1980
gaagcctgcg atgtcggttt ccgcgaggtg cggattgaaa atggtctgct gctgctgaac    2040
ggcaagccgt tgctgattcg aggcgttaac cgtcacgagc atcatcctct gcatggtcag    2100
gtcatggatg agcagacgat ggtgcaggat atcctgctga tgaagcagaa caactttaac    2160
gccgtgcgct gttcgcatta ccgaaccat ccgctgtggt acacgctgtg cgaccgctac    2220
ggcctgtatg tggtggatga agccaatatt gaaacccacg gcatggtgcc aatgaatcgt    2280
ctgaccgatg atccgcgctg gctaccggcg atgagcgaac gcgtaacgcg aatggtgcag    2340
cgcgatcgta atcacccgag tgtgatcatc tggtcgctgg ggaatgaatc aggccacggc    2400
gctaatcacg acgcgctgta tcgctggatc aaatctgtcg atccttcccg cccggtgcag    2460
tatgaaggcg gcggagccga caccacggcc accgatatta tttgcccgat gtacgcgcgc    2520
gtggatgaag accagccctt cccggctgtg ccgaaatggt ccatcaaaaa atggctttcg    2580
ctacctggag agacgcgccc gctgatcctt tgcgaatacg cccacgcgat gggtaacagt    2640
cttggcggtt tcgctaaata ctggcaggcg tttcgtcagt atccccgttt acagggcggc    2700
ttcgtctggg actgggtgga tcagtcgctg attaaatatg atgaaaacgg caacccgtgg    2760
tcggcttacg gcggtgattt tggcgatacg ccgaacgatc gccagttctg tatgaacggt    2820
ctggtctttg ccgaccgcac gccgcatcca gcgctgacgg aagcaaaaca ccagcagcag    2880
tttttccagt tccgtttatc cgggcaaacc atcgaagtga ccagcgaata cctgttccgt    2940
catagcgata acgagctcct gcactggatg gtggcgctgg atggtaagcc gctggcaagc    3000
ggtgaagtgc ctctggatgt cgctccacaa ggtaaacagt tgattgaact gcctgaacta    3060
ccgcagccga gagcgccgg gcaactctgg ctcacagtac gcgtagtgca accgaacgcg    3120
accgcatggt cagaagccgg gcacatcagc gcctggcagc agtggcgtct ggcggaaaac    3180
ctcagtgtga cgctccccgc cgcgtcccac gccatcccgc atctgaccac cagcgaaatg    3240 gattttttgca tcgagctggg taataagcgt tggcaattta accgccagtc aggctttctt    3300
tcacagatgt ggattggcga taaaaaacaa ctgctgacgc cgctgcgcga tcagttcacc    3360
cgtgcaccgc tggataacga cattggcgta agtgaagcga cccgcattga ccctaacgcc    3420
tgggtcgaac gctggaaggc ggcgggccat taccaggccg aagcagcgtt gttgcagtgc    3480
acggcagata cacttgctga tgcggtgctg attacgaccg ctcacgcgtg gcagcatcag    3540
gggaaaacct tatttatcag ccggaaaacc taccggattg atggtagtgg tcaaatggcg    3600
attaccgttg atgttgaagt ggcgagcgat acaccgcatc cggcgcggat tggcctgaac    3660
tgccagctgg cgcaggtagc agagcgggta aactggctcg gattagggcc gcaagaaaac    3720
tatcccgacc gccttactgc cgcctgtttt gaccgctggg atctgccatt gtcagacatg    3780
tataccccgt acgtcttccc gagcgaaaac ggtctgcgct gcgggacgcg cgaattgaat    3840
tatggcccac accagtggcg cggcgacttc cagttcaaca tcagccgcta cagtcaacag    3900
caactgatgg aaaccagcca tcgccatctg ctgcacgcgg aagaaggcac atggctgaat    3960
```

-continued

```
atcgacggtt tccatatggg gattggtggc gacgactcct ggagcccgtc agtatcggcg    4020
gaattcagct gagcgccggt cgctaccatt accagttggt ctggtgtcaa aaataataat    4080
aaccgggcag gggggatcct tctgtgagcg tatggcaaac gaaggaaaaa tagttatagt    4140
agccgcactc gatgggacat ttcaacgtaa accgtttaat aatattttga atcttattcc    4200
attatctgaa atggtggtaa aactaactgc tgtgtgtatg aaatgcttta aggaggcttc    4260
cttttctaaa cgattgggtg aggaaaccga gatagaaata ataggaggta atgatatgta    4320
tcaatcggtg tgtagaaagt gttacatcga ctcataatat tatattttt atctaaaaaa    4380 ctaaaaataa acattgatta aattttaata taatacttaa aaatggatgt tgtgtcgtta    4440
gataaaccgt ttatgtattt tgaggaaatt gataatgagt tagattacga accagaaagt    4500
gcaaatgagg tcgcaaaaaa actgccgtat caaggacagt taaaactatt actaggagaa    4560 ttatttttc ttagtaagtt acagcgacac ggtatattag atggtgccac cgtagtgtat    4620
ataggatctg ctcccggtac acatatacgt tatttgagag atcatttcta taatttagga    4680
gtgatcatca aatggatgct aattgacggc cgccatcatg atcctatttt aaatggattg    4740
cgtgatgtga ctctagtgac tcggttcgtt gatgaggaat atctacgatc catcaaaaaa    4800
caactgcatc cttctaagat tattttaatt tctgatgtga gatccaaacg aggaggaaat    4860
gaacctagta cggcggattt actaagtaat tacgctctac aaaatgtcat gattagtatt    4920
ttaaaccccg tggcgtctag tcttaaatgg agatgcccgt ttccagatca atggatcaag    4980 gactttata tcccacacgg taataaaatg ttacaacctt ttgctccttc atattcagct    5040
gaaatgagat tattaagtat ttataccggt gagaacatga gactgactcg ggccgcgttg    5100
ctggcgtttt tccataggct ccgcccccct gacgagcatc acaaaaatcg acgctcaagt    5160
cagaggtggc gaaacccgac aggactataa agataccagg cgtttccccc tggaagctcc    5220
ctcgtgcgct ctcctgttcc gaccctgccg cttaccggat acctgtccgc ctttctccct    5280 tcggaagcg tggcgctttc tcaatgctca cgctgtaggt atctcagttc ggtgtaggtc    5340
gttcgctcca agctgggctg tgtgcacgaa ccccccgttc agcccgaccg ctgcgcctta    5400
tccggtaact atcgtcttga gtccaacccg gtaagcacg acttatcgcc actggcagca    5460
gccactggta acaggattag cagagcgagg tatgtaggcg gtgctacaga gttcttgaag    5520
tggtggccta actacggcta cactagaagg acagtatttg gtatctgcgc tctgctgaag    5580
ccagttacct tcggaaaaag agttggtagc tcttgatccg gcaaacaaac caccgctggt    5640
agcggtggtt ttttgttg caagcagcag attacgcgca gaaaaaaagg atctcaagaa    5700
gatcctttga tcttttctac ggggtctgac gctcagtgga acgaaaactc acgttaaggg    5760
attttggtca tgagattatc aaaaaggatc ttcacctaga tccttttaaa ttaaaaatga    5820
agttttaaat caatctaaag tatatatgag taaacttggt ctgacagtta ccaatgctta    5880
atcagtgagg cacctatctc agcgatctgt ctatttcgtt catccatagt tgcctgactc    5940
cccgtcgtgt agataactac gatacgggag ggcttaccat ctggccccag tgctgcaatg    6000
ataccgcgag acccacgctc accggctcca gatttatcag caataaacca gccagccgga    6060
agggccgagc gcagaagtgg tcctgcaact ttatccgcct ccatccagtc tattaattgt    6120
tgccgggaag ctagagtaag tagttcgcca gttaatagtt tgcgcaacgt tgttgccatt    6180
gctgcaggca tcgtggtgtc acgctcgtcg tttggtatgg cttcattcag ctccggttcc    6240
caacgatcaa ggcgagttac atgatccccc atgttgtgca aaaaagcggt tagctccttc    6300
```

-continued

```
ggtcctccga tcgttgtcag aagtaagttg gccgcagtgt tatcactcat ggttatggca    6360
gcactgcata attctcttac tgtcatgcca tccgtaagat gcttttctgt gactggtgag    6420
tactcaacca agtcattctg agaatagtgt atgcggcgac cgagttgctc ttgcccggcg    6480
tcaacacggg ataataccgc gccacatagc agaactttaa aagtgctcat cattggaaaa    6540
cgttcttcgg ggcgaaaact ctcaaggatc ttaccgctgt tgagatccag ttcgatgtaa    6600
cccactcgtg cacccaactg atcttcagca tcttttactt tcaccagcgt ttctgggtga    6660
gcaaaaacag gaaggcaaaa tgccgcaaaa aagggaataa gggcgacacg gaaatgttga    6720
atactcatac tcttcctttt tcaatattat tgaagcattt atcagggtta ttgtctcatg    6780
agcggataca tatttgaatg tatttagaaa aataaacaaa taggggttcc gcgcacattt    6840
ccccgaaaag tgccacctga cgtctaagaa accattatta tcatgacatt aacctataaa    6900
aataggcgta tcacgaggcc ctttcgtctt cgaataaata cctgtgacgg aagatcactt    6960
cgcagaataa ataaatcctg gtgtccctgt tgataccggg aagccctggg ccaacttttg    7020
gcgaaaatga gacgttgatc ggcacgtaag aggttccaac tttcaccata tgaaataag    7080 atcactaccg ggcgtatttt ttgagttatc gagattttca ggagctaagg aagctaaaat    7140
ggagaaaaaa atcactggat ataccaccgt tgatatatcc caatggcatc gtaaagaaca    7200
ttttgaggca tttcagtcag ttgctcaatg tacctataac cagaccgttc ag            7252
```

<210> SEQ ID NO 28
<211> LENGTH: 7387
<212> TYPE: DNA
<213> ORGANISM: Artificial Sequence, primer
<220> FEATURE:
<221> NAME/KEY: misc_feature
<222> LOCATION: (1)..(7387)
<223> OTHER INFORMATION: plasmid vector
<300> PUBLICATION INFORMATION:
<308> DATABASE ACCESSION NUMBER: AX003207
<309> DATABASE ENTRY DATE: 2000-08-24
<313> RELEVANT RESIDUES: (1)..(7387)

<400> SEQUENCE: 28

```
cctcctgaaa aactggaatt taatacacca tttgtgttca tcatcagaca tgatattact      60
ggatttatat tgtttatggg taaggtagaa tctccttaat atgggtacgg tgtaaggaat     120
cattatttta tttatattga tgggtacgtg aaatctgaat tttcttaata aatattattt     180
ttattaaatg tgtatatgtt gttttgcgat agccatgtat ctactaatca gatctattag     240
agatattatt aattctggtg caatatgaca aaaattatac actaattagc gtctcgtttc     300
agacatggat ctgtcacgaa ttaatacttg aagtctaag cagctgaaaa gctttctctc     360
tagcaaagat gcatttaagg cggatgtcca tggacatagt gccttgtatt atgcaatagc     420
tgataataac gtgcgtctag tatgtacgtt gttgaacgct ggagcattga aaaatcttct     480
agagaatgaa tttccattac atcaggcagc acattggaa gataccaaaa tagtaaagat     540
tttggctatt cagtggactg gatgattcga ggtacccgat ccccctgcc cggttattat     600 tatttttgac accagaccaa ctggtaatgg tagcgaccgg cgctcagctg aattccgccg     660
atactgacgg gctccaggag tcgtcgccac caatccccat atggaaaccg tcgatattca     720
gccatgtgcc ttcttccgcg tgcagcagat ggcgatggct ggtttccatc agttgctgtt     780
gactgtagcg gctgatgttg aactggaagt cgccgcgcca ctggtgtggg ccataattca     840
attcgcgcgt cccgcagcgc agaccgtttt cgctcggaa gacgtacggg gtatacatgt     900
ctgacaatgg cagatcccag cggtcaaaac aggcggcagt aaggcggtcg ggatagtttt     960
```

-continued

```
cttgcggccc taatccgagc cagtttaccc gctctgctac ctgcgccagc tggcagttca    1020
ggccaatccg cgccggatgc ggtgtatcgc tcgccacttc aacatcaacg gtaatcgcca    1080
tttgaccact accatcaatc cggtaggttt tccggctgat aaataaggtt ttccctgat     1140 gctgccacgc gtgagcggtc gtaatcagca ccgcatcagc aagtgtatct gccgtgcact    1200
gcaacaacgc tgcttcggcc tggtaatggc ccgccgcctt ccagcgttcg acccaggcgt    1260
tagggtcaat gcgggtcgct tcacttacgc caatgtcgtt atccagcggt gcacgggtga    1320
actgatcgcg cagcggcgtc agcagttgtt ttttatcgcc aatccacatc tgtgaaagaa    1380
agcctgactg gcggttaaat tgccaacgct tattacccag ctcgatgcaa aaatccattt    1440
cgctggtggt cagatgcggg atggcgtggg acgcggcggg gagcgtcaca ctgaggtttt    1500
ccgccagacg ccactgctgc caggcgctga tgtgcccggc ttctgaccat gcggtcgcgt    1560
tcggttgcac tacgcgtact gtgagccaga gttgcccggc gctctccggc tgcggtagtt    1620
caggcagttc aatcaactgt ttaccttgtg gagcgacatc cagaggcact tcaccgcttg    1680
ccagcggctt accatccagc gccaccatcc agtgcaggag ctcgttatcg ctatgacgga    1740
acaggtattc gctggtcact tcgatggttt gcccggataa acggaactgg aaaaactgct    1800
gctggtgttt tgcttccgtc agcgctggat gcggcgtgcg gtcggcaaag accagaccgt    1860
tcatacagaa ctggcgatcg ttcggcgtat cgccaaaatc accgccgtaa gccgaccacg    1920
ggttgccgtt tcatcatat ttaatcagcg actgatccac ccagtcccag cgaagccgc     1980 cctgtaaacg gggatactga cgaaacgcct gccagtattt agcgaaaccg ccaagactgt    2040
tacccatcgc gtgggcgtat cgcaaagga tcagcgggcg cgtctctcca ggtagcgaaa    2100 gccattttt gatggaccat ttcggcacag ccgggaaggg ctggtcttca tccacgcgcg    2160
cgtacatcgg gcaaataata tcggtggccg tggtgtcggc tccgccgcct tcatactgca    2220
ccgggcggga aggatcgaca gatttgatcc agcgatacag cgcgtcgtga ttagcgccgt    2280
ggcctgattc attccccagc gaccagatga tcacactcgg gtgattacga tcgcgctgca    2340
ccattcgcgt tacgcgttcg ctcatcgccg gtagccagcg cggatcatcg gtcagacgat    2400
tcattggcac catgccgtgg gtttcaatat tggcttcatc caccacatac aggccgtagc    2460
ggtcgcacag cgtgtaccac agcggatggt tcggataatg cgaacagcgc acggcgttaa    2520
agttgttctg cttcatcagc aggatatcct gcaccatcgt ctgctcatcc atgacctgac    2580
catgcagagg atgatgctcg tgacggttaa cgcctcgaat cagcaacggc ttgccgttca    2640
gcagcagcag accattttca atccgcacct cgcggaaacc gacatcgcag gcttctgctt    2700
caatcagcgt gccgtcggcg gtgtgcagtt caaccaccgc acgatagaga ttcgggattt    2760
cggcgctcca cagtttcggg ttttcgacgt tgagacgtag tgtgacgcga tcggcataac    2820
caccacgctc atcgataatt tcaccgccga aaggcgcggt gccgctggcg acctgcgttt    2880
caccctgcca taaagaaact gttacccgta ggtagtcacg caactcgccg cacatctgaa    2940
cttcagcctc cagtacagcg cggctgaaat catcattaaa gcgagtggca acatggaaat    3000
cgctgatttg tgtagtcggt ttatgcagca acgagacgtc acggaaaatg ccgctcatcc    3060
gccacatatc ctgatcttcc agataactgc cgtcactcca acgcagcacc atcaccgcga    3120
ggcggttttc tccggcgcgt aaaaatgcgc tcaggtcaaa ttcagacggc aaacgactgt    3180
cctggccgta accgacccag cgcccgttgc accacagatg aaacgccgag ttaacgccat    3240
caaaaataat tcgcgtctgg ccttcctgta gccagctttc atcaacatta aatgtgagcg    3300
```

```
agtaacaacc cgtcggattc tccgtgggaa caaacggcgg attgaccgta atgggatagg    3360
ttacgttggt gtagatgggc gcatcgtaac cgtgcatctg ccagtttgag gggacgacga    3420
cagtatcggc tcaggaaga tcgcactcca gccagctttc cggcaccgct tctggtgccg     3480
gaaaccaggc aaagcgccat tcgccattca ggctgcgcaa ctgttgggaa gggcgatcgg    3540
tgcgggcctc ttcgctatta cgccagctgg cgaaagggg atgtgctgca aggcgattaa     3600
gttgggtaac gccagggttt tcccagtcac gacgttgtaa aacgacggga tctcccatgc    3660
tcgagttatg atctacttcc ttaccgtgca ataaattaga atatatttc tacttttacg     3720 agaaattaat tattgtattt attatttatg ggtgaaaaac ttactataaa aagcgggtgg    3780
gtttggaatt agtgaaagct gggagatctg gcgcgcctgc agagaattcg tttaaacgga    3840
tcccgagctt atttatattc caaaaaaaaa aaataaaatt tcaatttta agctggggat      3900 cctctagagt cgacctgcag gcatgctcga gcggccgcca gtgtgatgga tatctgcaga    3960
attcggcttg gggggctgca ggtggatgcg atcatgacgt cctctgcaat ggataacaat    4020
gaacctaaag tactagaaat ggtatatgat gctacaattt tacccgaagg tagtagcatg    4080
gattgtataa acagacacat caatatgtgt atacaacgca cctatagttc tagtataatt    4140
gccatattgg atagattcct aatgatgaac aaggatgaac taaataatac acagtgtcat    4200
ataattaaag aatttatgac atacgaacaa atggcgattg accattatgg agaatatgta    4260
aacgctattc tatatcaaat tcgtaaaaga cctaatcaac atcacaccat taatctgttt    4320
aaaaaaataa aaagaacccg gtatgacact tttaaagtgg atcccgtaga attcgtaaaa    4380
aaagttatcg gatttgtatc tatcttgaac aaatataaac cggtttatag ttacgtcctg    4440
tacgagaacg tcctgtacga tgagttcaaa tgtttcattg actacgtgga aactaagtat    4500
ttctaaaatt aatgatgcat taattttgt attgattctc aatcctaaaa actaaaatat      4560
gaataagtat taaacatagc ggtgtactaa ttgatttaac ataaaaata gttgttaact      4620 aatcatgagg actctactta ttagatatat tctttggaga aatgacaacg atcaaaccgg    4680
gcatgcaagc ttgtctccct atagtgagtc gtattagagc ttggcgtaat catggtcata    4740
gctgtttcct gtgtgaaatt gttatccgct cacaattcca cacaacatac gagccggaag    4800
cataaagtgt aaagcctggg gtgcctaatg agtgagctaa ctcacattaa ttgcgttgcg    4860
ctcactgccc gctttcgagt cgggaaacct gtcgtgccag ctgcattaat gaatcggcca    4920
acgcgcgggg agaggcggtt tgcgtattgg gcgctcttcc gcttcctcgc tcactgactc    4980
gctgcgctcg tcgttcggc tgcggcgagc ggtatcagct cactcaaagg cggtaatacg     5040
gttatccaca gaatcagggg ataacgcagg aaagaacatg tgagcaaaag gccagcaaaa    5100
ggccaggaac cgtaaaaagg ccgcgttgct ggcgtttttc gataggctcc gcccccctga    5160
cgagcatcac aaaaatcgac gctcaagtca gaggtggcga aacccgacag gactataaag    5220
ataccaggcg tttccccctg gaagctccct cgtgcgctct cctgttccga ccctgccgct    5280
taccggatac ctgtccgcct ttctcccttc gggaagcgtg cgctttctc atagctcacg     5340 ctgtaggtat ctcagttcgg tgtaggtcgt tcgctccaag ctgggctgtg tgcacgaacc    5400
ccccgttcag cccgaccgct gcgccttatc cggtaactat cgtcttgagt ccaacccggt    5460
aagacacgac ttatcgccac tggcagcagc cactggtaac aggattagca gagcgaggta    5520
tgtaggcggt gctacagagt tcttgaagtg gtggcctaac tacggctaca ctagaaggac    5580
agtatttggt atctgcgctc tgctgaagcc agttaccttc ggaaaaagag ttggtagctc    5640
ttgatccggc aaacaaacca ccgctggtag cggtggtttt tttgtttgca agcagcagat    5700
```

```
tacgcgcaga aaaaaaggat ctcaagaaga tcctttgatc ttttctacgg ggtctgacgc    5760
tcagtggaac gaaaactcac gttaagggat tttggtcatg agattatcaa aaaggatctt    5820
cacctagatc cttttaaatt aaaaatgaag ttttaaatca atctaaagta tatatgagta    5880
aacttggtct gacagttacc aatgcttaat cagtgaggca cctatctcag cgatctgtct    5940
atttcgttca tccatagttg cctgactccc cgtcgtgtag ataactacga tacgggaggg    6000
cttaccatct ggccccagtg ctgcaatgat accgcgagac ccacgctcac cggctccaga    6060
tttatcagca ataaaccagc cagccggaag ggccgagcgc agaagtggtc ctgcaacttt    6120
atccgcctcc atccagtcta ttaattgttg ccgggaagct agagtaagta gttcgccagt    6180
taatagtttg cgcaacgttg ttggcattgc tacaggcatc gtggtgtcac gctcgtcgtt    6240
tggtatggct tcattcagct ccggttccca acgatcaagg cgagttacat gatccccat     6300 gttgtgcaaa aaagcggtta gctccttcgg tcctccgatc gttgtcagaa gtaagttggc    6360
cgcagtgtta tcactcatgg ttatggcagc actgcataat tctcttactg tcatgccatc    6420
cgtaagatgc ttttctgtga ctggtgagta ctcaaccaag tcattctgag aatagtgtat    6480
gcggcgaccg agttgctctt gcccggcgtc aatacgggat aataccgcgc cacatagcag    6540
aactttaaaa gtgctcatca ttggaaaacg ttcttcgggg cgaaaactct caaggatctt    6600
accgctgttg agatccagtt cgatgtaacc cactcgtgca cccaactgat cttcagcatc    6660
ttttactttc accagcgttt ctgggtgagc aaaaacagga aggcaaaatg ccgcaaaaaa    6720
gggaataagg gcgacacgga aatgttgaat actcatactc ttcctttttc aatattattg    6780
aagcatttat cagggttatt gtctcatgag cggatacata tttgaatgta tttagaaaaa    6840
taaacaaata ggggttccgc gcacatttcc ccgaaaagtg ccacctgacg tctaagaaac    6900
cattattatc atgacattaa cctataaaaa taggcgtatc acgaggccct ttcgtctcgc    6960
gcgtttcggt gatgacggtg aaaacctctg acacatgcag ctcccggaga cggtcacagc    7020
ttgtctgtaa gcggatgccg ggagcagaca agcccgtcag ggcgcgtcag cgggtgttgg    7080
cgggtgtcgg ggctggctta actatgcggc atcagagcag attgtactga gagtgcacca    7140
tatgcggtgt gaaataccgc acagatgcgt aaggagaaaa taccgcatca ggcgccattc    7200
gccattcagg ctgcgcaact gttgggaagg gcgatcggtg cgggcctctt cgctattacg    7260
ccagctggcg aaagggggat gtgctgcaag gcgattaagt tgggtaacgc cagggttttc    7320
ccagtcacga cgttgtaaaa cgacggccag tgaattggat ttaggtgaca ctatagaata    7380
cgaattc                                                             7387
```

<210> SEQ ID NO 29
<211> LENGTH: 27
<212> TYPE: DNA
<213> ORGANISM: Artificial Sequence, primer
<220> FEATURE:
<221> NAME/KEY: misc_feature
<222> LOCATION: (1)..(27)
<223> OTHER INFORMATION: primer

<400> SEQUENCE: 29

```
gcatggacct gtgggttttt tatgagg                                         27
```

<210> SEQ ID NO 30
<211> LENGTH: 29
<212> TYPE: DNA
<213> ORGANISM: Artificial Sequence, primer
<220> FEATURE:

```
<221> NAME/KEY: misc_feature
<222> LOCATION: (1)..(29)
<223> OTHER INFORMATION: primer

<400> SEQUENCE: 30
gcatgagctc tgtaggatct cgaacagac                                    29

<210> SEQ ID NO 31
<211> LENGTH: 33
<212> TYPE: DNA
<213> ORGANISM: Artificial Sequence, primer
<220> FEATURE:
<221> NAME/KEY: misc_feature
<222> LOCATION: (1)..(33)
<223> OTHER INFORMATION: primer

<400> SEQUENCE: 31
gactacgact agtgtatgtt tagaaaaaca agg                               33

<210> SEQ ID NO 32
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: primer

<400> SEQUENCE: 32
ctaggctact agtactgtag gatctcgaac ag                                32

<210> SEQ ID NO 33
<211> LENGTH: 33
<212> TYPE: DNA
<213> ORGANISM: Artificial Sequence, primer
<220> FEATURE:
<221> NAME/KEY: misc_feature
<222> LOCATION: (1)..(33)
<223> OTHER INFORMATION: primer

<400> SEQUENCE: 33
gggctatatg agatcttgaa taataaatg tgt                                33

<210> SEQ ID NO 34
<211> LENGTH: 14
<212> TYPE: DNA
<213> ORGANISM: Artificial Sequence, primer
<220> FEATURE:
<221> NAME/KEY: misc_feature
<222> LOCATION: (1)..(14)
<223> OTHER INFORMATION: primer

<400> SEQUENCE: 34
tattaataac tagt                                                    14

<210> SEQ ID NO 35
<211> LENGTH: 42
<212> TYPE: DNA
<213> ORGANISM: Artificial Sequence, primer
<220> FEATURE:
<221> NAME/KEY: misc_feature
<222> LOCATION: (1)..(42)
<223> OTHER INFORMATION: primer

<400> SEQUENCE: 35
gctacgcaga gctcgtttag tgaaccgggc actcagattc tg                     42
```

```
<210> SEQ ID NO 36
<211> LENGTH: 36
<212> TYPE: DNA
<213> ORGANISM: Artificial Sequence, primer
<220> FEATURE:
<221> NAME/KEY: misc_feature
<222> LOCATION: (1)..(36)
<223> OTHER INFORMATION: primer

<400> SEQUENCE: 36
gctgagctct agagtccttt tcttttacaa agttgg                                    36

<210> SEQ ID NO 37
<211> LENGTH: 31
<212> TYPE: DNA
<213> ORGANISM: Artificial Sequence, primer
<220> FEATURE:
<221> NAME/KEY: misc_feature
<222> LOCATION: (1)..(31)
<223> OTHER INFORMATION: primer

<400> SEQUENCE: 37
gtcgctgagg tcgacaaggc aaagagaaga g                                         31

<210> SEQ ID NO 38
<211> LENGTH: 31
<212> TYPE: DNA
<213> ORGANISM: Artificial Sequence, primer
<220> FEATURE:
<221> NAME/KEY: misc_feature
<222> LOCATION: (1)..(31)
<223> OTHER INFORMATION: primer

<400> SEQUENCE: 38
gaccggtacc gtcgacaagg cacagcagtg g                                         31

<210> SEQ ID NO 39
<211> LENGTH: 32
<212> TYPE: DNA
<213> ORGANISM: Artificial Sequence, primer
<220> FEATURE:
<221> NAME/KEY: misc_feature
<222> LOCATION: (1)..(32)
<223> OTHER INFORMATION: primer

<400> SEQUENCE: 39
ttctgtcgac gaatcccagg gggaatctca ac                                        32

<210> SEQ ID NO 40
<211> LENGTH: 35
<212> TYPE: DNA
<213> ORGANISM: Artificial Sequence, primer
<220> FEATURE:
<221> NAME/KEY: misc_feature
<222> LOCATION: (1)..(35)
<223> OTHER INFORMATION: primer

<400> SEQUENCE: 40
gtcaccttcc agagggccct ggctaagcat aacag                                     35

<210> SEQ ID NO 41
<211> LENGTH: 35
<212> TYPE: DNA
<213> ORGANISM: Artificial Sequence, primer
<220> FEATURE:
<221> NAME/KEY: misc_feature
<222> LOCATION: (1)..(35)
<223> OTHER INFORMATION: primer
```

-continued

```
<400> SEQUENCE: 41
ctgttatgct tagccagggc cctctggaag gtgac                              35

<210> SEQ ID NO 42
<211> LENGTH: 28
<212> TYPE: DNA
<213> ORGANISM: Artificial Sequence, primer
<220> FEATURE:
<221> NAME/KEY: misc_feature
<222> LOCATION: (1)..(28)
<223> OTHER INFORMATION: primer

<400> SEQUENCE: 42
aattgctgac ccccaaaata gccataag                                     28

<210> SEQ ID NO 43
<211> LENGTH: 36
<212> TYPE: DNA
<213> ORGANISM: Artificial Sequence, primer
<220> FEATURE:
<221> NAME/KEY: misc_feature
<222> LOCATION: (1)..(36)
<223> OTHER INFORMATION: primer

<400> SEQUENCE: 43
ccatgcacgt ctgcagccag catggcagaa tcgaag                            36

<210> SEQ ID NO 44
<211> LENGTH: 30
<212> TYPE: DNA
<213> ORGANISM: Artificial Sequence, primer
<220> FEATURE:
<221> NAME/KEY: misc_feature
<222> LOCATION: (1)..(30)
<223> OTHER INFORMATION: primer

<400> SEQUENCE: 44
cctgaggatc tattttccac cagtcatttc                                   30

<210> SEQ ID NO 45
<211> LENGTH: 29
<212> TYPE: DNA
<213> ORGANISM: Artificial Sequence, primer
<220> FEATURE:
<221> NAME/KEY: misc_feature
<222> LOCATION: (1)..(29)
<223> OTHER INFORMATION: primer

<400> SEQUENCE: 45
gtggaaaata gatcctcagg gccctctgg                                    29

<210> SEQ ID NO 46
<211> LENGTH: 34
<212> TYPE: DNA
<213> ORGANISM: Artificial Sequence, primer
<220> FEATURE:
<221> NAME/KEY: misc_feature
<222> LOCATION: (1)..(34)
<223> OTHER INFORMATION: primer

<400> SEQUENCE: 46
gcagtgccgg atcctcataa atgtttcctc cttc                              34

<210> SEQ ID NO 47
<211> LENGTH: 24
<212> TYPE: DNA
<213> ORGANISM: Artificial Sequence, primer
```

```
<220> FEATURE:
<221> NAME/KEY: misc_feature
<222> LOCATION: (1)..(24)
<223> OTHER INFORMATION: primer

<400> SEQUENCE: 47
gacaccatgg gaagtattta tcac                                          24

<210> SEQ ID NO 48
<211> LENGTH: 35
<212> TYPE: DNA
<213> ORGANISM: Artificial Sequence, primer
<220> FEATURE:
<221> NAME/KEY: misc_feature
<222> LOCATION: (1)..(35)
<223> OTHER INFORMATION: primer

<400> SEQUENCE: 48
cctgggattc atatcaaacc ttataacaaa tattg                              35

<210> SEQ ID NO 49
<211> LENGTH: 22
<212> TYPE: DNA
<213> ORGANISM: Artificial Sequence, primer
<220> FEATURE:
<221> NAME/KEY: misc_feature
<222> LOCATION: (1)..(22)
<223> OTHER INFORMATION: primer

<400> SEQUENCE: 49
tcctgctaag cataacagaa ac                                            22

<210> SEQ ID NO 50
<211> LENGTH: 29
<212> TYPE: DNA
<213> ORGANISM: Artificial Sequence, primer
<220> FEATURE:
<221> NAME/KEY: misc_feature
<222> LOCATION: (1)..(29)
<223> OTHER INFORMATION: primer

<400> SEQUENCE: 50
ggtttgatat gaatcccagg gggaatctc                                     29

<210> SEQ ID NO 51
<211> LENGTH: 22
<212> TYPE: DNA
<213> ORGANISM: Artificial Sequence, primer
<220> FEATURE:
<221> NAME/KEY: misc_feature
<222> LOCATION: (1)..(22)
<223> OTHER INFORMATION: primer

<400> SEQUENCE: 51
accccgtacg tcttcccgag cg                                            22

<210> SEQ ID NO 52
<211> LENGTH: 39
<212> TYPE: DNA
<213> ORGANISM: Artificial Sequence, primer
<220> FEATURE:
<221> NAME/KEY: misc_feature
<222> LOCATION: (1)..(39)
<223> OTHER INFORMATION: primer

<400> SEQUENCE: 52
gttattaatt aatggaggaa taattgaaga aggatatac                          39
```

<210> SEQ ID NO 53
<211> LENGTH: 31
<212> TYPE: DNA
<213> ORGANISM: Artificial Sequence, primer
<220> FEATURE:
<221> NAME/KEY: misc_feature
<222> LOCATION: (1)..(31)
<223> OTHER INFORMATION: primer

<400> SEQUENCE: 53
tcttctgcag gtcctgatcc ttgcttagtg c                          31

<210> SEQ ID NO 54
<211> LENGTH: 41
<212> TYPE: DNA
<213> ORGANISM: Artificial Sequence, primer
<220> FEATURE:
<221> NAME/KEY: misc_feature
<222> LOCATION: (1)..(41)
<223> OTHER INFORMATION: primer

<400> SEQUENCE: 54
gaccatgtta cccctttacc attaactccc taatatcaaa c               41

<210> SEQ ID NO 55
<211> LENGTH: 44
<212> TYPE: DNA
<213> ORGANISM: Artificial Sequence, primer
<220> FEATURE:
<221> NAME/KEY: misc_feature
<222> LOCATION: (1)..(44)
<223> OTHER INFORMATION: primer

<400> SEQUENCE: 55 gtaaagggt aacatggtca gcatcgcatt ctacggggga atcc             44

<210> SEQ ID NO 56
<211> LENGTH: 38
<212> TYPE: DNA
<213> ORGANISM: Artificial Sequence, primer
<220> FEATURE:
<221> NAME/KEY: misc_feature
<222> LOCATION: (1)..(38)
<223> OTHER INFORMATION: primer

<400> SEQUENCE: 56
ccatgcacgt ctcgagccag catgggagac cctttgac                   38

<210> SEQ ID NO 57
<211> LENGTH: 37
<212> TYPE: DNA
<213> ORGANISM: Artificial Sequence, primer
<220> FEATURE:
<221> NAME/KEY: misc_feature
<222> LOCATION: (1)..(37)
<223> OTHER INFORMATION: primer

<400> SEQUENCE: 57
cgagctagag gtcgactcaa tttggtttat tagtaac                    37

<210> SEQ ID NO 58
<211> LENGTH: 32
<212> TYPE: DNA
<213> ORGANISM: Artificial Sequence, primer
<220> FEATURE:
<221> NAME/KEY: misc_feature
<222> LOCATION: (1)..(32)
<223> OTHER INFORMATION: primer

```
<400> SEQUENCE: 58
gcaatggaat gacatccctc agctgccagt cc                                32

<210> SEQ ID NO 59
<211> LENGTH: 42
<212> TYPE: DNA
<213> ORGANISM: Artificial Sequence, primer
<220> FEATURE:
<221> NAME/KEY: misc_feature
<222> LOCATION: (1)..(42)
<223> OTHER INFORMATION: primer

<400> SEQUENCE: 59
gggatgtcat tccattgcca ccatgggaag tatttatcac ta                     42

<210> SEQ ID NO 60
<211> LENGTH: 34
<212> TYPE: DNA
<213> ORGANISM: Artificial Sequence, primer
<220> FEATURE:
<221> NAME/KEY: misc_feature
<222> LOCATION: (1)..(34)
<223> OTHER INFORMATION: primer

<400> SEQUENCE: 60
gtcgagcacg cgtttgccta gcaacatgag ctag                              34

<210> SEQ ID NO 61
<211> LENGTH: 34
<212> TYPE: DNA
<213> ORGANISM: Artificial Sequence, primer
<220> FEATURE:
<221> NAME/KEY: misc_feature
<222> LOCATION: (1)..(34)
<223> OTHER INFORMATION: primer

<400> SEQUENCE: 61
gtcgagccaa ttgttgccta gcaacatgag ctag                              34

<210> SEQ ID NO 62
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: P7.5E sequence

<400> SEQUENCE: 62
aaaagtagaa aatatattct aatttatt                                     28

<210> SEQ ID NO 63
<211> LENGTH: 19
<212> TYPE: DNA
<213> ORGANISM: Artificial Sequence
<220> FEATURE:
<221> NAME/KEY: promoter
<222> LOCATION: (1)..(19)
<223> OTHER INFORMATION: T7 promter

<400> SEQUENCE: 63
taatacgact cactatagg                                               19

<210> SEQ ID NO 64
<211> LENGTH: 48
<212> TYPE: DNA
```

-continued

```
<213> ORGANISM: Artificial Sequence
<220> FEATURE:
<221> NAME/KEY: terminator
<222> LOCATION: (1)..(48)
<223> OTHER INFORMATION: T7 terminator

<400> SEQUENCE: 64
ctagcataac cccttggggc ctctaaacgg gtcttgaggg gtttttttg                    48
```